US008734792B2

(12) United States Patent
Tedder

(10) Patent No.: US 8,734,792 B2
(45) Date of Patent: May 27, 2014

(54) REAGENTS AND TREATMENT METHODS FOR AUTOIMMUNE DISEASES

(75) Inventor: Thomas F. Tedder, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/467,235

(22) Filed: May 9, 2012

(65) Prior Publication Data

US 2012/0301472 A1 Nov. 29, 2012

Related U.S. Application Data

(60) Division of application No. 11/890,743, filed on Aug. 6, 2007, now abandoned, which is a continuation of application No. 10/372,481, filed on Feb. 21, 2003, now abandoned.

(60) Provisional application No. 60/420,472, filed on Oct. 21, 2002, provisional application No. 60/359,419, filed on Feb. 21, 2002.

(51) Int. Cl.
*A61K 39/395* (2006.01)
*A61K 39/40* (2006.01)
*C07K 16/00* (2006.01)

(52) U.S. Cl.
USPC .............. 424/130.1; 424/133.1; 424/134.1; 424/138.1; 424/141.1; 424/143.1; 424/144.1; 424/152.1; 424/153.1; 424/155.1

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,484,892 A * | 1/1996 | Tedder et al. | 530/388.73 |
| 5,530,101 A | 6/1996 | Queen et al. | |
| 5,595,721 A | 1/1997 | Kaminski et al. | |
| 5,686,072 A | 11/1997 | Uhr et al. | |
| 5,789,554 A * | 8/1998 | Leung et al. | 435/6.14 |
| 5,831,142 A | 11/1998 | Tedder | |
| 5,843,398 A | 12/1998 | Kaminski et al. | |
| 6,015,542 A | 1/2000 | Kaminski et al. | |
| 6,022,521 A | 2/2000 | Wahl et al. | |
| 6,090,365 A | 7/2000 | Kaminski et al. | |
| 6,183,744 B1 | 2/2001 | Goldenberg | |
| 6,187,287 B1 | 2/2001 | Leung et al. | |
| 6,251,362 B1 | 6/2001 | Wahl et al. | |
| 6,254,868 B1 | 7/2001 | Leung et al. | |
| 6,287,537 B1 | 9/2001 | Kaminski et al. | |
| 6,306,393 B1 | 10/2001 | Goldenberg | |
| 6,331,415 B1 | 12/2001 | Cabilly et al. | |
| 6,399,061 B1 | 6/2002 | Anderson et al. | |
| 6,455,043 B1 | 9/2002 | Grillo-Lopez | |
| 6,921,846 B1 | 7/2005 | Tedder | |
| 2002/0071807 A1 | 6/2002 | Goldenberg | |
| 2003/0124058 A1 | 7/2003 | Goldenberg | |
| 2003/0133930 A1 | 7/2003 | Goldenberg | |
| 2003/0202975 A1 | 10/2003 | Tedder | |
| 2004/0001828 A1 | 1/2004 | Tuscano et al. | |
| 2004/0202658 A1 | 10/2004 | Benyunes | |
| 2004/0219156 A1 | 11/2004 | Goldenberg et al. | |
| 2005/0118182 A1 | 6/2005 | Pastan et al. | |
| 2007/0258981 A1 | 11/2007 | Hilbert et al. | |
| 2007/0264260 A1 | 11/2007 | Tuscano et al. | |

FOREIGN PATENT DOCUMENTS

| | | |
|---|---|---|
| EP | 0669836 B1 | 9/1995 |
| EP | 0866131 | 9/1998 |
| EP | 0 660 721 B1 | 10/2008 |
| WO | WO 91/13974 | 9/1991 |
| WO | WO 94/27638 | 12/1994 |
| WO | WO 00/67796 | 5/2000 |
| WO | WO 00/74718 | 12/2000 |
| WO | WO 01/97858 | 12/2001 |
| WO | WO 03/072036 | 9/2003 |
| WO | WO 03/072736 | 9/2003 |
| WO | WO 03/093320 A2 | 11/2003 |
| WO | WO 2007/103469 | 9/2007 |
| WO | WO 2007/103470 | 9/2007 |

OTHER PUBLICATIONS

Tedder. Annu. Rev. Immunol. 1997. 15:481-504.*
Engel et al. J. Exp. Med. 1995 181:1581-1586.*
Morrison et al. Advances In . Immunology 1989; vol. 44, pp. 65-92.*
U.S. Appl. No. 11/715,307, filed Mar. 6, 2007, Jones et al.
Buchsbaum et al., "Therapy with unlabeled and 131I-labeled pan-B-cell monoclonal antibodies in nude mice bearing Raji Burkitt's lymphoma xenografts", Cancer Res. 52(23):6476-6481 ( 1992).
Chaouchi et al., "B cell antigen receptor-mediated apoptosis. Importance of accessory molecules CD19 and CD22, and of surface IgM cross-linking", J. Immunol. 154(7):3096-3104 ( 1995).
Friedberg, "Developing new monoclonal antibodies for aggressive lymphoma: a challenging road in the rituximab era", Clin. Cancer Res. 10(16):5297-5298 (2004).
Ghetie et al., "Combination immunotoxin treatment and chemotherapy in SCID mice with advanced, disseminated Daudi lymphoma", Int. J. Cancer 68(1):93-96 (1996).
Ghetie et al., "Antitumor activity of Fab' and IgG-anti-CD22 immunotoxins in disseminated human B lymphoma grown in mice with severe combined immunodeficiency disease: effect on tumor cells in extranodal sites", Cancer Res. 51(21):5876-5880 (1991).
Ghetie et al., "The antitumor activity of an anti-CD22 immunotoxin in SCID mice with disseminated Daudi lymphoma is enhanced by either an anti-CD 19 antibody or an anti-CD 19 immunotoxin", Blood 80(9):23 15-2320 ( 1992).

(Continued)

*Primary Examiner* — Chun Dahle
(74) *Attorney, Agent, or Firm* — Andrus Intellectual Property Law, LLP

(57) ABSTRACT

The invention concerns treatment methods using anti-CD22 monoclonal antibodies with unique physiologic properties. In particular, the invention concerns methods for the treatment of B-cell malignancies and autoimmune diseases by administering an effective amount of a blocking anti-CD22 monoclonal antibody specifically binding to the first two Ig-like domains, or to an epitope within the first two Ig-like domains of native human CD22 (hCD22).

19 Claims, 23 Drawing Sheets

(56) References Cited

OTHER PUBLICATIONS

Goldenberg et al., "Monoclonal antibody therapy of cancer", N J Med. 87(11 Spec No):913-918 (1990).

Goldenberg, "New developments in monoclonal antibodies for cancer detection and therapy", CA Cancer J. Clin. 44(1):43-64 (1994).

Hekman et al., "Initial experience with treatment of human B cell lymphoma with anti-CDI9 monoclonal antibody", Cancer Immunol. Immunother. 32(6):364-372 (1991).

http://www.immunomedics/com/news/97/110597.htm.

"Immunomedics, Inc." date of access: Jun. 15, 2003.

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).

Khazaeli et al., "Low V-region immunogenicity of therapeutic doses of 131I-LL2 mouse monoclonal antibody in lymphoma patients", J. Immunother. 16(2): 170 (abstract No. 89) (1994).

Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).

Leblond et al., "Lymphoproliferative disorders after organ transplantation: a report of 24 cases observed in a single center", J. Clin. Oncol. 13(4):961-968 (1995).

Leonard et al., "Epratuzumab, a new anti-CD22, humanized, monoclonal antibody, for the therapy of non-Hodgkin's lymphoma (NHL): phase I/II trial results", Blood 94(suppl. I, aprt 1):92a-93a, Abstract No. 404 (1999).

Leonard et al., "Combination antibody therapy with epratuzumab and rituximab in relapsed or refractory non-Hodgkin's lymphoma", J. Clin. Oncol. 23(22):5044-5051 (2005); Epub Jun. 13, 2005.

Leonard et al., "Epratuzumab, a humanized anti-CD22 antibody, in aggressive non-Hodgkin's lymphoma: phase I/II clinical trial results", Clin. Cancer Res. 10(16):5327-5334 (2004).

Leonard et al., "Phase I/II trial of epratuzumab (humanized anti-CD22 antibody) in indolent non-Hodgkin's lymphoma", J. Clin. Oncol. 21(16):3051-3059 (2003).

Leung et al., "Chimerization of LL2, a rapidly internalizing antibody specific for B cell lymphoma", Hybridoma 13(6):469-476 (1994).

Leung et al., "Construction and characterization of a humanized, internalizing, B-cell (CD22)-specific, leukemia/lymphoma antibody, LL2", Mol. Immunol. 32(17-18):1413-1427 (1995).

Linden et al., "Dose-fractionated radioimmunotherapy in non-Hodgkin's lymphoma using DOTA-conjugated, 90Y-radiolabeled, humanized anti-CD22 monoclonal antibody, epratuzumab", Clin. Cancer Res. 11(14):5215-5222 (2005).

Losman et al., "Generation of a high-producing clone of a humanized anti-B-cell lymphoma monoclonal antibody (hLL2)", Cancer 80(12 Suppl):2660-2666 (1997).

Maloney et al., "Phase I clinical trial using escalating single-dose infusion of chimeric anti-CD20 monoclonal antibody (IDEC-C2B8) in patients with recurrent B-cell lymphoma", Blood 84(8):2457-2466 (1994).

May et al., "Selective killing of normal and neoplastic human B cells with anti-CD 19- and anti-CD22-ricin A chain immunotoxins", Cancer Drug Delivery 3(4):261-272 (1986).

Qu et al.,"Development of humanized antibodies as cancer therapeutics", Methods 36(1):84-95 (2005).

Sharkey et al., "Treatment of non-Hodgkin's lymphoma (NHL) with LL2, an anti-CD22 monoclonal antibody", J. Immunother. 16(2):160 (abstract 48) (1994).

Van Horssen et al., "Highly potent CD22-recombinant ricin A results in complete cure of disseminated malignant B-cell xenografts in SCID mice but fails to cure solid xenografts in nude mice", Int. J. Cancer 68:378-383 (1996).

Vose et al., "Therapy of refractory non-Hodgkin's lymphoma (NHL) with $^{131}$I-LL2 (anti-CD22) radioimmunotherapy (RIT): Results of a repetitive dosing trial", Blood 88(10 suppl. 1, part 1-2):567A (abstract 2258; 38th Annual Meeting of the American Society of Hematology, Orlando, FL (1996).

"Anti-Human Fas monoclonal antibody CH11 light chain cDNA," Database Geneseq [Online] (Jan. 18, 1999) retrieved from EBI accession No. GSN:AAV66736.

"Anti-Human Fas monoclonal antibody CH11 light chain," Database Geneseq [Online] (Jan. 18, 1999)retrieved from EBI accession No. GSN:AAW71889.

Abaza et al., "Effects of amino acid substitutions outside an antigenic site on protein binding to monoclonal antibodies of predetermined specificity obtained by peptide immunization: demonstration with region 94-100 (antigenic site 3) of myoglobin," J. Protein Chem. 11(5):433-444 (1992).

Abbas et al., Cellular and Molecular Immunology, 5th Ed., pp. 506-512, Saunders Publishing, 2003.

Araoz et al., "CT and MR imaging of primary cardiac malignancies," Radiographics 19(6):1421-1434 (1999).

Benjamini et al., Immunology, 4th Ed., p. 60, Wiley-Liss Publishers, 2000.

Colman, P.M., "Effects of amino acid sequence changes on antibody-antigen interactions," Res Immunol. Jan. 1994;145(1):33-36 (1994).

Engel et al., "The same epitope on CD22 of B lymphocytes mediates the adhesion of erythrocytes, T and B lymphocytes, Neutrophils, and monocytes.", J. Immunol., 150(11): 4719-4732 (1993).

Haas et al., "CD22 Regulates Normal and Malignant B Survival In Vivo." J. Immunol. 177:3063-3073 (2006).

Janeway et al., Immunobiology, 3rd Ed., pp. 3:1-3:2, Garland Publishing, Inc. New York I1997.

Kantor et al., "An unbiased analysis of V(H)-D-J(H) sequences from B-1a, B-1b, and conventional B cells," J. Immunol. 158(3):1175-1186 (1997).

Lederman et al., "A single amino acid substitution in a common African allele of the CD4 molecule ablates binding of the monoclonal antibody, OKT4," Mol. Immunol. 28( 11):1171-1181 (1991).

Li et al., "beta-Endorphin omission analogs: dissociation of immunoreactivity from other biological activities," Proc. Natl. Acad. Sci. U.S.A. 77(6):3211-3214 (1980).

Poe et al., 2004, "CD22 regulates B lymphocyte function in vivo through both ligand-dependent and ligand-independent mechanisms." Nat. Immunol. 5(10):1078-1087.

Rudikoff et al., "Single amino acid substitution altering antigen-binding specificity," Proc. Natl. Acad. Sci. U.S.A. 79(6):1979-1983 (1982).

St.Clair et al., "New prospects for autoimmune disease therapy: B cells on deathwatch." Arthritis and Rheumatism 54(1):1-9 (2006).

Stein et al., "Epitope specificity of the anti-(B cell lymphoma) monoclonal antibody LL2," Cancer Immunology and Immunotherapy, 37(5):293-298 (1993).

Tedder et al., "CD22, a B lymphocyte-specific adhesion molecule that regulates antigen receptor signaling," Annu. Rev. Immunol. 15:481-504 (1997).

Tedder et al., "CD22: A multifunctional receptor regulates B lymphocyte survival and signal transduction." Adv. Immunol. 88:1-50 (2005).

Tuscano et al., "Anti-CD22 ligand-blocking antibody HB22.7 has independent lymphomacidal properties and augments the efficacy of $^{90}$Y-DOTA-peptide-Lym-1 in lymphoma, xenografts.", Blood, 101(9): 3641-3647, May 2003.

Tuscano et al., "CD22 cross-linking generates B-cell antigen receptor-independent signals that activate the JNKISAPK signaling cascade," Blood 94(4):1382-1392 (1999).

Tuscano et al., "Engagement of the adhesion receptor CD22 triggers a potent stimulatory signal for B cells and blocking CD22/CD22L interactions impairs T-cell proliferation.", Blood, 87(11):4723-4730 (1996).

Tuscano et al., "Involvement of p72syk kinase, p53/56lyn kinase and phosphatidyl inositol-3 kinase in signal transduction via the human B lymphocyte antigen CD22," Eur. J. Immunol. 26(6):1246-1252 (1996).

Van Regenmortel, M.H.V., "Mapping epitope structure and activity: from one-dimensional prediction to four-dimensional description of antigenic specificity," Methods: A Companion to Methods in Enzymology 9(3):465-472 (1996).

American Cancer Society and National Comprehensive Cancer Network, "Non-Hodgkin's Lymphoma," Version 1, pp. 1-76, Oct. 2003.

(56) References Cited

OTHER PUBLICATIONS

American Heritage Dictionary of the English Language, "Cure," 4th Ed., Houghton Mifflin Company, Publishers, p. 445 (2000).
Anderson et al., 1997, "Targeted anti-cancer therapy using rituximab, a chimaeric anti-CD20 antibody (IDEC—C2B8) in the treatment of non-Hodgkin's B-cell lymphoma", Biochem. Soc. Transac. 25:705-708.
Brorson et al., "Mutational analysis of avidity and fine specificity of anti-levan antibodies", J. Immunol. 163:6694-6701 (1999).
Brummell et al., "Probing the combining site of an anti-carbohydrate antibody by saturation-mutagenesis: role of the heavy-chain CDR3 residues," Biochem. 32:1180-1187 (1993).
Burks et al., "In vitro scanning saturation mutagenesis of an antibody binding pocket", Proc. Natl. Acad. Sci. USA 94:412-417 (1997).
Carnahan et al., "Epratuzumab, a humanized monoclonal antibody targeting CD22: Characterization of in vivo properties." Clin. Cancer Res. 9:3982s-3990s (2003).
Casset et al., "A peptide mimetic of an anti-CD4 monoclonal antibody by rational design", Biochem. Biophys. Res. Comm. 307:198-205 (2003).
Chen et al., "Selection and analysis of an optimized anti-VEGF antibody: crystal structure of an affinity-matured Fab in complex with antigen", J. Mol. Biol. 293:865-881 (1999).
Coleman et al., 2003, "Epratuzumab: Targeting B-Cell Malignancies through CD22", Clin. Cancer Res. 9:399 1S-4S.
De Pascalis et al., "Grafting of "abbreviated" complementarity-determining regions containing specificity-determining residues essential for ligand contact to engineer a less immunogenic humanized monoclonal antibody", J. Immunol. 169:3076-3084 (2002).
De Vita et al., 2002, "Efficacy of selective B cell blockade in the treatment of rheumatoid arthritis: evidence for a pathogenetic role of B cells". Arthritis Rheumatism 46:2029-2033.
Dufner et al., "Harnessing phage and ribosome display for antibody optimisation", Trends Biotechnol. 24:523-529 (2006).
Edwards et al., 2001, "Sustained improvement in rheumatoid arthritis following a protocol designed to deplete B lymphocytes", Rheumatology 40:205-211.
Engel et al., "Identification of the ligand-binding domains of CD22, a member of the immunoglobulin superfamily that uniquely binds a sialic acid-dependent ligand," J. Exp. Med. 181:1581-1586 (1995).
Flavell et al., "Systemic therapy with 3BIT, a triple combination cocktail of anti-CD 19, -CD22, and -CD38-saporin immunotoxins, is curative of human B-cell lymphoma in severe combined immunodeficient mice," Cancer Res. 57:4824-4829 (1997).
Harris et al., "A revised European-American classification of lymphoid neoplasms: a proposal from the International Lymphoma Study Group," Blood 84(5): 1361-1392 (1994).
Holm et al., "Functional mapping and single chain construction of the anti-cytokeratin 8 monoclonal antibody TS1", Mol. Immunol. 44:1075-1084 (2007).
Jacobson et al., "Epidemiology and estimated population burden of selected autoimmune diseases in the United States," Clin Immunol. Immunopathol. 84:223-243 (1997).
Jang et al., "The structural basis for DNA binding by an anti-DNA autoantibody", Molec. Immunol. 35:1207-1217 (1998).
Kabat et al., "Sequences of Proteins of Immunological Interest" (U.S. Department of Health and Human Services, Washington, D.C.) 5th ed., pp. xv-xvi (1991).
Kaminiski et al., "Radioimmunotherapy of B-cell lymphoma with [131I] Anti-B1 (Anti-CD20) antibody," N. Eng. J. Med. 329:459-465 (1993).
Kobayashi et al., "Tryptophan H33 plays an important role in primidine (6-4) pyrimidone photoproduct binding by a high-affinity antibody", Protein Engineer. 12:879-884 (1999).
Leandro et al., "Clinical outcome in 22 patients with rheumatoid arthritis treated with B lymphocyte depletion", Ann. Rheum. Dis. 61:883-888 (2002).
Li et al., "Three-dimensional structures of the free and antigen-bound Fab from monoclonal anti lysozyme antibody HyHEL-63", Biochemistry, 39:6296-6309 (2000).
Maas et al., "Mechanisms of tumor regression induced by low doses of interleukin-2", In Vivo, 5:637-641 (1991).
MacCallum et al., "Antibody-antigen interactions: contact analysis and binding site topography", J. Mol. Biol. 262:732-745 (1996).
Maloney et al., "IDEC-C2B8 (Rituximab) anti-CD20 monoclonal antibody therapy in patients with relapsed low-grade non-Hodgkin's lymphoma", Blood 90:2188-2195 (1997).
Maloney et al., "IDEC-C2B8: results of a phase I multiple-dose trial in patients with relapsed non-Hodgkin's lymphoma", J. Clin. Oncol. 15:3266-3274 (1997).
McLaughlin et al., "Clinical status and optimal use of rituximab for B-cell lymphomas", Oncology 12:1763-1769 (1998).
Notice of Opposition to European Patent EP 0 660 721 filed on Jul. 29, 2009 in the European Patent Office.
O'Donnell et al., "Dose timing schedule and the choice of targeted epitope alter the efficacy of anti-CD22 immunotherapy in mice bearing human lymphoma xenografts", Cancer Immunol. Immunother., 58:2051-2058 (2009).
Office Action mailed Nov. 4, 2008 in U.S. Appl. No. 11/715,308, pp. 1-13.
Office Action mailed Jun. 24, 2009 in U.S. Appl. No. 11/715,308, pp. 1-13.
Office Action mailed Oct. 17, 2005 in U.S. Appl. No. 10/371,797, pp. 1-19.
Office Action mailed May 3, 2006 in U.S. Appl. No. 10/371,797, pp. 1-9.
Office Action mailed Jul. 8, 2009 in U.S. Appl. No. 11/592,750, pp. 1-11.
Onrust et al., "Rituximab", Drugs 58:79-88 (1999).
Press et al., "Immunotherapy of non-Hodgkin's lymphomas", Hematology 221-240 (2001).
Reff et al., "Depletion of B cells in vivo by a chimeric mouse human monoclonal antibody to CD20", Blood 83:435-455 (1994).
Renner et al., "Monoclonal antibodies in the treatment of non-Hodgkin's lymphoma: Recent results and future prospects", Leukemia 11(Suppl): S55-S59 (1997).
Sato et al., "CD22 negatively and positively regulates signal transduction through the B lymphocyte antigen receptor," Semin. Immunol. 10:287-297 (1998).
SCORE Search Results Details for U.S. Appl. No. 11/592,750, Alignment of MAb 4197X light chain variable region (Accession No. AAR70828) with SEQ ID No. 23 of U.S. Appl. No. 11/592,750, Jul. 6, 2009, pp. 1-2.
Silverman et al., "Rituximab therapy and autoimmune disorders: Prospects for anti-B cell therapy", Arthritis Rheum. 48:1484-1492 (2002).
Smith et al., "Rituximab (monoclonal anti-CD20 antibody): Mechanisms of action and resistance", Oncogene 22:7359-7368 (2003).
Stamenkovic et al., "The B-cell antigen CD22 mediates monocyte and erythrocyte adhesion", Nature, 345:74-79 (May 3, 1990).
Tedder et al., "CD20: a regulator of cell-cycle progression of B lymphocytes", Immunol. Today 15:450-454 (1994).
Torres et al., "Identification and characterization of the murine homologue of CD22, a B lymphocyte-restricted adhesion molecule", J. Immunol. 149:2641-2649 ( 1992).
Tuscano et al., "Engagement of the adhesion receptor CD22 triggers a potent stimulatory signal for B cells and blocking CD22/CD22L interactions impairs T-cell proliferation". Blood, 87(11):4723-4730 (1996).
Vajdos et al., "Comprehensive functional maps of the antigen-binding site of an anti-ErbB2 antibody obtained with shotgun scanning mutagenesis". J. Mol. Biol. 320:415-428 (2002).
Weiner et al., "Monoclonal antibody therapy of cancer", Semin. Oncol. 26:43-51 (1999).
Wilson et al., "cDNA cloning of the B cell membrane protein CD22: a mediator of B-B cell interactions," J. Exp. Med. 173:137-146 (1991).
Wu et al., "Humanization of a murine monoclonal antibody by simultaneous optimization of framework and CDR residues", J. Mol. Biol. 294:151-162 (1999).

(56) References Cited

OTHER PUBLICATIONS

Kreitman et al., 1999, "Complete regression of human B-cell lymphoma xenografts in mice treated with recombinant anti-CD22 immunotoxin RFB4(dsFv)-PE38 at doses tolerated by cynomolgus monkeys," Int. J. Cancer, 81:148-155.

Martin et al., 2009, "Imaging and pharmacokinetics of $^{64}$Cu-DOTA-HB22.7 administered by intravenous, intraperitoneal, or subcutaneous injection to mice bearing non-Hodgkin's lymphoma xenografts," Mol. Imaging Biol., 11:79-87.

Newton et al., 2001, "Potent and specific antitumor effects of an anti-CD22-targeted cytotoxic ribonuclease: potential for the treatment of non-Hodgkin lymphoma," Blood 97:528-535.

O'Donnell et al., 2009, "Treatment of non-Hodgkin's lymphoma xenografts with the HB22.7 anti-CD22 monoclonal antibody and phosphatase inhibitors improves efficacy," Cancer Immunol. Immunother., 58:1715-1722.

Office Action mailed Jan. 14, 2010 in U.S. Appl. No. 11/592,750, pp. 1-10.

Office Action mailed Jan. 7, 2010 in U.S. Appl. No. 11/715,308, pp. 1-6.

Reply of the Patent Proprietor to the Notice of Opposition of EP 0 600 721 B1, May 11, 2010, pp. 1-25.

Declaration of Thomas F. Tedder, Ph.D. dated Nov. 14, 2003, pp. 1-2.

Declaration of Thomas F. Tedder, Ph.D. Under 37 C.F.R. § 1.132 dated May 27, 1995, pp. 1-7.

* cited by examiner

Figure 1

```
          ┌─► domain 1
  1       │MHLLGPWLLLLVLEYLAFSDSSKWVFEHIPETLYAWEGACVWIPC

45        TYRALDGDLESFILFHNPEYNKNTSKFDGTRLYESTKDGKVPSEQKRVC

95        LGDKNKNCTLSIHPVHLNDSGQLGLRMESKTEKWM
              domain 1 ◄─┐ ┌─► domain 2
130        ERIHLNVSE│ │RPPPPHQLPPEIQESQEVTLTCLLNFSCYGYPIQL 175        QWLLEGVPMRQAAVTSTSLTIKSVFTRSELKFSPQWSHIGKIVTC
                     domain 2 ◄─┐ ┌─► domain 3
220        QLQDADGKFLSNDTVQLNVKH│ │TPKLEIKVTPSDAIVREGDSVTMT 265        CEVSSSNPEYTTVSWLKDGTSLKKQNTFTLNLREVTKDQSGKYCC
                    domain 3 ◄─┐ ┌─► domain 4
310        QVSNDVGPGRSEEVFLQVQY│ │APEPSTVQILHSPAVEGSQVEFLCM 355        SLANPLPTNYTWYHNGKEMQGRTEEKVHIPKILPWHAGTYSCVAE
                    domain 4 ◄─┐ ┌─► domain 5
400        NILGTGQRGPGAELDVQY│ │PPKKVTTVIQNPMPIREGDTVTLSCNY 445        NSSNPSVTRYEWKPHGAWEEPSLGVLKIQNVGWTNTTIACARCNS
                  domain 5 ◄─┐ ┌─► domain 6
490        WCSWASPVALNVQY│ │APRDVRVRKIKPLSEIHSGNSVSLQCDFSSS 535        HPKEVQFFWEKNGRLLGKESQLNFDSISPEDAGSYSCWVNNSIGQ
                  domain 6 ◄─┐ ┌─► domain 7
580        TASKAWTLEVLY│ │APRRLRVSMSPGDQVMEGKSATLTCESDANPPV 625        SHYTWFDWNNQSLPHHSQKLRLEPVKVQHSGAYWCQQTNSVGKGR
              domain 7 ◄─┐
670        SPLSTLTVYY│ │ SPETIGREVAVGLGSCLAILILAICGLKLQRRWKR

715        TQSQQGLQENSSCQSFPVRNKKVRRAPLSEOPHSLGCYNPMMEDG

760        ISYTTLRFPEMNIPKTGDAESSEMQRPPRTCDDTVTYSALHKRQV

805        GDYENVIPDFPEDEGIHYSELIQFGVGERPQAQENVDYVILKH*
```

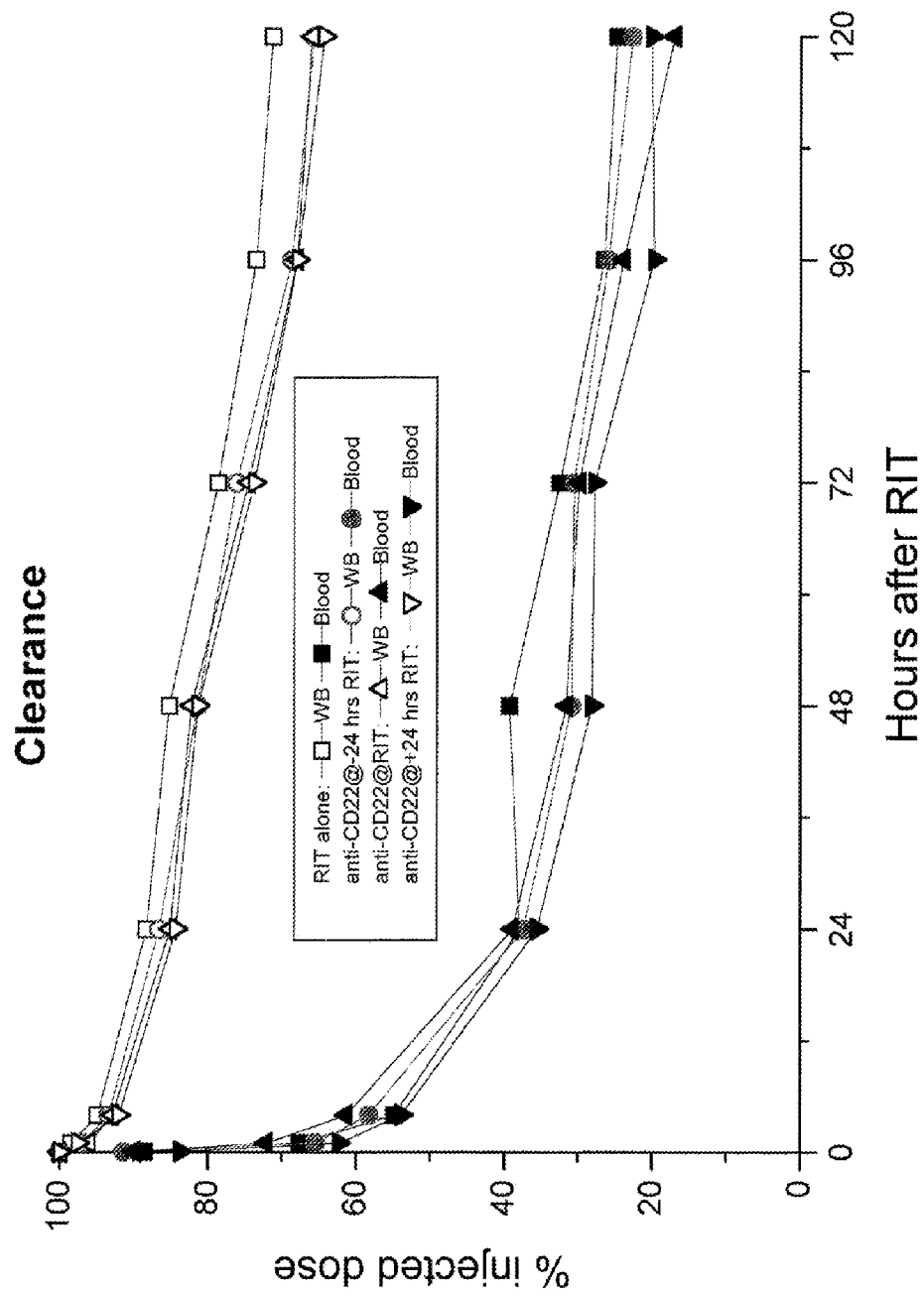

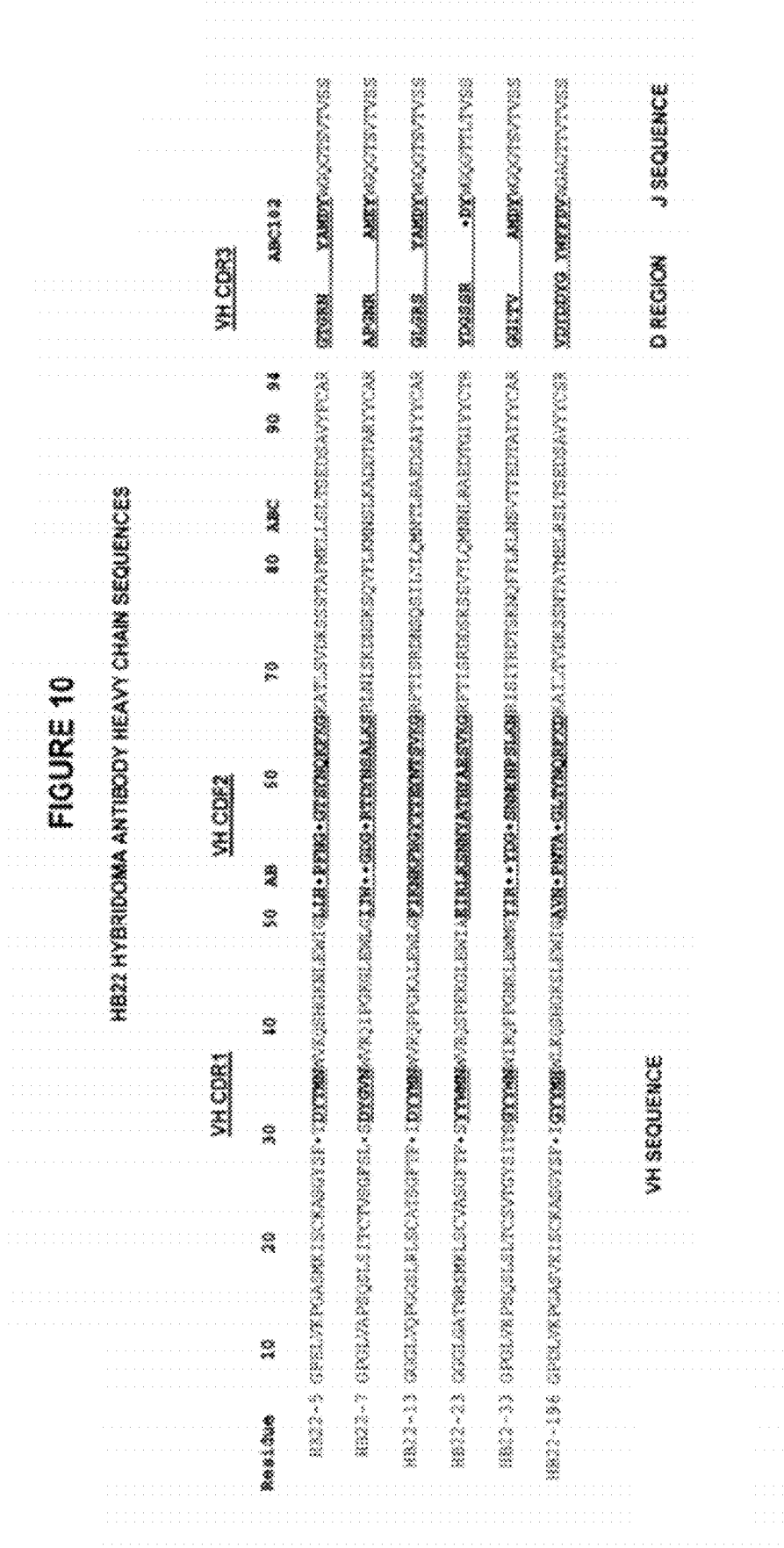

Figure 11

HB22-5 VH Sequence

```
1                                           10                          20
  E   V   Q   L   Q   E   S   G   P   E   L   V   K   P   G   A   S   M   K   I
  GAG GTG CAG CTG CAG GAG TCT GGA CCT GAG CTG GTG AAG CCT GGA GCT TCA ATG AAG ATA    60

21                                          30
  S   C   K   A   S   G   Y   S   F   T   D   Y   T   M   N   W   V   K   Q
  TCC TGC AAG GCT TCT GGT TAC TCA TTC ACT GAC TAC ACC ATG AAC TGG GTG AAG CAG 41                                          50
  H   G   K   N   L   E   W   I   G   L   L   H   P   F   N   G   G   T   S
  CAT GGA AAG AAC CTT GAG TGG ATT GGA CTT CTT CAT CCT TTC AAT GGT GGT ACT AGC 61                                          70                          80
  N   Q   K   F   K   G   K   A   T   L   S   V   D   K   S   S   T   A   F
  AAC CAG AAG TTC AAG GGC AAG GCC ACA TTA TCT GTA GAC AAG TCA TCC AGC ACA GCC TTC   240

81                                          90                          100
  M   E   L   L   S   L   T   S   E   D   S   A   V   Y   F   C   A   R   G   T
  ATG GAG CTC CTC AGT CTG ACA TCT GAG GAC TCT GCA GTC TAT TTC TGT GCA AGA GGG ACA   300

101                                         110                         120
  G   R   N   Y   A   M   D   Y   W   G   Q   G   T   S   V   T   V   S   S
  GGT CGG AAC TAT GCT ATG GAC TAC TGG GGT CAA GGA ACC TCA GTC ACC GTC TCC TCA       357
```

Figure 12

HB22-7 VH Sequence

```
 1  E   V   Q   L   Q   E   S   G   P          10  G   L   V   A   P   S   Q   S   L          20  S   I          60
    GAG GTG CAG CTG CAG GAG TCT GGA            CCT GGG CTG GTG GCG CCC TCA CAG AGC           CTG TCC ATC

21 T   C   T   V   S   G   F   S   L          30  T   S   Y   G   V   H   W   V   R          40  Q   I         120
    ACA TGC ACC GTC TCA GGG TTC TCA            TTA ACC AGT TAT GGT GTA CAC TGG GTT           CGC CAG ATT

41 P   G   K   G   L   E   W   L   G          50  V   I   W   G   G   G   N   T   D          60  Y   N         180
    CCA GGA AAG GGT CTG GAG TGG CTG            GGA GTA ATA TGG GGT GGT GGA AAC ACA           GAC TAT AAT

61 S   A   L   K   S   R   L   N   I          70  S   K   D   N   S   K   S   Q   V          80  F   L         240
    TCA GCT CTC AAA TCC AGA CTG AAC            ATC AGC AAG GAC AAC TCC AAG AGC CAA           GTT TTC TTG

81 K   M   N   S   L   K   A   D   D          90  T   A   R   Y   Y   C   A   R   P         100  G   G         300
    AAA ATG AAC AGT CTC AAA GCT GAT            GAC ACA GCC AGG TAC TAC TGT GCC AGA           CCC GGT

101 N   R   A   M   D   Y   W   G   Q         110  G   T   S   V   T   V   S   S             117         351
    AAT AGG GCT ATG GAC TAC TGG GGT            CAA GGA ACC TCA GTC ACC GTC TCC TCA
```

Figure 13

HB22-13 VH Sequences

Figure 14

HB22-23 VH Sequence

```
1                          10                         20
E   V   Q   L   Q   E   S   G   G   G   L   V   Q   P   G   G   S   L   K   L
GAG GTG CAG CTG CAG GAG TCT GGA GGA GGC TTG GTA CAG CCT GGA GGG TCC ATG AAA CTC  60

21                         30                         40
S   C   V   A   S   G   F   T   F   S   Y   Y   W   M   N   W   V   R   Q   S
TCC TGT GTT GCC TCT GGA TTC ACT TTC AGT TAC TAC TGG ATG AAC TGG GTC CGC CAG TCT  120

41                         50                         60
P   E   K   G   L   E   W   I   A   E   I   R   L   K   S   N   N   Y   A   T
CCA GAG AAG GGG CTT GAG TGG ATT GCT GAA ATT AGA TTG AAA TCT AAT AAT TAT GCA ACA  180

61                         70                         80
H   Y   A   E   S   V   K   G   R   F   T   I   S   R   D   D   S   K   S   S
CAT TAT GCG GAG TCT GTG AAA GGG AGG TTC ACC ATC TCA AGA GAT GAT TCC AAA AGT AGT  240

81                         90                         100
V   Y   L   Q   M   N   N   L   R   A   E   D   T   G   I   Y   Y   C   T   R
GTC TAC CTG CAA ATG AAC AAC TTA AGA GCT GAA GAC ACT GGC ATT TAT TAC TGT ACC AGG  300

101                        110                        120
Y   D   G   S   S   R   D   Y   W   G   Q   G   T   T   L   T   V   S   S
TAT GAT GGT TCC TCC CGG GAC TAC TGG GGC CAA GGC ACC ACT CTC ACA GTC TCC TCA  357
```

HB22-33 VH Sequence

FIGURE 16

HB22-196 VH Sequence

```
1                                      10                                          20
E   V   Q   L   Q   E   S   G   P   D   L   V   K   P   G   A   S   V   K   I
GAG GTG CAG CTG CAG GAG TCT GGA CCT GAC CTG GTG AAG CCT GGG GCT TCA GTG AAG ATA   60

21                                     30                                          40
S   C   K   A   S   G   Y   S   F   I   G   Y   Y   M   H   W   L   K   Q   S
TCC TGT AAG GCT TCT GGT TAC TCA TTC ATT GGC TAT TAC ATG CAC TGG CTG AAG CAG AGC  120

41                                     50                                          60
H   G   K   S   L   E   W   I   G   A   V   N   P   N   T   A   G   L   T   Y
CAT GGA AAG AGC CTT GAG TGG ATT GGA GCT GTT AAT CCT AAC ACT GCT GGT CTT ACC TAC  180

61                                     70                                          80
N   Q   R   F   K   D   K   A   I   L   T   V   D   K   S   S   N   T   A   Y
AAC CAG AGG TTC AAG GAC AAG GCC ATA TTA ACT GTA GAC AAG TCA TCC AAC ACA GCC TAT  240

81                                     90                                         100
M   E   L   R   S   L   T   S   E   D   S   A   V   Y   Y   C   S   R   V   D
ATG GAG CTC CGC AGC CTG ACA TCT GAG GAC TCT GCG GTC TAT TAC TGT TCA AGA GTG GAC  300

101                                    110                                        120
Y   D   D   Y   G   Y   W   F   F   D   V   W   G   A   G   T   T   V   T   V
TAT GAT GAC TAC GGG TAC TGG TTC TTC GAT GTC TGG GGC GCA GGG ACC ACG GTC ACC GTC  360

121
S   S
TCC TCA                                                                           366
```

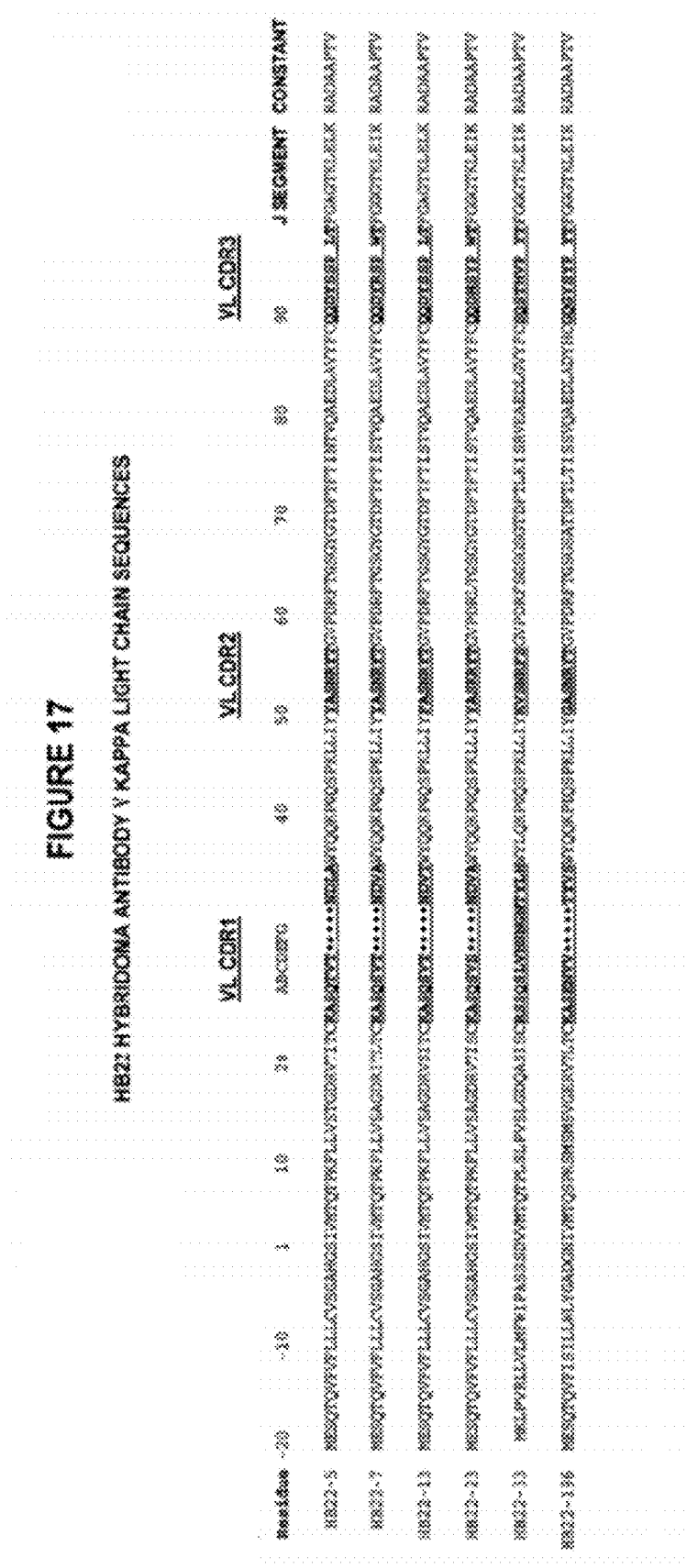

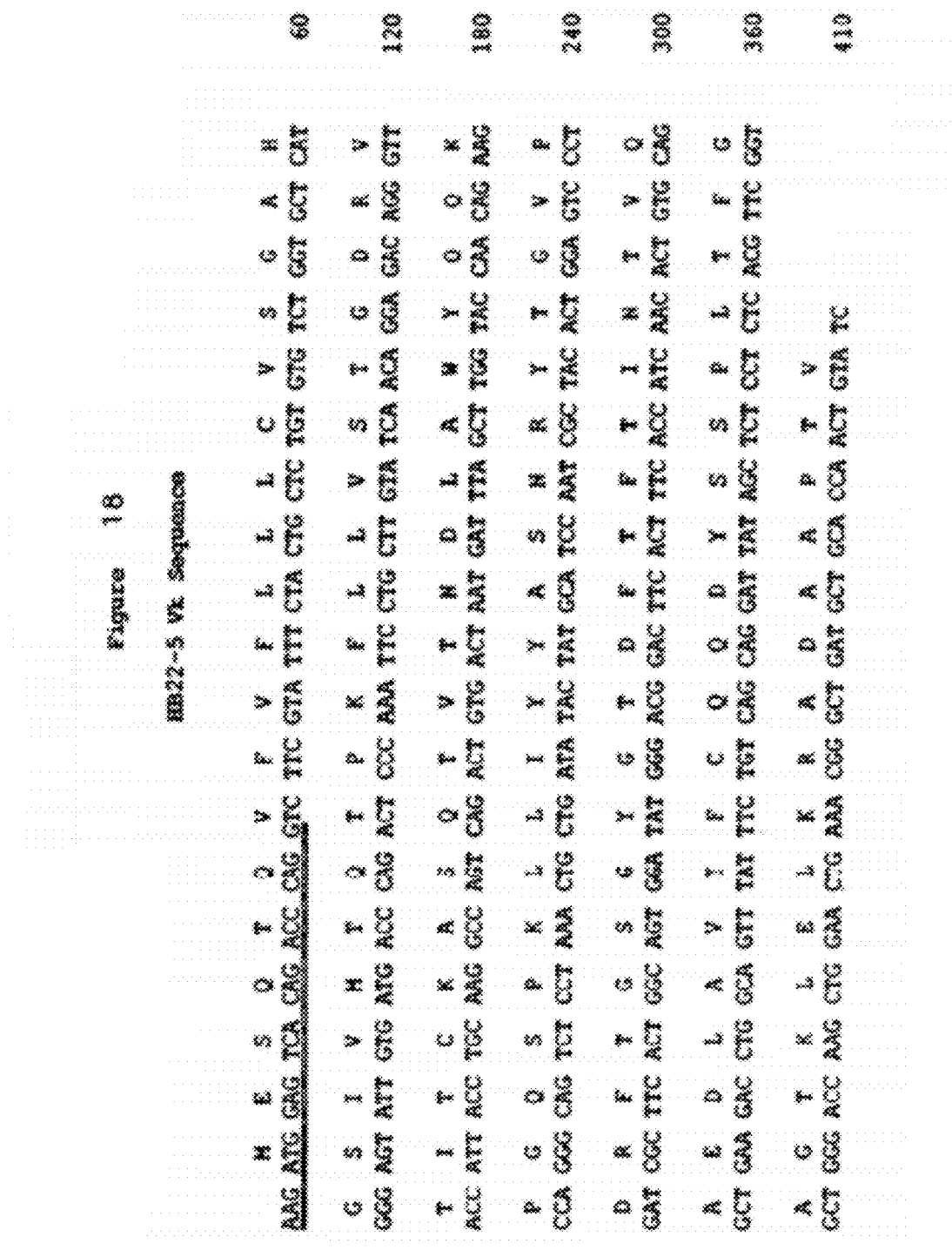

Figure 19

HB22-7 Vk Sequence

```
     M   E   S   Q   T   Q   V   F   V   F   L   L   C   V   S   G   A   H              60
    AAG ATG GAG TCA CAG ACC CAG GTC TTC GTA TTT CTA CTC TGT GTT TCT GGT GCT CGT

G   S   I   V   M   T   Q   T   P   K   F   L   L   V   S   A   G   D   R   I     120
    GGG AGT ATT GTC ATG ACC CAG ACT CCC AAA TTC CTG CTT GTA TCA GCA GGA GAC AGG ATT

T   L   T   C   K   A   S   Q   S   V   T   N   D   V   A   W   Y   Q   Q   K     180
    ACC TTA ACC TGC AAG GCC AGT CAG AGT GTG ACT AAT GAT GTA GCT TGG TAC CAG CAG AAG

P   G   Q   S   P   K   L   L   I   Y   Y   A   S   N   R   Y   A   G   V   P     240
    CCA GGG CAG TCT CCT AAA CTG CTG ATA TAC TAT GCA TCC AAT CGC TAC GCT GGA GTC CCT

D   R   F   T   G   S   G   Y   G   T   D   F   T   F   T   I   S   T   V   Q     300
    GAT CGC TTC ACT GGC AGT GGA TAT GGG ACG GAT TTC ACT TTC ACC ATC AGC ACT GTG CAG

A   E   D   L   A   V   Y   F   C   Q   Q   D   Y   S   S   P   W   T   F   G     360
    GCT GAA GAC CTG GCA GTT TAT TTC TGT CAG CAG GAT TAT AGC TCT CCG TGG ACG TTC GGT

G   G   T   K   L   E   I   K   R   A   D   A   A   P   T   V   S                  410
    GGA GGC ACC AAG CTC GAA ATC AAA CGG GCT GAT GCT GCA CCA ACT GTA TC
```

Figure 20

MB22-13 VK Sequence

Figure 21

HB22-23 Vk Sequence

```
  M   E   S   Q   T   Q   V   F   V   F   L   L   C   V   S   G   A   H
AAG ATG GAG TCA CAG ACC CAG GTC TTC GTA TTT CTA CTG CTC TGT GTG TCT GGT GCT CAT   50

G   S   I   V   M   T   Q   T   P   K   F   L   L   V   S   A   G   D   R   V
GGG AGT ATT GTG ATG ACC CAG ACT CCC AAA TTC CTG CTT GTA TCA GCA GGA GAC AGG GTC  100

T   I   S   C   K   A   S   Q   S   V   S   N   D   V   A   W   Y   Q   Q   K
ACC ATA AGC TGC AAG GCC AGT CAG AGT GTG AGT AAT GAT GTA GCT TGG TAC CAA CAG AAG  150

P   G   Q   S   P   K   L   L   I   Y   A   S   K   R   Y   T   G   V   P   P
CCA GGG CAG TCT CCT AAA CTG CTG ATA TAC GCA TCC AAG CGC TAT ACT GGA GTC CCT      200

D   R   L   T   G   S   G   Y   G   T   D   F   T   F   T   I   S   T   V   Q
GAT CGC CTC ACT GGC AGT GGA TAT GGG ACG GAT TTC ACT TTC ACC ATC AGC ACT GTG CAG  250

A   E   D   L   A   V   Y   F   C   Q   Q   D   H   S   Y   P   W   T   F   G
GCT GAA GAC CTG GCA GTT TAT TTC TGT CAG CAG GAT CAT AGC TAT CCG TGG ACG TTC GGT  300

G   G   T   K   L   E   I   K   R   A   D   A   A   P   T   V
GGA GGC ACC AAG CTG GAG ATC AAA CGC GCT GAT GCT GCA CCA ACT GTA TC               350
```

Figure 22

HB22-33 Vk Sequences

HB22-196 Vk Sequence

REAGENTS AND TREATMENT METHODS FOR AUTOIMMUNE DISEASES

This application is a divisional of U.S. patent application Ser. No. 11/890,743, filed Aug. 6, 2007 now abandoned, which is a continuation of U.S. patent application Ser. No. 10/372,481, filed Feb. 21, 2003 now abandoned, which claims priority from U.S. Provisional Application Ser. No. 60/359,419, filed Feb. 21, 2002 and U.S. Provisional Application Ser. No. 60/420,472, filed Oct. 21, 2002, each of which is incorporated herein by reference in its entirety.

The present invention was made with the support of Grant No. CA 81776 from the National Institutes of Health. The United States government has certain rights in this invention.

BACKGROUND OF THE INVENTION

1. Field of the Invention

The present invention concerns the therapeutic use of certain anti-CD22 monoclonal antibodies with unique physiologic properties. More specifically, the invention concerns methods of treating B-cell malignancies, such as lymphomas and leukemias, and autoimmune diseases with blocking anti-CD22 antibodies having unique pro-apoptotic properties.

2. Description of the Related Art

CD22 is a membrane glycophosphoprotein found on nearly all B lymphocytes and most B-cell lymphomas. Cross-linking CD22 triggers CD22 tyrosine phosphorylation, and assembles a complex of effector proteins that activate the stress-activated protein kinase (SAPK) pathway. CD22 cross-linking provides a potent costimulatory signal in primary B-cells and pro-apoptotic signal in neoplastic B-cells. Structurally, CD22 is a member of the "sialoadhesin" subclass of the immunoglobulin (Ig) gene superfamily, having seven extracellular Ig domains with a single amino-terminal V-set Ig domain and six C-2 set Ig domains. Wilson et al, *J. Exp. Med.* 173:137-146 (1991); Engel et al., *J. Exp. Med.* 181: 1581-1586 (1995): and Torres et al., *J. Immunol.* 149:2641-2649 (1992). It has been shown that CD22 is a critical lymphocye-specific signal transduction molecule which negatively and positively regulates B lymphocyte antigen receptor (BCR) signaling by recruiting signaling effector molecules to physiologically pertinent sites. Tedder et al., *Annu. Rev. Immunol.* 15:481-504 (1997); Sato et al., *Immunology* 10:287-297 (1998).

Anti-CD22 antibodies have been described, for example in U.S. Pat. Nos. 5,484,892; 6,183,744; 6,187,287; 6,254,868, and in Tuscano et al., *Blood* 94(4):1382-92 (1999). The use of monoclonal antibodies, including anti-CD22 antibodies, in the treatment of non-Hodgkin's lymphoma is reviewed, for example, by Renner et al., *Leukemia* 11(Suppl. 2):S55-9 (1997). A. humanized anti-CD22 antibody, LymphoCide™ (empatuzumab, Immunomedics, Inc.) is in Phase III clinical trials for the treatment of indolent and aggressive forms of non-Hodgkin's lymphomas. An yttrium-90-labeled version of this antibody is currently in Phase I clinical trials for the same indication.

Despite recent advances in cancer therapy, B-cell malignancies, such as the B-cell subtype of non-Hodgkin's lymphoma, and chronic lymphocytic leukemia, are major contributors of cancer-related deaths. Accordingly, there is a great need for further, improved therapeutic regimens for the treatment of B-cell malignancies. Autoimmune diseases as a whole cause significant morbidity and disability. Based on incidence data collected from 1965 to 1995, it has been estimated that approximately 1,186,015 persons will develop a new autoimmune disease over the next 5 years, Jacobsen et al. (*Clin. Immunol. Immunopathol.* 84:223 (1997)) evaluated over 130 published studies and estimated that in 1996, 8.5 million people in the United States (3.2% of the population) had at least one of the 24 autoimmune diseases examined in these studies. Considering the major impact of autoimmune diseases on public health, effective and safe treatments are needed to address the burden of these disorders. Thus, there is a need in the art for improved reagents and methods for treating autoimmune disease.

SUMMARY OF THE INVENTION

The present invention concerns an improved clinical approach for the treatment of B-cell malignancies and autoimmune disease in human patients, taking advantage of the unique properties of certain blocking anti-CD22 monoclonal antibodies.

In one aspect, the invention concerns a method for treating a human patient diagnosed with a B-cell malignancy, comprising (1) administering to the patient an effective amount of a blocking anti-CD22 monoclonal antibody specifically binding to the first two Ig-like domains or to an epitope associated with the first two Ig-like domains of native human CD22 (hCD22) of SEQ ID NO: 1, and (2) monitoring the response of the malignancy to the treatment.

In a further aspect, the invention concerns a method for treating a subject, (e.g., a human patient) diagnosed with an autoimmune disease, comprising (1) administering to the subject an effective amount of a blocking anti-CD22 monoclonal antibody and, optionally, (2) monitoring the response of the autoimmune disease to the treatment.

As further aspects, the present invention provides methods of reducing B cell activity, reducing the number of B cells or B cell subsets or even essentially eliminating B cells or particular B cell subsets, increasing turnover of B cells and/or reducing antibody production by B cells by administering to a subject (e.g., a human patient) an effective amount of a blocking anti-CD22 monoclonal antibody; and optionally, (2) monitoring the response to the treatment. By "reducing" it is meant at least about a 25%, 35%, 50% or 75% decrease or more. By "essentially eliminating" it is meant at least about a 90%, 95%, 985 or more decrease or more. By "increasing turnover", it is meant at least about a 25%, 35%, 50%, 75%, 100%, 150% or more elevation in turnover rate.

In a particular embodiment the antibody used binds to essentially the same epitope as an antibody selected from the gronp consisting of HB22-7 (HB11347), HB22-23 (HB11349), HB22-33, HB22-5, HB22-13, and HB22-196, preferably HB22-7, HB22-23, or HB22-33, more preferably HB22-7 or HB22-33.

In a further embodiment, the antibody blocks CD22 binding to its ligand by at least 70%, preferably by at least 80%.

In another embodiment, the antibody comprises a heavy chain comprising a $V_H$ sequence having at least about 95% sequence identity with the sequence of amino acids 1 to 100 of SEQ ID NO: 9 (KB22-5 $V_H$ sequence); or amino acids 1 to 97 of SEQ ID NO: 11 (HB22-7 $V_H$ sequence); or amino acids 1 to 100 of SEQ ID NO: 13 (HB22-13 $V_H$ sequence); or amino acids 1 to 100 of SEQ ID NO: 15 (HB22-23 $V_H$ sequence); or amino acids 1 to 98 of SEQ ID NO: 17 (HB22-33 $V_H$ sequence); or amino acids 1 to 100 of SEQ ID NO: 19 (HB22-196 $V_H$ sequence).

In yet another embodiment, the antibody comprises a heavy chain comprising a $V_H$ sequence having at least about 95% sequence identity with the sequence of amino acids 1 to 97 of SEQ ID NO: 11 (HB22-7 $V_H$ sequence); or amino acids 1 to 100 of SEQ ID NO: 15 (HB22-23 V$_H$ sequence); or amino acids 1 to 98 of SEQ ID NO: 17 (HB22-33 V$_H$ sequence).

In a still, further embodiment, the antibody comprises a V$_H$ sequence selected from the group consisting of amino acids 1 to 97 of SEQ ID NO: 11 (HB22-7 V$_H$ sequence); amino acids 1 to 100 of SEQ ID NO: 15 (HB22-23 V$_H$ sequence); and amino acids 1 to 98 of SEQ ID NO: 17 (HB22-33 V$_H$ sequence).

In a different embodiment, the antibody comprises a light chain comprising a V$_\kappa$ sequence having at least about 95% sequence identity with the amino acid sequence of SEQ ID NO: 21 (HB22-5 V$_\kappa$ sequence); or SEQ ID NO: 23 (HB22-7 V$_\kappa$ sequence); or SEQ ID NO: 25 (HB22-13 V$_\kappa$ sequence); or SEQ ID NO: 27 (HB22-23 V$_\kappa$ sequence); or SEQ ID NO: 29 (HB22-33 V$_\kappa$ sequence); or SEQ ID NO: 31 (HB22-196 V$_\kappa$ sequence).

In a particular embodiment, the antibody comprises a light chain comprising a V$_\kappa$ sequence having at least about 95% sequence identity with the amino acid sequence of SEQ ID NO: 23 (HB22-7 V$_\kappa$ sequence); or SEQ ID NO: 27 (HB22-23 V$_\kappa$ sequence); or SEQ ID NO: 29 (HB22-33 V$_\kappa$ sequence).

In a further embodiment, the antibody comprises a V$_\kappa$ sequence selected from the group consisting of the amino acid sequence of SEQ ID NO: 23 (HB22-7 V$_\kappa$ sequence); SEQ ID NO: 27 (HB22-23 V$_\kappa$ sequence); and SEQ ID NO: 29 (HB22-33 V$_\kappa$ sequence).

In a preferred embodiment, the antibody comprises V$_H$ and V$_\kappa$ sequences selected from the group consisting of amino acids 1 to 97 of SEQ ID NO: 11 (HB22-7 V$_H$ sequence) and the amino acid sequence of SEQ ID NO: 23 (HB22-7 V$_\kappa$ sequence); amino acids 1 to 100 of SEQ ID NO: 15 (HB22-23 V$_H$ sequence) and the amino acid sequence of SEQ ID NO: 27 (HB22-23 V$_\kappa$ sequence); and amino acids 1 to 98 of SEQ ID NO: 17 (HB22-33 V$_H$ sequence) and the amino acid sequence of SEQ ID NO: 29 (HB22-33 V$_\kappa$ sequence).

In a different aspect, the invention concerns nucleic acid encoding any of the antibody heavy or light chain variable regions discussed above, or any portion thereof.

As a further aspect the present invention provides polypeptides comprising the heavy or light chain variable regions discussed above, or a portion thereof.

The targeted condition can be any type of autoimmune disease or B-cell malignancy, including but not limited to localized B-cell malignancies, or any other condition in which B cells or antibodies are implicated. Typical representatives of B-cell malignancies are B-cell subtype of non-Hodgkin's lymphoma, Burkitt's lymphoma, multiple myeloma, chronic lymphocytic leukemia, hairy cell leukemia, and prolymphocytic leukemia.

The treatment methods of the present invention may be performed without any further treatment of malignant B cells or autoimmune disease. With respect to B-cell malignancy, the treatment method of the present invention typically provides improved cure rate and/or increased survival and/or superior tumor volume reduction when compared to no treatment, combination treatment with the same antibody and radioimmunotherapy, or with radioimmunotherapy alone.

The antibody can be a complete antibody, or an antibody fragment, including, for example. Fab, Fab', F(ab')$_2$, and Fv fragments, diabodies, linear antibodies, single-chain antibody molecules, and multispecific antibodies formed from antibody fragments. Thus, the antibody may have an additional antigen specificity, e.g. may be a bispecific antibody. The bispecific antibody may, for example, additionally bind to another epitope to CD22. In addition, the bispecific antibody may have binding specificity for other antigens, such as, CD19, CD20, CD52, CD3, CD28, or HLA-DR10 (Lym-1); or for Fc receptors, e.g. CD16, CD64 and CD89.

The antibody may be chimeric, humanized, primatized, or human.

The administration of the antibody may be performed by any conventional route, such as intravenous (i.v.) administration by repeated intravenous infusions.

The response to the treatment may be monitored by methods well known for a skilled practitioner, including monitoring shrinkage of a solid tumor, e.g. by magnetic resonance imaging (MRI), or by measuring improvement or stabilization in clinical indicia of autoimmune disease, as known by those skilled in the art.

BRIEF DESCRIPTION OF THE DRAWINGS

FIG. 1 shows the amino acid sequence of human CD22 (hCD22), where the boundaries of the Ig-like domains (domains 1-7) are indicated FIG. 2, Whole body autoradiography of Raji and Ramos tumor-bearing nude mice injected with $^{111}$In-2IT-BAD-antiCD22 (HB22-7). Mice were sacrificed and autoradiographed 48 hours after injection. Upper image is Raji-tumored mouse, lower image is Ramos-tumored mouse.

FIG. 9. RIT clearance was assessed by measuring radioactivity in whole body (WB) and blood daily for 5 days after initiation of treatment with RIT. The results were reported after adjusting for decay based on the $T_{1/2}$ of $^{90}$Y. There were no significant differences in RIT clearance in any of the CMRIT treatment groups.

FIG. 10. $V_H$ amino acid sequence analysis of anti-CD22 antibodies (Abs) that block ligand binding. Amino acid numbering and designations of the origins of the coding sequence for each Ab is according to the convention of Kabat et al. (*Sequences of Proteins of Immunological Interest*, U.S. Government Printing Office, Bethesda, Md., 1991), where amino acid positions 1-94, CDR1 and 2, and FR1, 2, and 3 are encoded by a $V_H$ gene. Sequences that overlap with the 5' PCR primers are not shown. A dot indicates a gap inserted in the sequence to maximize alignment of similar amino acid sequences. Gaps in the sequences were introduced between $V_H$, D and J segments for clarity. Indicated as bold and underlined are the $V_H$ CDR1, $V_H$ CDR2, and $V_H$ CDR3 of HB22-5 (SEQ ID NO:32, SEQ ID NO:38, and SEQ ID NO:44), HB22-7 (SEQ ID NO:34, SEQ ID NO:40, and SEQ ID NO:46), HB22-13 (SEQ ID NO:36, SEQ ID NO:42, and SEQ ID NO:48), HB22-23 (SEQ ID NO:37, SEQ ID No:43, and SEQ ID NO:49), HB22-33 (SEQ ID NO:35, SEQ ID NO:41, and SEQ ID NO:47), and HB22-196 (SEQ ID NO:33, SEQ ID NO:39, and SEQ ID NO:45).

Figure 13:
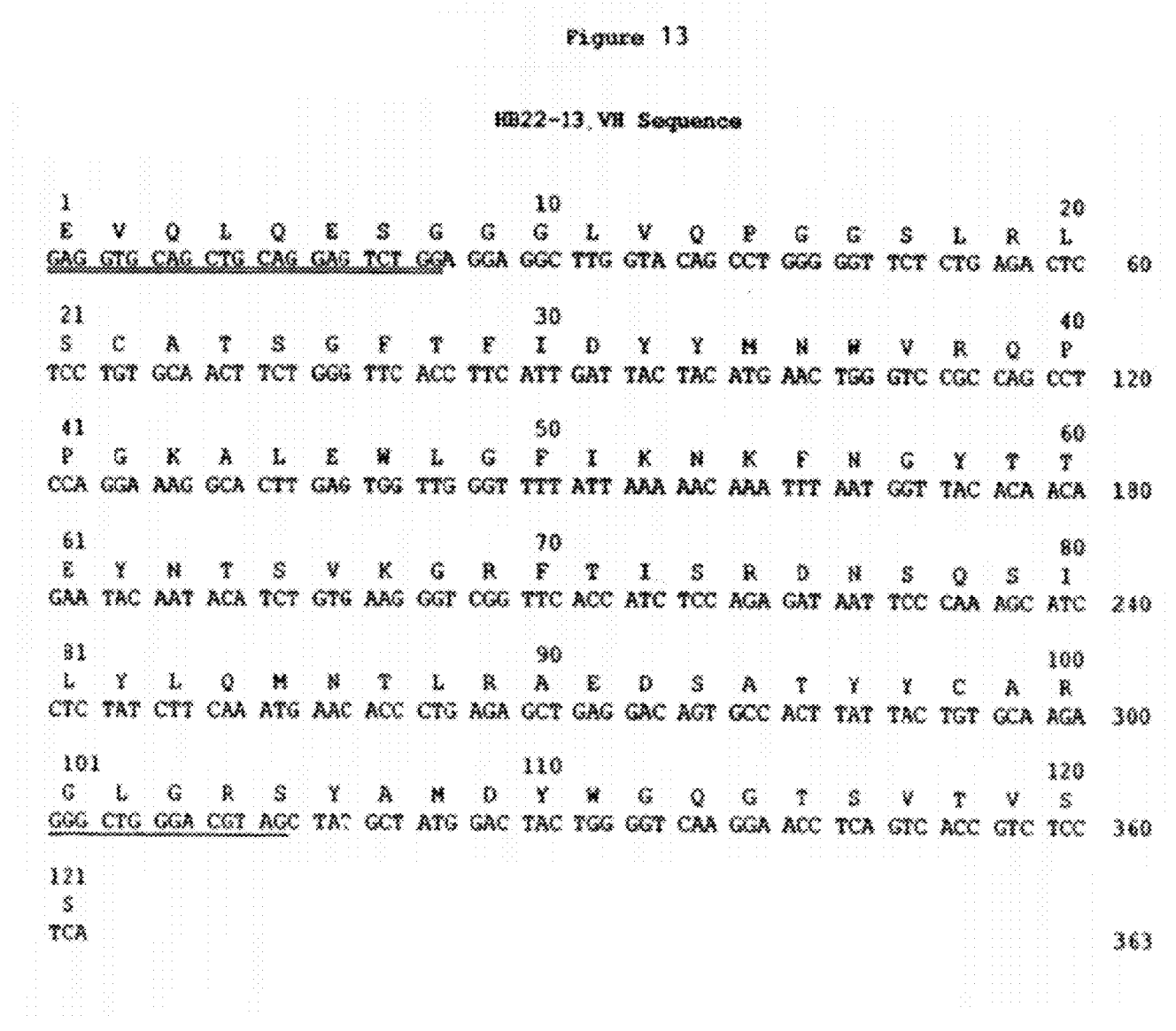

FIGS. 11-16. Nucleotide and encoded amino acid sequences for heavy chain $V_H$D-$J_H$ junctional sequences for anti-CD22 Abs from hybridomas HB22-5 (SEQ ID NOS: 8 and 9), HB22-7 (SEQ ID NOS: 10 and 11); HB22-13 (SEQ ID NOS: 12 and 13); HB22-23 (SEQ ID NOS: 14 and 15); HB22-33 (SEQ ID NOS: 16 and 17); and HB22-196 (SEQ ID NOS: 18 and 19). Sequences that overlap with the 5' PCR primers are indicated by double underlining. D region sequences are underlined.

FIG. 17. Light chain $V_\kappa$ amino acid sequence analysis of anti-CD22 Abs that block ligand binding. Amino acid, numbering and designation of origins of the coding sequence for each Ab is according to the convention of Kabat et al., supra. The amino acid following the predicted signal sequence cleavage site is numbered 1. A dot indicates a gap inserted in the sequence to maximize alignment of similar amino acid sequences. Gaps in the sequences were introduced between $V_\kappa$, J segments and κ constant region (double underlined) sequences for clarity. Indicated as bold and underlined are the $V_\kappa$ CDR1, $V_\kappa$ CDR2, and $V_\kappa$ CDR3 of HB22-5 (SEQ ID NO:50, SEQ ID NO:56, and SEQ ID NO:62), HB22-7 (SEQ ID NO:51, SEQ ID NO:57, and SEQ ID NO:63), HB22-13 (SEQ ID NO:52, SEQ ID NO:58, and SEQ ID NO:64), HB22-23 (SEQ ID NO:53, SEQ ID NO:59, and SEQ ID NO:65), HB22-33 (SEQ ID NO:54, SEQ ID NO:60, and SEQ ID NO:66), and HB22-196 (SEQ ID NO:55, SEQ ID NO:61, and SEQ ID NO:67).

Figure 20:
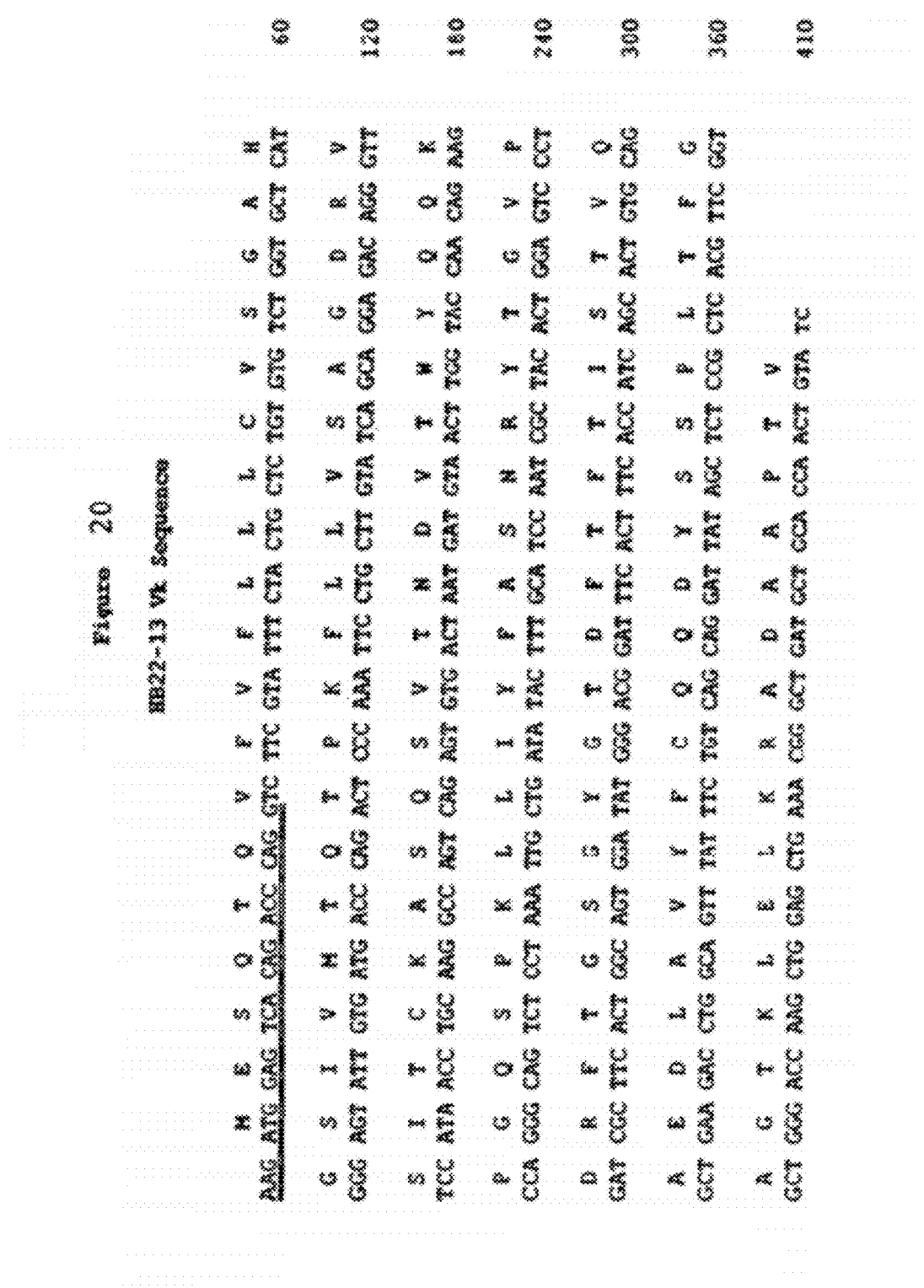
Figure 22:
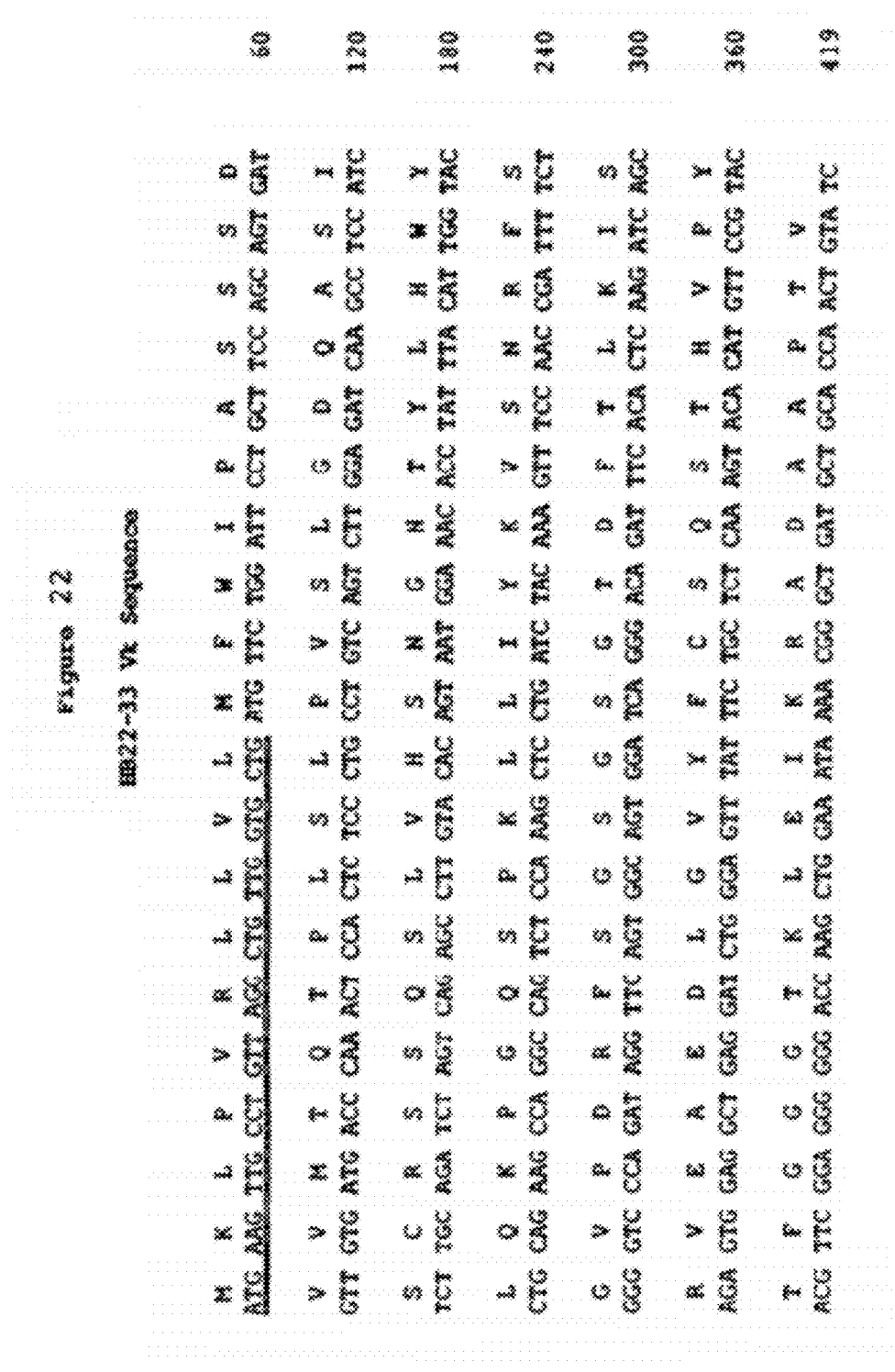

FIGS. 18-23. Nucleotide and deduced amino acid sequences for kappa light chain V-J-constant region junctional sequences for anti-CD22 Abs from hybridomas HB22-5 (SEQ ID NOS: 20 and 21); HB22-7 (SEQ ID NOS: 22 and 23); HB22-13 (SEQ ID NOS: 24 and 25): HB22-23 (SEQ ID NOS: 26 and 27); HB22-33 (SEQ ID NOS: 28 and 29); and HB22-196 (SEQ ID NOS: 30 and 31). Sequences that overlap with the 5' PCR primers are indicated by double underlining.

DETAILED DESCRIPTION OF THE PREFERRED EMBODIMENTS

Figure 2:
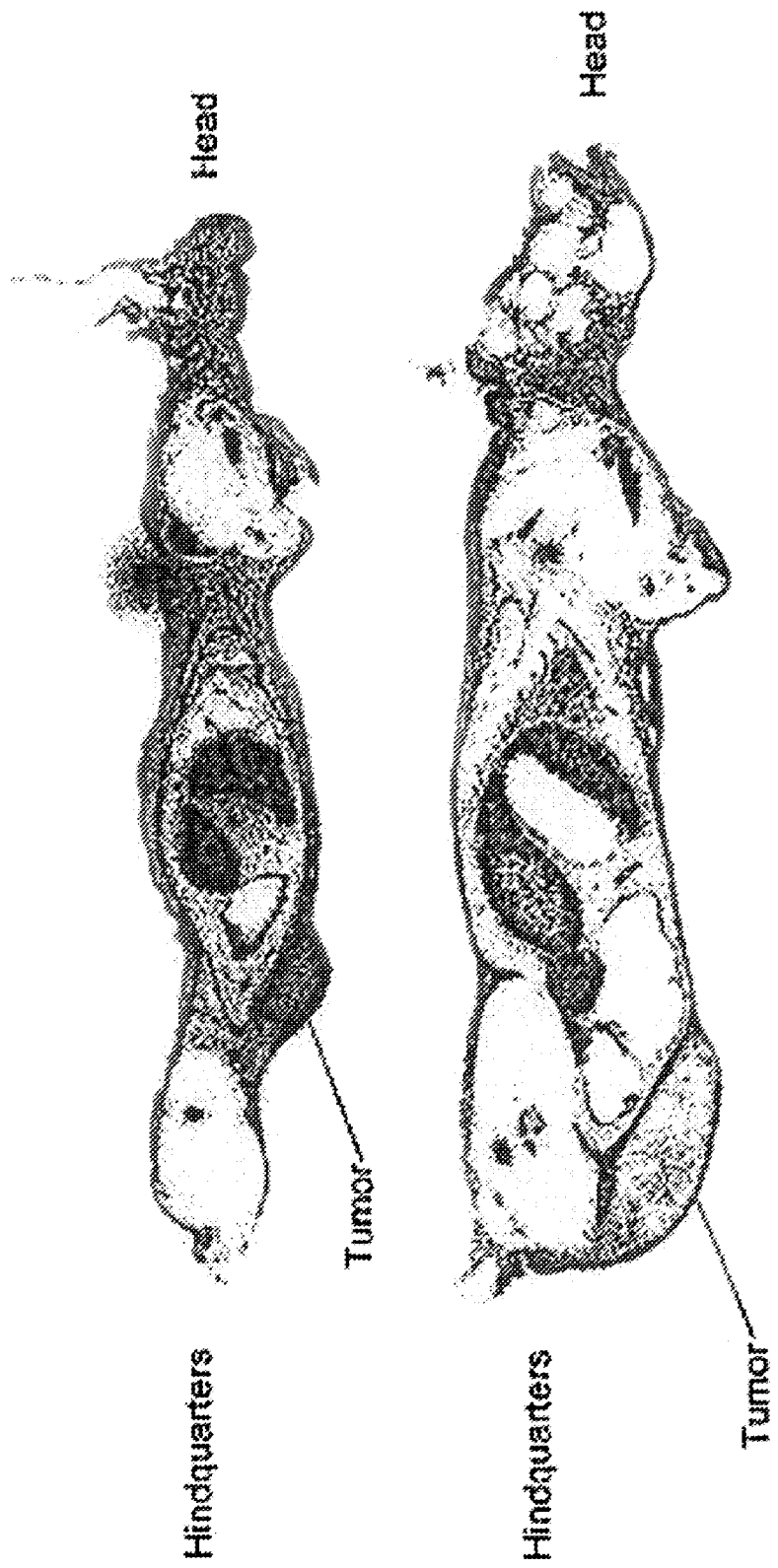

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety,

A. DEFINITIONS

Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "immunoglobulin" (Ig) is used to refer to the immunity-conferring portion of the globulin proteins of serum, and to other glycoproteins, which may not occur in nature but have the same functional characteristics. The term "immnoglobulin" or "Ig" specifically includes "antibodies" (Abs). While antibodies exhibit binding specificity to a specific antigen, immunoglobulins include both antibodies and other antibody-like molecules that lack antigen specificity. Native immunoglobulins are secreted by differentiated B cells termed plasma cells, and immunoglobulins without any antigen specificity are produced at low levels by the lymph system and at increased levels by myelomas. As used herein, the terms "immunoglobulin," "Ig," and grammatical variants thereof are used to include antibodies (as hereinabove defined), and Ig molecules without antigen specificity.

Native immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains.

The main Ig isotypes (classes) found in serum, and the corresponding Ig heavy chains, shown in parentheses, are listed below;

IgG (γ chain): the principal Ig in serum, the main antibody raised in response to an antigen, this antibody crosses the placenta;

IgE (ε chain): this Ig binds tightly to mast cells and basophils, and when additionally bound to antigen, causes release of histamine and other mediators of immediate hypersensitivity; plays a primary role in allergic reactions, including hay fever, asthma and anaphylaxis; and may serve a protective role against parasites;

IgA (α chain): this Ig is present in external secretions, such as saliva, tears, mucous, and colostrum;

IgM (μ chain): the Ig first induced in response to an antigen; it typically has lower affinity than other antibody isotypes produced later and is typically pentameric.

IgD (δ chain); this Ig is found in relatively high concentrations in umbilical cord blood, may be an early cell receptor for antigen, and is the main lymphocyte cell surface molecule.

The term "antibody" herein is used in the broadest sense and specifically covers monoclonal antibodies (including, but not limited to, full length monoclonal antibodies), polyclonal antibodies, multispecific antibodies (e.g., bispecific antibodies), and antibody fragments as long as they exhibit the desired biological activity.

"Antibody fragments" comprise a portion of a full length antibody, generally the antigen binding or variable (V) domain. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein specifically include "chimeric" antibodies (immunoglobulins), as well as fragments of such antibodies, as long as they exhibit the desired biological activity (U.S. Pat. No. 4,816,567; Morrison et al., *Proc. Natl. Acad. Sci. USA* 81:6851-6855 (1984); Oi et al., *Biotechnologies* 4(3):214-221 (1986); and Liu et al., *Proc. Natl. Acad. Sci. USA* 84:3439-43 (1987)).

"Humanized" or "CDR grafted" forms of non-human (e.g., murine) antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are also replaced by corresponding non-human residues (so called "back mutations"). Furthermore, humanized antibodies may be modified to comprise residues which are not found in the recipient antibody or in the donor antibody, in order to further improve antibody properties, such as affinity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); and Reichmann et al., *Nature* 332:323-329 (1988).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger el al., *Proc. Natl. Acad. Sci. USA* 90:6444-6448 (1993).

The expression "linear antibodies" when used throughout this application refers to the antibodies described in Zapata, et al. *Protein Eng.* 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies of the IgG, IgE, IgA, IgM, and IgD isotypes may have the same variable regions, i.e. the same antigen binding cavities, even though they differ in the constant region of their heavy chains. The constant regions of an immunoglobulin, e.g. antibody are not involved directly in binding the antibody to an antigen, but exhibit various effector functions, such as participation of the antibody in antibody-dependent cellular toxicity (ADCC).

Some of the main antibody isotypes (classes) are divided into further subclasses. IgG has four known subclasses: IgG1 (γ1), IgG2 (γ2), IgG3 (γ3), and IgG4 (γ4), while IgA has two known subclasses: IgA1 (α1) and IgA2 (α2).

The term "epitope" is used to refer to binding sites for (monoclonal or polyclonal) antibodies on protein antigens.

Antibodies which bind to domain 1 and/or 2 within the amino acid sequence of native sequence human CD22, or to essentially the same epitope(s) bound by any of the monoclonal antibodies specifically disclosed herein, such as HB22-7, HB22-23, and HB22-33, can be identified by "epitope mapping." There are many methods known in the art for mapping and characterizing the location of epitopes on proteins, including solving the crystal structure of an antibody-antigen, complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test, antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays (e.g. competition ELISA assays), which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term amino acid or amino acid residue, as used herein, refers to naturally occurring L amino acids or to D amino acids as described further below with respect to variants. The commonly used one- and three-letter abbreviations for amino acids are used herein (Bruce Alberts et al., *Molecular Biology of the Cell*, Garland Publishing, Inc., New York (3d ed. 1994)).

As used herein, the term "polypeptide" encompasses peptides and proteins, including fusion proteins.

"Sequence identity" is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values can be generated by the NCBI BLAST2.0 software as defined by Altschul et al., (1997), "Gapped BLAST and PSI-BLAST: a new generation of protein database search programs". *Nucleic Acids Res.*, 25:3389-3402. The parameters are set to default values, with the exception of the Penalty for mismatch, which is set to −1.

As used herein, "treatment" or "treating" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" or "treating" can also mean prolonging survival as compared to expected, survival if not receiving treatment. "Treatment" or "treating" is an intervention performed with the intention of preventing the development or altering the pathology of a disorder. Accordingly, "treatment" or "treating" refers to both therapeutic treatment and prophylactic or preventative measures. Those in need of treatment include those already with the disorder as well as those in which the disorder is to be prevented. With respect to autoimmune disease, the treatment results in some improvement, amelioration, stabilization and/or delay in at least one clinical symptom of the autoimmune disease in the subject. In the context of B cell malignancies, the treatment may reduce the number of malignant cells; reduce the tumor size; inhibit (slow down or stop) the spread of malignant cells, including infiltration into peripheral organs, e.g. soft tissue or bone; inhibit (slow down or stop) metastasis; inhibit tumor growth; provide relief from symptoms associated with a B cell malignancy; reduce mortality; improve quality of life, etc. Treatment with the antibodies herein may result in cytostatic and/or cytotoxic effects.

The term "B cell malignancy," and grammatical variants thereof are used in the broadest sense to refer to malignancies or neoplasms of B cells that typically arise in lymphoid tissues, such as bone marrow or lymph nodes, but may also arise in non-lymphoid tissues, such as thyroid, gastrointestinal tract, salivary gland and conjunctiva. The treatment methods of the present invention specifically concern CD22-positive B cell malignancies including, without limitation, B-cell subtype of non-Hodgkin's lymphoma, Burkitt's lymphoma, multiple myeloma, chronic lymphocytic leukemia, hairy cell leukemia, and prolymphocyte leukemia.

The term "autoimmune disease" refers to a condition which results from, or is aggravated by, the production of antibodies reactive with normal body tissues. It is a condition in which the immune system mistakenly attacks the body's own organs and tissues.

B. DETAILED DESCRIPTION

I. Antibodies

Blocking anti-CD22 monoclonal antibodies designated HB22-7, HB22-23, HB22-33, HB22-5, HB22-13, and HB22-196 are known, and have been disclosed in U.S. Pat. No. 5,484,892, Tuscano et al., *Eur. J. Immunol.* 26:1246 (1996), and Tuscano et al., *Blood* 94(4), 1382-1392 (1999). HB22-7 and HB22-23 are available from the American Type Culture Collection (ATCC), 10801 University Blvd. Manassas, Va. 20110, under Accession Nos, HB11347 and HB11349, respectively. The preparation of these antibodies is also described in Example 1 below. Epitope mapping of CD22 has shown that these blocking monoclonal antibodies bind to the first two Ig-like domains or to epitopes which are associated with the first two Ig-like domains of human CD22 (U.S. Pat. No. 5,484,892 and Tedder et al., *Annu. Rev. Immunol* 15:481-504 (1997)). The heavy and light chain variable region sequences of the antibodies are also disclosed in the present application.

The present invention is based. In part, on the unexpectedly superior properties of blocking anti-CD22 antibodies having the overall characteristics of HB22-7, HB22-23, HB22-33. HB22-5, HB22-13, and HB22-196 in the treatment of B-cell malignancies, based on results obtained in a xenograft model of B-cell type non-Hodgkin's lymphoma (NHL). The invention is further based on the use of blocking anti-CD22 antibodies having the overall characteristics of HB22-7, HB22-23, HB22-33, HB22-5, HB22-13, and HB22-196 in the treatment of autoimmune disease.

The anti-CD22 monoclonal antibodies can be made by any standard method known in the art, such as, for example, by the hyhridoma method (Koehler and Milstein, *Nature* 256:495-497 (1975); and Goding, *Monoclonal Antibodies: Principles and Practice*, pp. 59-103, (Academic Press, 1986)), or by recombinant, techniques, disclosed, for example, in U.S. Pat. No. 4,816,567, and by Wood et al., *Nature* 314:446-9 (1985).

It is now also possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 (1997)) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletions in the endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 $V_κ$ genes, Jκ segments and Cκ genes. The antibodies produced in these mice closely resemble those seen in humans in all respects, including gene rearrangement, assembly, and repertoire. The human antibodies are preferentially expressed over endogenous antibodies clue to deletions in the endogenous $J_H$ segment that prevents gene rearrangement in the murine locus.

Alternatively, phage display technology (McCafferty et al., *Nature* 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., *Current Opinion in Structural Biology* 3, 564-571 (1993), Several sources of V-gene segments can be used for phage display, Clackson el al., *Nature* 352, 624-628 (1991) isolated a diverse array of anti-oxazolone antibodies from a small random combinatorial library of V-genes derived from the spleens of immunized mice. A repertoire of V-genes from unimmunized human donors can be constructed and antibodies to a diverse array of antigens (including self-antigens) can be isolated, essentially following the techniques described by Marks et al., *J. Mol. Biol* 222, 581-597 (1991), or Griffith el al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783), In this method, the affinity of "primary" human antibodies obtained by phage display can be improved by sequentially replacing the heavy and light chain V-region genes with repertoires of naturally occurring variants (repertoires) of V-domain genes obtained from unimmunized donors. This technique allows the production of antibodies and antibody fragments with affinities in the nM range. A strategy for making very large phage antibody repertoires has been described by Waterhouse et al., *Nucl. Acids Res.* 21, 2265-2266 (1993), For further information concerning the production of monoclonal antibodies see also Goding, J. W., *Monoclonal Antibodies; Principles and Practice,* 3rd Edition, Academic Press, Inc., London, San Diego, 1996; Liddell and Weeks: *Antibody Technology: A Comprehensive Overview*, Bios Scientific Publishers: Oxford, UK, 1995; Breitling and Dubel: *Recombinant Antibodies.* John Wiley & Sons, New York, 1999; and *Phage Display: A Laboratory Manual.* Barbas et at., editors, Cold Springs Harbor Laboratory, Cold Spring Harbor, 2001.

Various techniques have been developed for the production of antibody fragments. Traditionally, these fragments were derived via proteolytic digestion of intact antibodies (see, e.g., Morimoto et al., *J. Biochem. Biophys.* Methods 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology* 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

Heteroconjugate antibodies, composed of two covalently joined, antibodies, are also within the scope of the present invention. Such antibodies have, for example, been proposed to target immune system cells to unwanted cells (U.S. Pat. No. 4,676,980), and for treatment of HIV infection (PCT application publication Nos. WO 91/00360 and WO 92/200373). Heteroconjugate antibodies may be made using any convenient cross-linking methods, using well known, commercially available cross-linking agents.

The antibodies of the present invention, whether rodent, human, or humanized may also have a further antigen-specificity, to form bispecific antibodies. The second binding specificity may be directed, for example, against a further B cell antigen, such as CD19, CD20, CD52, and other CD antigens expressed on B cells, especially antigens associated with the targeted B cell malignancy. For example, CD20 is known to be expressed in more than 90% of non-Hodgkin's lymphomas. An anti-CD20 antibody (Rituxan®, IDEC Pharmaceuticals) is in clinical use for the treatment of non-Hodgkin's lymphoma, CAMPATH-1H (anti-CD52w) is another antibody developed for treating B cell malignancies. Bispecific antibodies including a binding specificity to the CD20 or CD52 antigen are specifically included within the scope herein. Another B cell antigen to which the bispecific antibodies of the present invention can bind is HLA-DR10 (Lym-1), a known marker of non-Hodgkin's lymphoma. Bispecific antibodies can be generated to enhance tumor localization as well as to recruit and/or augment the tumor-specific immune response. Examples of other antigen targets include, CD3, CD28, and the Fc receptors (CD16, CD64 and CD89). Bispecific antibodies are expected to have enhanced cytotoxicity and, as a result, improved remission rate and survival.

Antibodies binding to essentially the same epitope as HB22-7, HB22-7, HB22-23, HB22-33, HB22-5, HB22-13, and/or HB22-196 can be identified by epitope mapping. The simplest way to determine whether two different antibodies recognize the same epitope is a competition binding assay. This method determines if the antibodies are able to block each other's binding to the antigen, and works for both conformational and linear epitopes. The competition binding assay can be configured in a large number of different formats using either labeled antigen or labeled antibody. In the most common version of this assay, the antigen is immobilized on a 96-well plate. The ability of unlabeled antibodies to block the binding of labeled antibodies to the antigen is then measured using radioactive or enzyme labels. For further details see, for example. Wegener et al., *J. Immunol,* 130:2308-2315 (1983); Wagener et al., *J. Immunol Methods,* 68:269-274 (1984); Kuroki et al., *Cancer Res.* 50:4872-4879 (1990); Kuroki et al., *Immunol. Invest.* 21:523-538 (1992); Kuroki et al., *Hybridoma* 11:391-407 (1992), and Using Antibodies: A Laboratory Manual, Ed Harlow and David Lane editors. Cold Springs Harbor Laboratory Press, Cold Springs Harbor, N.Y., 1999, pp. 386-389.

Alternatively, or in addition, epitope mapping can be performed by using a technique based on fragmentation of the antigen to which the antibody binds, either randomly or by specific genetic construction, and determining the reactivity of the fragments obtained with the antibody. Fragmentation can also be performed on the nucleic acid level, for example by PGR technique, followed by transcription and translation into protein in vitro in the presence of radioactive amino acids. For further details see, for example, Harlow and Lane, supra, pp. 390-392.

According to a further method of epitope mapping, a set of overlapping peptides is synthesized, each corresponding to a small linear segment of the protein antigen, and arrayed on a solid phase. The panel of peptides is then probed with the test antibody, and bound antibody is detected using an enzyme-labeled secondary antibody. (Harlow and Lane, supra, pp. 393-396.)

An additional method well known in the art for epitope mapping is antibody selection from a random synthetic or a phage display peptide library. Phage display libraries are constructed by cloning complex mixtures of peptide-encoding oligonucleotides into the amino terminus of the minor coat protein gene of the fl-type ssDNA phage. Such phage display libraries are commercially available, for example, from New England Biolabs. The libraries are amplified as stocks, and then an aliquot sufficient to represent multiple copies of each independent clone is mixed with the antibody of interest. Antibody-bound phage are collected by a procedure called "biopanning," and unbound phage are removed. The bound phage are eluted and used to infect bacteria, and the selected stock is amplified. Individual plaques of the final selected stock are growth and checked for specific antibody reactivity, e.g. by ELISA, and the DNA around the insert site is sequenced. Analysis of the sequence encoding the peptide to which the antibody binds defines the specificity of the antibody. For further details see, e.g. Smith and Scott, Methods Enzymol. 217:228-257 (1993), and Harlow and Lane, supra, pp. 397-398.

Non-human (rodent) antibodies can be further modified to make them more suitable for human clinical application. Chimeric antibodies are produced with mouse variable region gene segments of desired specificity spliced into human constant domain gene segments (see, e.g. U.S. Pat. No. 4,816, 567).

Non-human (rodent) antibodies can also be humanized in order to avoid issues of antigenicity when using the antibodies in human therapy. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Despite the relatively straightforward nature of antibody humanization, simple grafting of the rodent CDR's into human frameworks (FR) does not always reconstitute the binding affinity and specificity of the original rodent monoclonal antibody. Properties of a humanized antibody can be improved by suitable design, including, for example, substitution of residues from the rodent antibody into the human framework (backmutations). The positions for such backmutations can be determined by sequence and structural analysis, or by analysis of the variable regions' three-dimensional model. In addition, phage display libraries can be used to vary amino acids at chosen positions within the antibody sequence. The properties of a humanized antibody are also affected by the choice of the human framework. Early experiments used a limited subset of well-characterized human monoclonal antibodies, irrespective of the sequence identity to the rodent monoclonal antibody (the so-called fixed frameworks approach). More recently, some groups use variable regions with high amino acid sequence identity to the rodent variable regions (homology matching or best-fit method). According to another approach, consensus or germline sequences are used, or fragments of the framework sequences within each light or heavy chain variable region are selected from several different human monoclonal antibodies.

Amino acid variants of antibodies prepared by any technique discussed above or otherwise available can be prepared by introducing appropriate nucleotide changes into the anti-CD22 DNA, or, for example, by peptide synthesis. The amino acid changes also may alter post-translational processes of the humanized or variant anti-CD22 antibody, such as changing the number or position of glycosylation sites.

Antibodies are glycosylated at conserved positions in their constant regions (Jefferis and Lund, Chem. Immunol. 65; 111-128 (1997); Wright and Morrison, TibTECH 15:26-32 (1997)). The oligosaccharide side chains of the immunoglobulins affect the protein's function (Boyd et al., Mol. Immunol. 32:1311-1318 (1996); Wittwe and Howard, Biochem, 29:4175-4180 (1990)), and the intramolecular interaction between portions of the glycoprotein which can affect the conformation and presented three-dimensional surface of the glycoprotein (Jefferis and Lund, supra; Wyss and Wagner, Current Opin. Biotech. 7:409-416 (1996)), Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., Nature Med. 1:237-243 (1995)). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., Mol. Immunol. 32:1311-1318 (1996)), while selective removal of sialic acid residues using neuraminidase resulted in no loss of CMCL. Clycosylation of antibodies has also been reported to affect antibody-dependent cellular cytotoxicity (ADCC). In particular, CHO cells with tetracycline-regulated expression of β(1,4)-N-acetylglucosaminyltransferase III (Gn TIII), a glyeosyltransferase catalyzing formation of bisecting GlcNAc, was reported to have improved ADCC activity (Umana et al., Mature Biotech. 17:176-180 (1999)), Glycosylation variants of antibodies can be prepared by modifying the glycosylation sites in the underlying nucleotide sequence. In addition, the glycosylation of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., J. Biol. Chem. 272:9062-9070 (1997)). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510, 261 and 5,278,299). Glycosylation, or certain types of glycosylation, can be enzymatically removed from the glycoprotein, for example using endoglycosidase H (Endo H). In addition, the recombinant host cell can be genetically engineered, e.g. made defective in processing certain types of polysaccharides. These and similar techniques are well known in the art.

The antibodies of the present invention may also be used by the antibody-directed enzyme prodrug therapy (ADEPT). ADEPT is a technology that utilizes the specificity of monoclonal antibodies targeting tumor antigens to target catalytic enzymes to the surface of cancer cells. There, the enzymes are in position to activate prodrug forms (e.g., a peptidyl chemotherapeutic agent, see WO81/01145) of anti-cancer drugs to their fully active form. See, for example, WO 88/07378 and U.S. Pat. No. 4,975,278.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used, to convert the prodrugs of the invention into free active drugs (see, e.g., Massey, *Nature* 328:457-458 (1987)). Antibody-abzyme conjugates can be prepared as described herein for delivery of the abzyme to a tumor cell population.

Immunoconjugates of the antibodies herein are also specifically encompassed by this invention. Immunoconjugates comprise an antibody conjugated to a cytotoxic agent, such as chemotherapeutic agent, a toxin, or a radioisotope.

Specifically, the efficacy of the anti-CD22 antibodies herein can be further enhanced by conjugation to a cytotoxic radioisotope, to allow targeting a radiotherapy specifically to target sites (radioimmunotherapy). Suitable radioisotopes include, for example, $I^{131}$ and $Y^{90}$, both used in clinical practice. Other suitable radioisotopes include, without limitation, $In^{111}$, $Cu^{67}$, $I^{131}$, $As^{211}$, $Bi^{212}$, $Bi^{213}$, and $Re^{186}$.

Chemotherapeutic agents useful in the generation of immunoconjugates include, for example, adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards.

Toxins to be used in the immunoconjugates herein include, for example, diphtheria A chain, exotoxin A chain, ricin A chain, enomycin, and tricothecenes. Specifically included are antibody-maytansinoid and antibody-calicheamicin conjugates. Immunoconjugates containing maytansinoids are disclosed, for example, in U.S. Pat. Nos. 5,208,020, 5,416,020 and European Patent EP 0 425 235. See also Liu et al., *Proc. Natl. Acad. Sci. USA* 93:8618-8623 (1996). Antibody-calicheamicin conjugates are disclosed, e.g. in U.S. Pat. Nos. 5,712,374; 5,714,586; 5,739,116; 5,767,285; 5,770,701; 5,770,710; 5,773,001; and 5,877,296.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidohenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such, as 1,5-difluoro-2,4-dinitrobenzene). For example, a ricin immunotoxin can be prepared as described in Vitetta et al., *Science,* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11.026.

Covalent modifications of the anti-CD22 antibodies are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. A preferred type of covalent modification of the antibodies comprises linking the antibodies to one of a variety of nonproteinaceous polymers, e.g., polyethylene glycol, polypropylene glycol, or polyoxyalkylenes, in the manner well known in the art.

2. Pharmaceutical Formulations and Treatment Methods

B-cell type Non-Hodgkin's Lymphoma is a term that is used to encompass a large group (over 29 types) of lymphomas caused by malignant (cancerous) B cell lymphocytes, and represents a large subset of the known types of lymphoma. B-cells are known to undergo many changes in their life cycle dependent on complex intracellular signaling processes, and apparently different types of B-cell malignancies can occur at different stages of the life cycle of B-cells. At the stem cell stage, acute lymphocytic leukemia (ALL) or lymphoblastic lymphoma/leukemia can typically develop. Precursor B-cells can develop precursor B lymphoblastic lymphoma/leukemia. Typical malignancies of immature B-cells include small non-cleaved cell lymphoma and possibly Burkitt's/non-Burkitt's lymphoma. B cells before antigen exposure typically develop chronic lymphocytic leukemia (CLL) or small lymphocytic lymphoma, while after antigen exposure typically follicular lymphomas, large cell lymphoma and immunoblastic lymphoma are observed. There are also classification systems that characterize B-cell lymphomas by the rate of growth distinguishing aggressive (fast growing) and indolent (slow growing) lymphomas. For example, Burkitt's/non-Burkitt's lymphoma and LCL lymphoma belong in the aggressive group, while indolent lymphomas include follicular center cell lymphomas (FCCL), follicular large cell lymphomas, and follicular small cleaved cell lymphomas.

Non-Hodgkin's Lymphomas are also characterized by the stage of development. Stage I: cancer is found in only one lymph node area, or in only one area or organ outside the lymph nodes. Stage II: (1) Cancer is found in two or more lymph node areas on the same side of the diaphragm (the thin muscle under the lungs that helps breathing), or, (2) cancer is found in only one area or organ outside the lymph nodes and in the lymph nodes around it, or (3) other lymph node areas on the same side of the diaphragm may also have cancer. Stage III: Cancer is found in lymph node areas on both sides of the diaphragm. The cancer may also have spread to an area or organ near the lymph node areas and/or to the spleen. Stage IV: (1) Cancer has spread to more than one organ or organs outside the lymph system; cancer cells may or may not be found in the lymph nodes near these organs, or (2) cancer has spread to only one organ outside the lymph system, but lymph nodes far away from that organ are involved.

Current treatment options of B-cell malignancies, including non-Hodgkin's lymphomas depend on the type and stage of malignancy. Typical treatment regimens include radiation therapy, also referred to as external beam therapy, chemotherapy, immunotherapy, and combinations of these approaches. One promising approach is radioimmunotherapy (RIT). With external beam therapy, a limited area of the body is irradiated. With chemotherapy, the treatment is systemic, and often adversely affects normal cells, causing severe toxic side-effects. Targeted RIT is an approach in which a B-cell specific antibody delivers a toxic substance to the site of tumor. The therapeutic potential of RIT in patients with B-cell NHL has been shown using different targets, including CD20, CD19, CD22, and HLA-DR10 (Lym-1). More recently, combined modality therapy (CMT) has become an increasingly frequent maneuver for the treatment of solid tumors, and includes radiosensitization of cancer cells by drugs, and the direct cytotoxic effect of chemotherapy. The most common chemotherapy regiment for treating NHL is Cyclophosphamide-Hydroxydoxorubin-Oncovin (vincristine)-Prednisone (CHOP) combination therapy. A randomized study of aggressive, but early stage NHL showed superior results with CHOP plus involved field radiation over treatment with CHOP alone. Despite its promise, the disadvantage of treatments involving external beam radiation is that external beam radiation can only be delivered in high doses to a limited region of the body, while NHL is mostly widespread. Accordingly, CMT has proven clinically useful for locally advanced malignancies.

Another current approach is combined modality radioimmunotherapy (CMRIT), which pairs the specific delivery of systemic radiation (e.g. $^{90}$Y-DOTA-peptide-Lym-1) to NHL with the systemic radiation sensitizing effects of an additional chemotherapeutic agent. Because in CMRIT radiation is delivered continuously, cancer cells that are hypoxic may re-oxygenate, or pass through the radiosensitive: $G_2$/M phase of the cell cycle during the course of treatment, making cure more likely. In addition, CMRIT provides specificity first, by the specific targeting of NHL by Lym-1, and second by timing. This allows the radiation sensitizer to potentially synergism only at the sites targeted by RIT, thus maximizing efficacy and minimizing toxicity. Several previous xenograft studies have demonstrated improved synergy when the radiation synthesizer (Taxol) was given 24-48 hours after RIT.

Although CMRIT is currently viewed as the most advanced therapeutic approach for the treatment of NHL, the antibodies of the present invention alone have been demonstrated to provide superior results both in terms of tumor volume reduction, cure rate and overall survival, when tested in the well accepted Raji and Ramos lymphoma xenograft models.

Autoimmune diseases are caused by a breakdown in self-tolerance leading to subsequent immune responses against self, including the production of autoantibodies and deposition of immunoglobulin in affected tissues. Autoantibodies form immune complexes that promote complement and Fc-receptor mediated tissue inflammation and destruction. Since B cells are the source of autoantibodies, they afford a rational target for treatment of these types of immune-mediated diseases. B cells also can present antigen and regulate the development of effector T cells. The pathologic mechanisms of these diseases are complex and often involve a combination of humoral and cellular immune mechanisms.

Most autoimmune diseases result from, or are aggravated by, the production of antibodies reactive with normal body tissues. Antibodies are produced by B cells following antigen stimulation and activation. Therefore, blocking CD22 function can inhibit the production of antibodies, including autoreactive antibodies. More than 80 autoimmune diseases have been identified. Autoimmune diseases, their etiology and treatment are discussed extensively in the *Autoimmune Diseases Research Plan* published by the Autoimmune Diseases Coordinating Committee of the National Institutes of Health. Autoimmune diseases that can be treated according to the present invention include, but are not limited to immune complex disorders such as those that result in glomerulonephritis, Goodspature's syndrome, necrotizing vasculitis, lymphadenitis, peri-arteritis nodosa and systemic lupus erythematosis. Other illustrative autoimmune diseases include but are not limited to rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-assoeiated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroiditis, and cardiomyopathy. Other diseases associated with antibody production include, but are not limited to multiple sclerosis, atopic dermatitis, thrombocytopenic purpura, agranulocytosis, autoimmune hemolytic anemias, immune reactions against foreign antigens such as fetal A-B-O blood groups during pregnancy, myasthenia gravis. Type I diabetes. Graves' disease, and allergic responses. The methods of the invention may be used to treat any other disorder or condition in which B cells or antibodies are implicated including, for example, transplant rejection.

The anti-CD22 antibodies herein are typically administered in the form of pharmaceutical formulations well known to all pharmaceutical chemists. See, e.g. *Remington's Pharmaceutical Sciences*, (15th Edition, Mack Publishing Company, Easton, Pa. (1975)), particularly Chapter 87, by Blaug, Seymour. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. A typical dosage form is a sterile, isotonic, water-based solution suitable for administration by the intravenous (i.v.) route. The concentration of the antibodies of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such, as an antibody, or with other therapeutic or immunogenic compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream, A variety of methods are available for preparing liposomes, as described in, e.g., Szoka el al. *Ann. Rev. Biophys. Bioeng.* 9:467 (1980), U.S. Pat. Nos. 4,235,871, 4,501,728, 4,837,028, and 5,019,369.

The antibodies of the present invention can be administered alone or in combination with other therapeutic regimens. For example, in the case of B-cell malignancies, such regimes or therapies include chemotherapy, radioimmunotherapy (RIT), chemotherapy and external beam radiation (combined modality therapy, CMT), combined modality radioimmunotherapy (CMRIT), or cytokines alone or in combination, etc. Thus, the anti-CD22 antibodies of the present invention can be combined with CHOP (Cyclophosphamide-Hydroxydoxorubicin-Oncovin (vincristine)-Prednisolone), the most common chemotherapy regimen for treating non-Hodgkin's lymphoma. In addition, the anti-CD22 antibodies herein may be administered in combination with other antibodies, including anti-CD 19, anti-CD2 and other anti-CD22 antibodies, such as LymphoCide™ (Immunomedics, Inc.) or LymphoCide Y-90. See, for example, Stein et al., *Drugs of the Future* 18:997-1004 (1993); Behr et al., *Clinical Cancer Research* 5:3304s-33314s, 1999 (suppl.); Juweid et al., *Cancer Res.* 55:5899s-5907s, 1995; Behr et al., *Tumor Targeting* 3:32-40 (1998), and U.S. Pat. Nos. 6,183,744, 6,187,287, and 6,254,868.

The inventive treatments may also be employed in combination with other therapies for autoimmune disorders. In particular embodiments, the subject is treated with the antibodies of the invention as well as with an anti-CD20 antibody (e.g., Rituxan®, IDEC Pharmaceuticals) and/or an anti-inflammatory drug (e.g., corticosteroids). In certain embodiments, the treatment is unaccompanied by any other treatment for the autoimmune disease.

In particular embodiments, the patients to be treated in accordance with the present invention will have CD22 expressed on their malignant B cells. The presence of the CD22 antigen can be confirmed by standard techniques, such as immunohistochemistry, FACS, binding assay with labeled (e.g. radiolabeled) anti-CD22 antibody.

The antibody compositions of the invention can be administered using conventional modes of administration including, but not limited to, intravenous, infra-arterial, intraperitoneal, oral, intralymphatic, intramuscular, intradermal, subcutaneous, and intranasal administration. In particular embodiments, the route of administration is via bolus or continuous infusion over a period of time, such as continuous or bolus infusion, once or twice a week. In other particular embodiments, the route of administration is by subcutaneous injection. The dosage depends on the nature, form, and stage of the targeted B cell malignancy or autoimmune disease, the patient's sex, age, condition, prior treatment history, other treatments used, and other factors typically considered by a skilled physician. For example, non-Hodgkin's lymphoma patients or patients with autoimmune disease may receive from, about 50 to about 1500 mg/m$^2$/week, specifically from about 100 to about 1000 mg/m$^2$/week, more specifically from about 150 to about 500 mg/m$^2$/week of an anti-CD22 antibody as described herein.

The patients can be monitored by standard techniques known in the art to follow clinical indicia of B-cell malignancy or the particular autoimmune disease. For example, in the case of B-cell malignancy, tumor regression (e.g. tumor size in the case of solid tumors), the phenotype of circulating B-cells or of biopsied tissues using anti-CD22 antibodies can be monitored.

While the invention has been discussed with reference to human therapy, it will be understood that the antibodies of the present invention also find use in veterinary medicine. For example, feline malignant lymphoma occurs frequently in domestic cats, and shows similar characteristics to human non-Hodgkin's lymphoma (Bertone et al., *Am. J. Epidemiol.* 156:268-73 (2002)). Similarly, dogs are known to develop a variety of lymphomas. Accordingly, the antibodies herein can be used to treat feline and canine malignant lymphoma. Animal models of autoimmune disease are also known in the art. Dosages, and routes of administration depend on the animal species to be treated, and their determination is well within the skill of a veterinary of ordinary skill.

Further details of the invention are provided in the following non-limiting examples.

EXAMPLES

Commercially available reagents referred to in the examples were used according to manufacturer's instructions unless otherwise indicated. In addition to production as disclosed in the following examples, hybridoma producing monoclonal antibody HB22-7 (ATCC Accession No. HB11347) may be obtained from the American Type Culture Collection, Manassas, Va.

Example 1

Production of Anti-CD22 Monoclonal Antibodies

Monoclonal antibodies (mAbs) HB22-7 (IgG2b), HB22-23 (IgG2a), HB22-33 (IgM), HB22-5 (IgG2a), HB22-13 (IgG2a), HB22-22 (IgA), and HB22-196 were produced according to the method of Engel et al., *J Immunol* 15:4710 (1993) and U.S. Pat. No. 5,484,892. See, also Tuscano et al, *Blood* 94:1382-1392 (1999). However, other methods may be used. Briefly, the HB22 mAbs were produced via hybridoma techniques using a mouse pre-B cell line 300.19, stably transfected with full length CD22 cDNA, as the immunogen. More specifically, thirty-three mAbs reactive with CD22 were generated by the fusion of NS-1 myeloma cell with spleen cells from Balb/c mice immunized three times with a mouse pre-B cell line, 300.19, stably transfected with a full-length CD22 cDNA. Hybridomas producing mAb reactive with mouse L cells transfected with CD22 cDNA, but not with untransfected cells, were cloned twice and used to generate supernatant or ascites fluid. mAb isotypes were determined using the Mouse Monoclonal Antibody Isotyping Kit (Amersham, Arlington Heights, Ill.). IgGmAb were purified using the Affi-Gel Protein A MAPS II Kit (Bio-Rad, Richmond, Calif.). The HB22-33 mAb (IgM) containing euglobulin fraction of ascites fluid was precipitated by extensive dialysis against distilled water and was shown to be essentially pure mAb by SDS-PAGE analysis. As disclosed in Table II of U.S. Pat. No. 5,484,892, mAbs HB22-7, HB22-22, HB22-23, and HB22-33 completely blocked (80-100%) the binding of Daudi, Raji and Jurkat cells to CD22 transfected COS cells. mAbs HB22-5, HB22-13, HB22-24, and HB22-28 partially blocked adhesion (20-80%).

Figure 3:
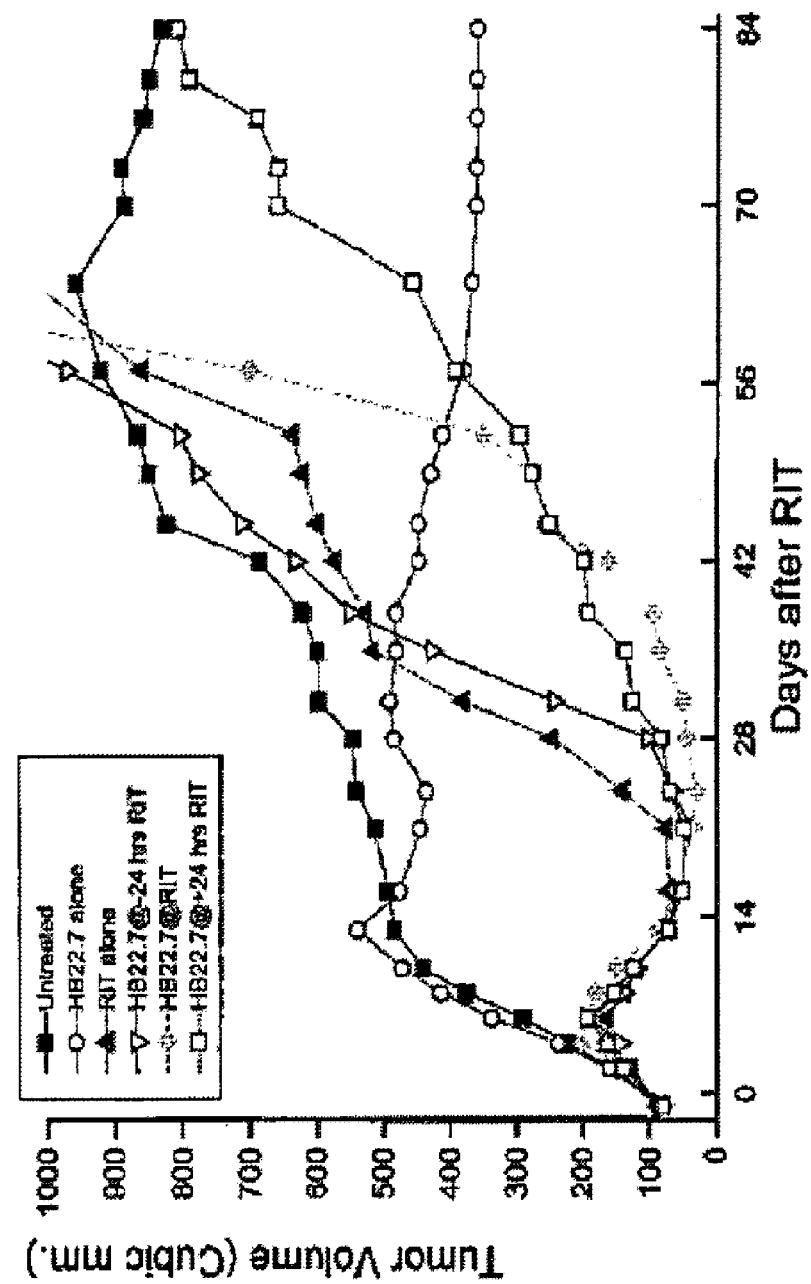
FIG. 3, The temporal assessment of tumor volume in Raji-xenografted mice that were untreated or treated with 125 μCi $^{90}$Y-DOTA-peptide-Lym-1 (RIT) alone, anti-CD22 alone (HB22-7), or three different sequences of RIT and HB22-7 (CMRIT) in trial 081500. Tumor volume was assessed three times per week. Mouse numbers for each treatment group are tabulated (Table 2).

The region(s) on CD22 that mediates ligand binding was characterized by mAb cross-inhibition studies using the "Workshop" CD22-blocking mAb and a panel, of mAb that identify five different epitopes on CD22 (epitopes A, B, C, D, and E (Schwartz-Albiez et al., "The carbohydrate moiety of the CD22 antigen can be modulated by inhibitors of the glycosylation pathway." The binding specificities of the Workshop mAb are depicted pietorially in FIG. 3. In Leukocyte Typing IV. White Cell Differentiation Antigens, Knapp et al., eds., Oxford University Press, Oxford, p. 65 (1989)). It has been found that three of the monoclonal antibodies herein, HB22-7, HB22-22, and HB22-23, bind to very close or the same epitopes on CD22. Results of the epitope-mapping of these and other blocking antibodies are disclosed in Tedder et al., *Annu. Rev. Immunol* 15:481-504 (1997). Unlike other anti-CD22 antibodies proposed for therapy, the blocking antibodies of the present invention bind to an epitope within the first two Ig-like domains of the hCD22 amino acid sequence.

Example 2

Raji and Ramos Lymphoma Xenograft Trials

This example describes the results from our independent Raji and Ramos lymphoma xenograft trials. Nude mice xenografts are important tools for preclinical evaluations. Nude mice bearing human non-Hodgkin's lymphoma (NHL) xenografts utilizing the lymphoma cell, lines Raji and Ramos have proven utility for evaluating efficacy for treatment of NHL. (Buchsbaum et al., *Cancer Res.* 52(23):6476-6481 (1992) and Flavell et al., *Cancer Res.* 57:4824-4829 (1997)).

Materials and Methods

Reagents.

Carrier-free $^{90}$Y (Pacific Northwest National Laboratory, Richland, Wash.) and $^{111}$In (Nordion, Kanata, Ontario, Canada) were purchased as chlorides in dilute HCl. Lym-1 (Techniclone, Inc Tustin, Calif.) is an $IgG_{2a}$ mAb generated in mice immunized with human Burkitt's lymphoma cell nuclei. Lym-1 recognizes a cell surface 31-35 kD antigen on malignant B cells, and reacts with greater than 80% of human B cell NHL. Lym-1 purity was assessed according to the specifications that required greater than 95% pure monomelic IgG by polyacrylamide gel electrophoresis. $^{90}$Y-DOTA-peptide-Lym-1 was prepared as previously described (O'Donnell et al., *Cancer. Biother. Radiopharm.* 13:251-361 (1998)). Assessment by HPLC, TLC, and cellulose acetate electrophoresis revealed that $^{90}$Y-DOTA-peptide-Lym-1 was prepared to 98% radiochemical purity with less than 5% aggregate content.

The anti-CD22 mAb, HB22-7, was prepared as previously described. (Tuscano et al., *Blood* 94:1382-1392 (1999)), using a Protein A Sepharose Fast Flow column (Pharmacia). HB22-7 purity was determined by HPLC and flow cytometry, and found to be >95% pure. Physiologic properties were determined by flow cytometric-based analysis of apoptotic induction (Apo-Tag, Pharmacia) and found to be consistent with previous published results (Tuscano et al., supra), Endotoxin removal was achieved using an ActiClean ETOX column. (Sterogene), with final endotoxin levels determined to be <0.15 Endotoxin Units (EU)/mg mAb (BioWhitaker). The Lym-1 and HB22-7 mAbs met MAP (mouse antibody production) guidelines for murine, viral, mycoplasma, fungal, and bacterial contamination, as well as endotoxin, pyrogen and DNA content and general safety testing in animals.

Cell lines and Scatchard Analysis.

Raji and Ramos Burkitt lymphoma, cell lines were purchased from American Type Culture Collection (ATCC, Manassas, Va.). Both cell lines stained for CD22 expression by flow cytometric methods utilizing the HB22-7 mAb, as described previously (Tuscano et al., supra). The cell lines were maintained in RPMI 1640 supplemented with 10% fetal calf serum at 0.5 times. $10^6$ cells/ml. A Scatchard analysis using Raji and Ramos cells was performed as described previously (Scatchard, G., *Ann. of NY Acad Sci.* 51:660 (1947)). Briefly, HB22-7 was labeled with $^{125}$I by the chloramine T method (specific activity of 1.1 µCi/1 g). A competitive binding assay was performed utilizing serially diluted, unlabeled HB22-7.

Mouse Studies.

Female athymic BALB/c nu/nu mice (Harlan Sprague-Dawley), 7-9 weeks of age were maintained according to University of California, Davis animal care guidelines on a normal diet ad libitum and under pathogen-free conditions. Five mice were housed per cage. Raji or Ramos cells were harvested in logarithmic growth phase; 2.5-5.0.times. $10^6$ cells were injected subcutaneously into both sides of the abdomen of each mouse. Studies were initiated 3 weeks after implantation, when tumors were 28-328 $mm^3$. Groups consisted of untreated, 125 µCi of RIT alone, 1.4 mg of HB22-7 alone, or the combination of RIT and HB22-7, with HB22-7 being administered 24 hours prior, simultaneously, or 24 hours after RIT. To minimize ambient radiation, bedding was changed daily for 1 week after treatment with $^{90}$Y-DOTA-peptide-Lym-1, and twice weekly thereafter.

Tumoricidal Effect.

Tumor volume was calculated as described by the formula for hemiellipsoids (DeNardo et al., *Clin. Cancer Res.* 3:71-79 (1997)). Initial tumor volume was defined as the volume on the day prior to treatment. Mean tumor volume was calculated for each group on each day of measurement; tumors that had completely regressed were considered to have a volume of zero. Tumor responses were categorized as follows: C, cure (tumor disappeared and did not regrow by the end of the 84 day study); CR, complete regression (tumor disappeared for at least 7 days, but later regrew); PR, partial regression (tumor volume decreased by 50% or more for at least 7 days, then regrew).

Statistical Analysis.

Differences in response among treatment groups were evaluated using the Kruskall Walis rank sum test with the response ordered as none, PR, CR, and Cure. Survival time was also evaluated using the Kruskall Walis test. Tumor volume was compared at 3 time points: month 1 (day 26-29), month 2 (day 54-57), and at the end of the study (day 84). If an animal was sacrificed due to tumor-related, causes, the last volume was carried forward and used in the analysis of later time points. Analysis of variance was used to test for differences among treatment groups. P values are two-tailed and represent the nominal p-values. Protection for multiple comparisons is provided by testing only within subsets of groups found to be statistically significantly different.

Results

Scatchard Analysis

Scatchard analysis was utilized to assess the binding affinity of HB22-7 and the number of CD22 receptors on Ramos and Raji cells. The cells were assayed for maximum, binding percentage (Bmax), disassociation constant (Ka) and number of antibodies bound per cell. The results shown in Table 1 are the average of two experiments.

TABLE 1

1. PARAMETER

|  | Cell Lines | |
| --- | --- | --- |
| Cell line | Raji | Ramos |
| Bmax | 53.5 ± 0.9% | 21.0 ± 1.3% |
| $R^2$ | 0.954 | 0.926 |
| Ka | 1.3 ± 0.08 × 10$^9$ | 5.95 ± 1.0 × 10$^8$ |
| Antibody/cell | 118,000 | 43,000 |

The Scatchard analysis (Table 1) revealed a nearly 2.5 fold increase in the number of HB-22-7 antibodies bound per cell, and Bmax, and a 2 fold increase in Ka for Raji cells versus Ramos cells, respectively.

Whole Body Autoradiography

In order to assess HB22-7-specific tumor targeting, whole body autoradiography of tumor-bearing nude mice injected with $^{111}$In-2IT-BAD-anti-CD22 (HB22-7) was performed. Forty eight hours after injection mice were sacrificed, sectioned and autoradiographed (FIG. 2), as previously described (DeNardo et al., Cancer 3:71-79 (1997)). Autoradiography revealed intense tumor localization in the Raji-tumored mice and moderate localization in the Ramos-tumored mice. This targeting study is consistent with the Scatchard analysis that revealed less HB22-7 bound per Ramos cells as compared to Raji. However the rapid growth of Ramos tumors, and likely central necrosis, may also contribute to the apparent inferior targeting of Ramos.

Efficacy of RIT and CMRIT

The initial trial (081500) utilized 125 µCi of $^{90}$Y-DOTA-peptide-Lym-1 alone or in combination with HB22-7 (1.4 mg) given either 24 hours prior, simultaneously, or 24 hours after RIT, (FIG. 3). In this trial there were 5 mice per group with the exception of the group treated with RIT alone, which had 9 mice and 5 untreated controls (mouse numbers are tabulated, in Table 2).

TABLE 2

| | Treatment Groups | | | | | |
| --- | --- | --- | --- | --- | --- | --- |
| Trial | No Tx | HB22-7 | RIT | −24 | @RIT | +24 |
| 081500 | 5 | 4 | 9 | 5 | 5 | 5 |
| 101600 | 5 | 6 | 5 | 5 | 3 | 5 |
| 011601 | — | 5 | 4 | — | 9 | 7 |
| 032701 | — | 5 | 2 | — | 3 | 12 |
| 052401 | 3 | — | 3 | — | — | — |
| 060401 | 5 | 5 | — | — | — | — |
| 071701 | 7 | 5 | — | — | — | 4 |
| 092101 | 4 | — | — | — | — | — |
| 102401 | 13 | — | — | — | — | — |
| Total | 42 | 30 | 23 | 10 | 20 | 33 |

As predicted from similar Raji xenograft studies with $^{90}$Y-2IT-BAD-Lym-1, RIT alone resulted in maximal mean tumor volume reduction by day 21, with increasing tumor volume thereafter. Xenografts treated with $^{90}$Y-2IT-BAD-Lym-1 (RIT) and HB22-7 (CMRIT) demonstrated greater and more sustained mean tumor volume reduction, which was greatest when HB22-7 was administered simultaneously, and 24 hours after RIT. Surprisingly, HB22-7 administered alone resulted in stabilization of mean tumor volume by 2-3 weeks, then a gradual and sustained tumor volume reduction.

Figure 4:
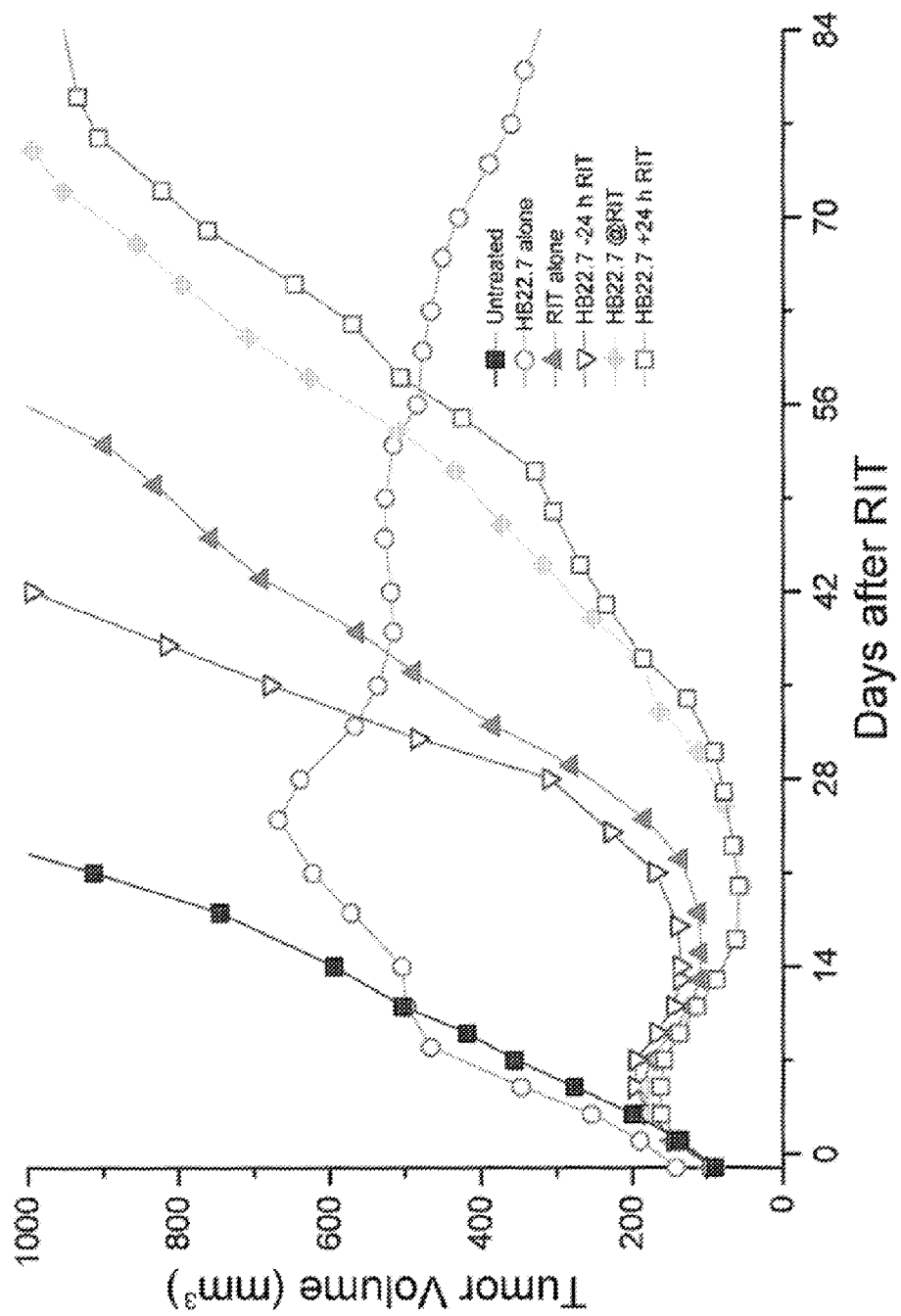
FIG. 4. Summary analysis of tumor volume observed in all independent xenograft trials. The trials were conducted as described in FIG. 2. Mouse numbers for each trial are tabulated (Table 2).

Several additional replicate trials were conducted with highly reproducible results (Table 2). The data from all trials were compiled and, when compared graphically, revealed results highly consistent with the initial study, (FIG. 4). The initial tumor volume reductions were again greatest at approximately day 21 when HB22-7 was administered simultaneously and 24 hours after RIT. In mice treated with HB22-7 alone, the stabilization in tumor growth that began 2 weeks after treatment followed by gradual sustained tumor volume reduction was also replicated in all subsequent trials. Using analysis of variance, when examining all treatment groups at day 30 the differences were highly significant (p<0.001). While analysis of volume reduction in all treatment groups at day 60 did not demonstrate significant differences (p=0.39), the differences at day 84 again were significant (p=0.003). The results observed graphically revealed that the difference in volume reduction in the RIT/CMRIT groups was highly reproducible and different from HB22-7 alone and untreated control, however, comparison of volume reduction only in only RIT treatment groups (including CMRIT) at all time points assessed (day 30, 60, and 84) did not reveal significant differences (p>0.5). Additional CMRIT trials were done with HB22-7 being administered 48 and 72 hours after RIT. The extended interval between the administration of RIT and HB22-7 did not result in improved tumor volume reduction when compared to trials in which HB22-7 was given simultaneously and 24 hours after RIT (data not shown).

Figure 5:
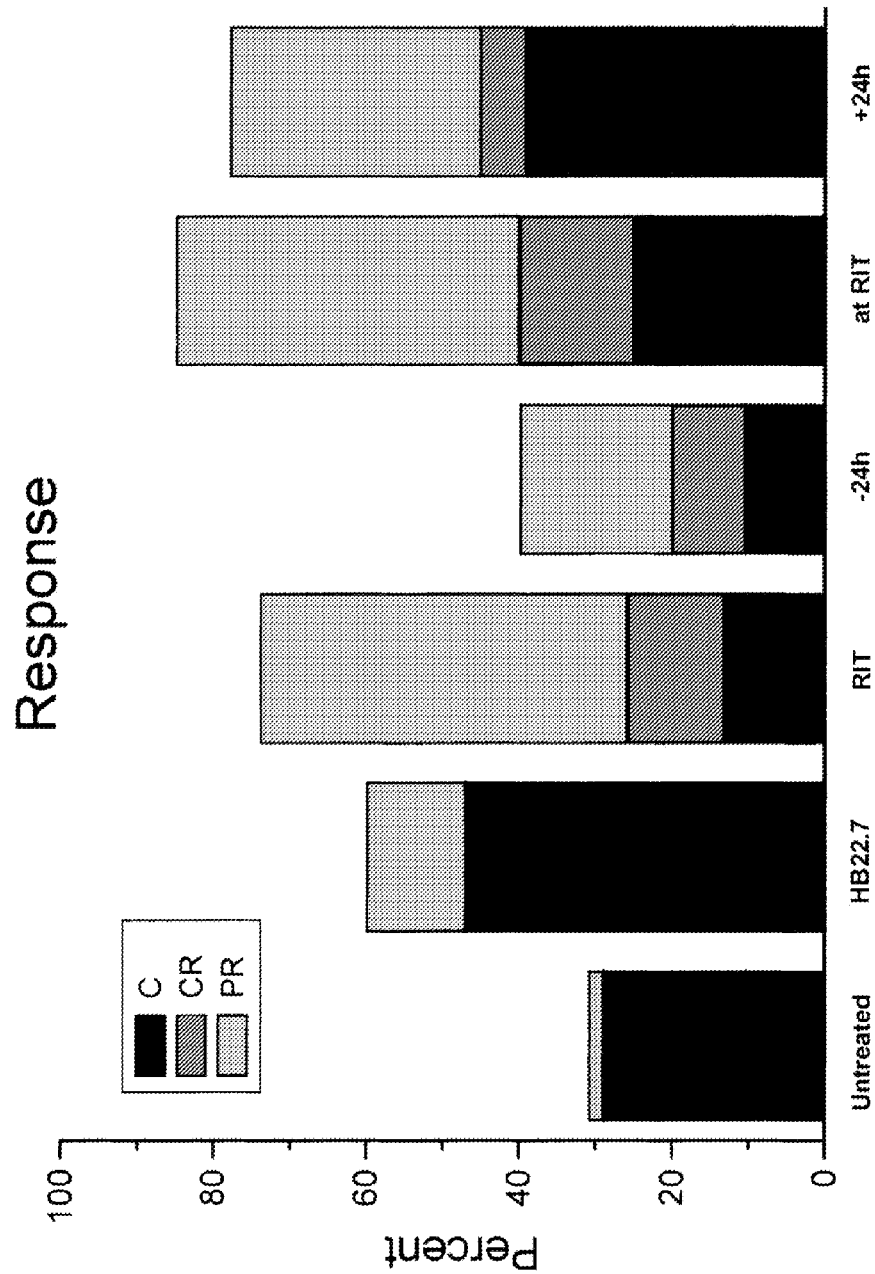
FIG. 5. The response and cure rate for Raji-xenografted mice that were treated as described in FIG. 2. The tumor responses were categorized as follows: C, cure (tumor disappeared and did not regrow by the end of the 84-day study); CR, complete regression (tumor disappeared for at least 7 days but later regrew); PR, partial regression (tumor volume decreased by 50% or more for at least 7 days, then regrew). The data represents results of all independent trials.

Response and cure rates were consistent with the effects of treatment on tumor volume, (FIG. 5). Treatment with $^{90}$Y-DOTA-peptide-Lym-1 alone produced 48% PR, 13% CR, and a 13% cure rate. In the CMRIT groups, the overall response rate was maximized when HB22-7 and RIT were administered simultaneously generating 45% PR, 15% CR and 25% cure. However in the CMRIT groups the cure rate was the greatest (39%) when HB22-7 was administered 24 hours after RIT, which compared favorably to the cure rates observed in the untreated (29%), RIT alone (13%), 24 hours prior (10%) and simultaneous (25%) treatment groups. When examining the degree of response (ranking cure better than CR, better than PR) in all treatment groups using the Kruskal Walis test, the differences were statistically significant (p=0.01). Individual comparisons against untreated controls were all statistically significant (p<0.05), with the exception of RIT alone (p=0.06) and HB22-7 given 24 hours prior to RIT (p=0.16). While comparison of only active treatment groups (RIT alone, CMRIT, and HB22-7) was not significantly different (p=0.18), the CMRIT groups treated with HB22-7 simultaneously and after 24 hours had the best observed pattern of response. Interestingly the group treated with HB22-7 alone had the highest cure rate (47%) which was a significant improvement when compared to the untreated controls (p<0.05).

Figure 6:
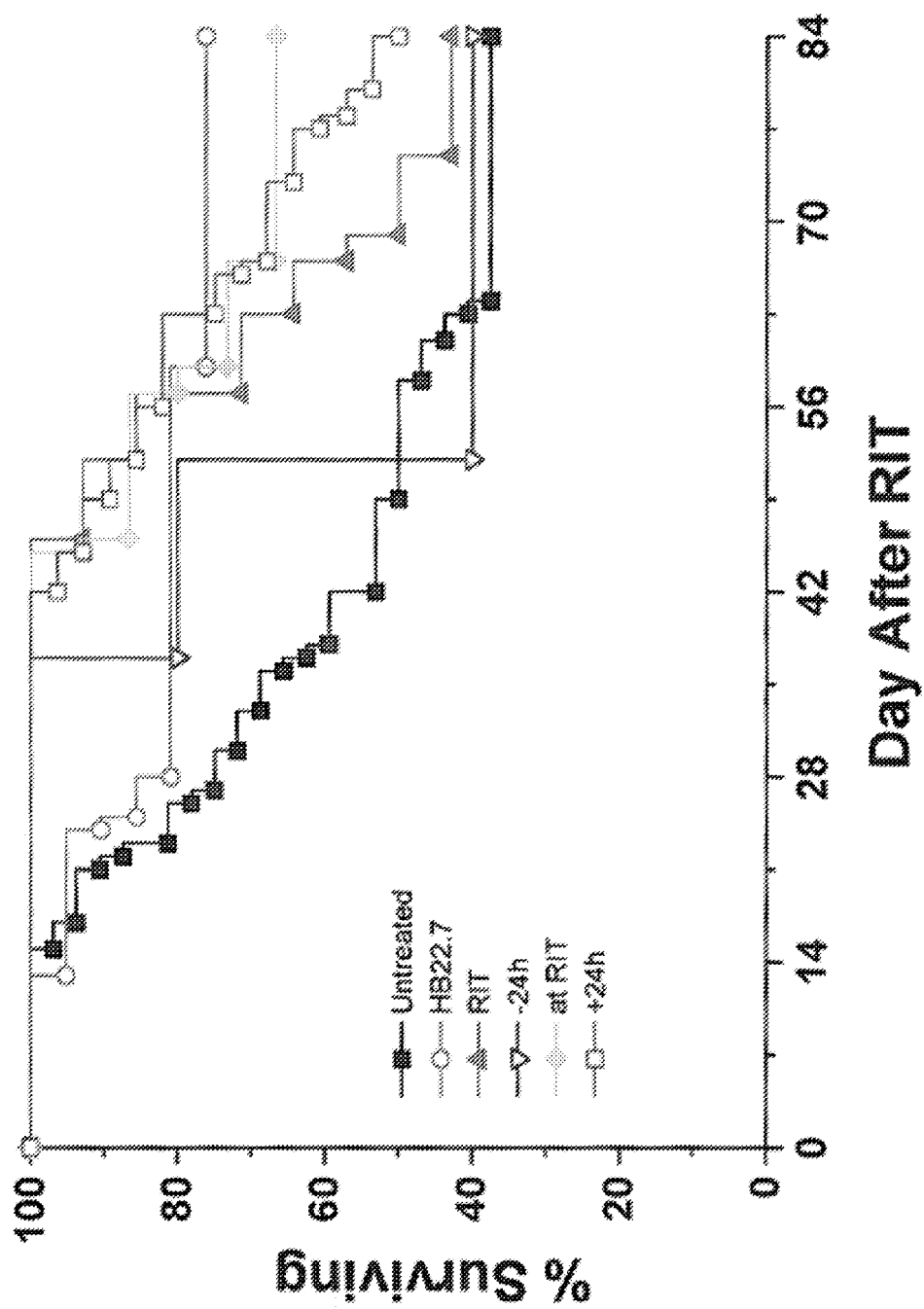
FIG. 6, Overall survival was assessed for Raji xenografted mice that were treated as described in FIG. 2. Mice were euthanized when the rumor burden exceeded 2000 mg or at the end of the 84 day trial. The data represents results of all independent trials.

Tumor volume regression and cure rates translated into a similar pattern of survival. At the end of the 84 day study period 38 and 42% of the untreated and RIT alone groups were alive respectively, (FIG. 6). In the CMRIT treatment groups, survival increased to 67 and 50% when HB22-7 was administered simultaneously and 24 hours after RIT, respectively. Analysis of survival using Kruskal Walis was significant (p<0.05) for comparison of all groups. Similar to the response rate analysis, comparison of survival in the RIT groups only did not reveal significant differences (p=0.41), however the best survival in these groups was consistently observed when HB22-7 was administered either simultaneous or 24 hours after RIT.

The best overall survival, 76%, was observed in the group treated with HB22-7 alone, a significant difference when compared to untreated control (p=0.02).

Toxicity

Figure 7:
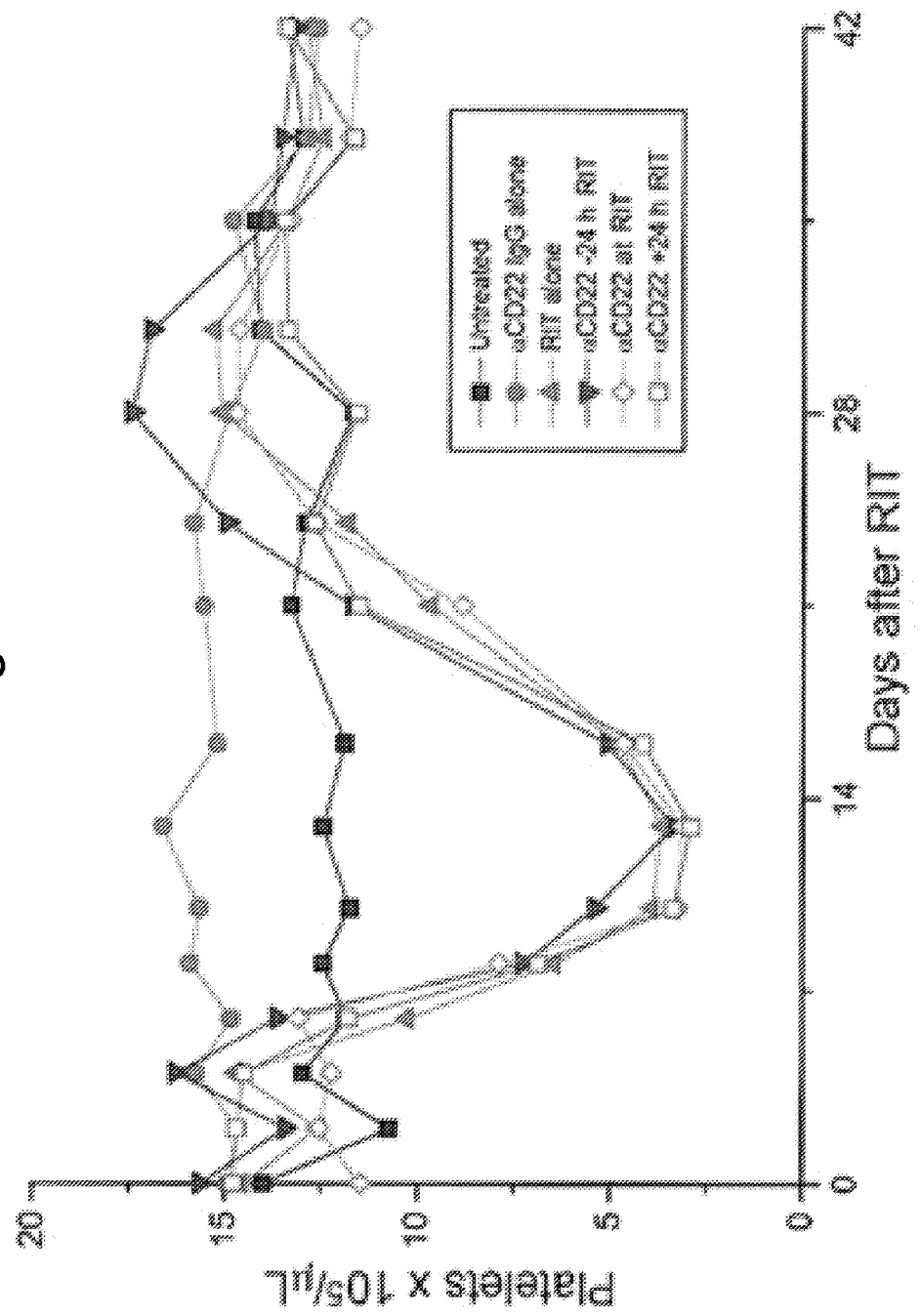
FIG. 7. Hematologic toxicity was assessed by measuring white blood cell (WBC), red blood cell (RBC) and platelet counts twice weekly in the Raji-xenografted mice that were treated as described in FIG. 2. When compared to RIT alone there was no difference in hematologic toxicity in the CMRIT groups. In addition, there was no hematologic toxicity observed in the mice treated with HB22-7 alone.
Figure 8:
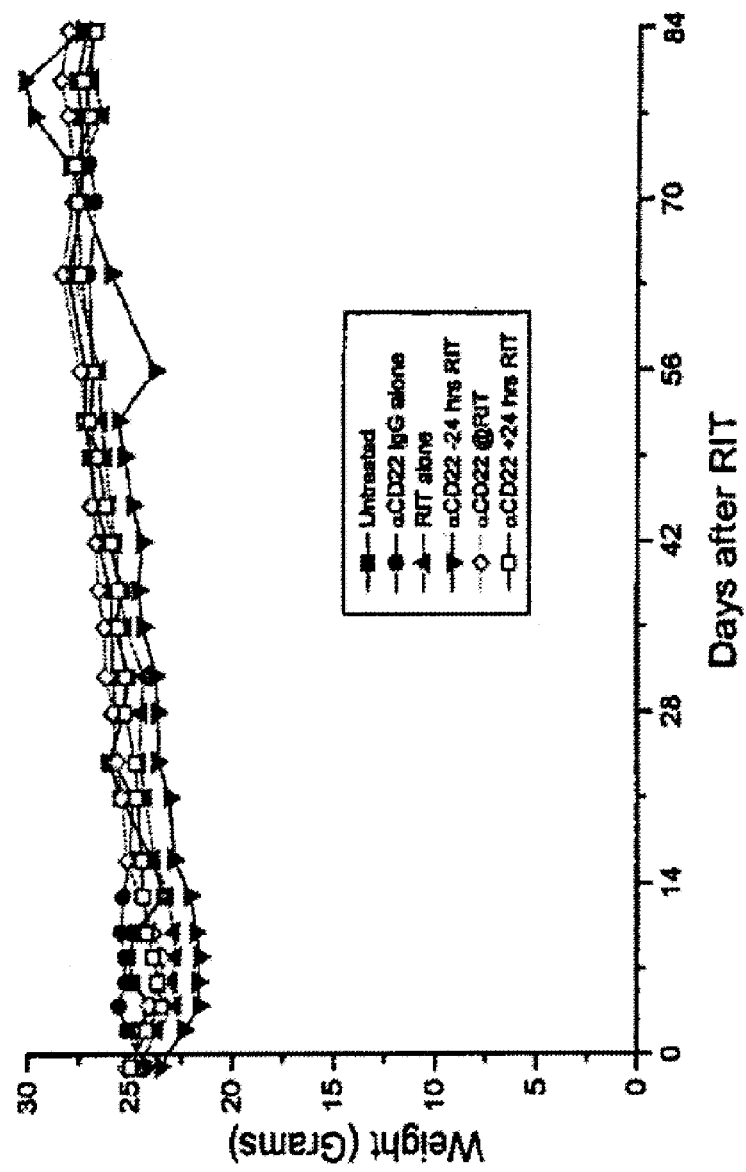
FIG. 8. Non-hematologic toxicity was assessed by measuring body weights twice weekly in Raji xenografted mice that were treated as described in FIG. 2. There were no significant differences in body weights in any of the treatment groups in all live xenograft trials.
Figure 15:
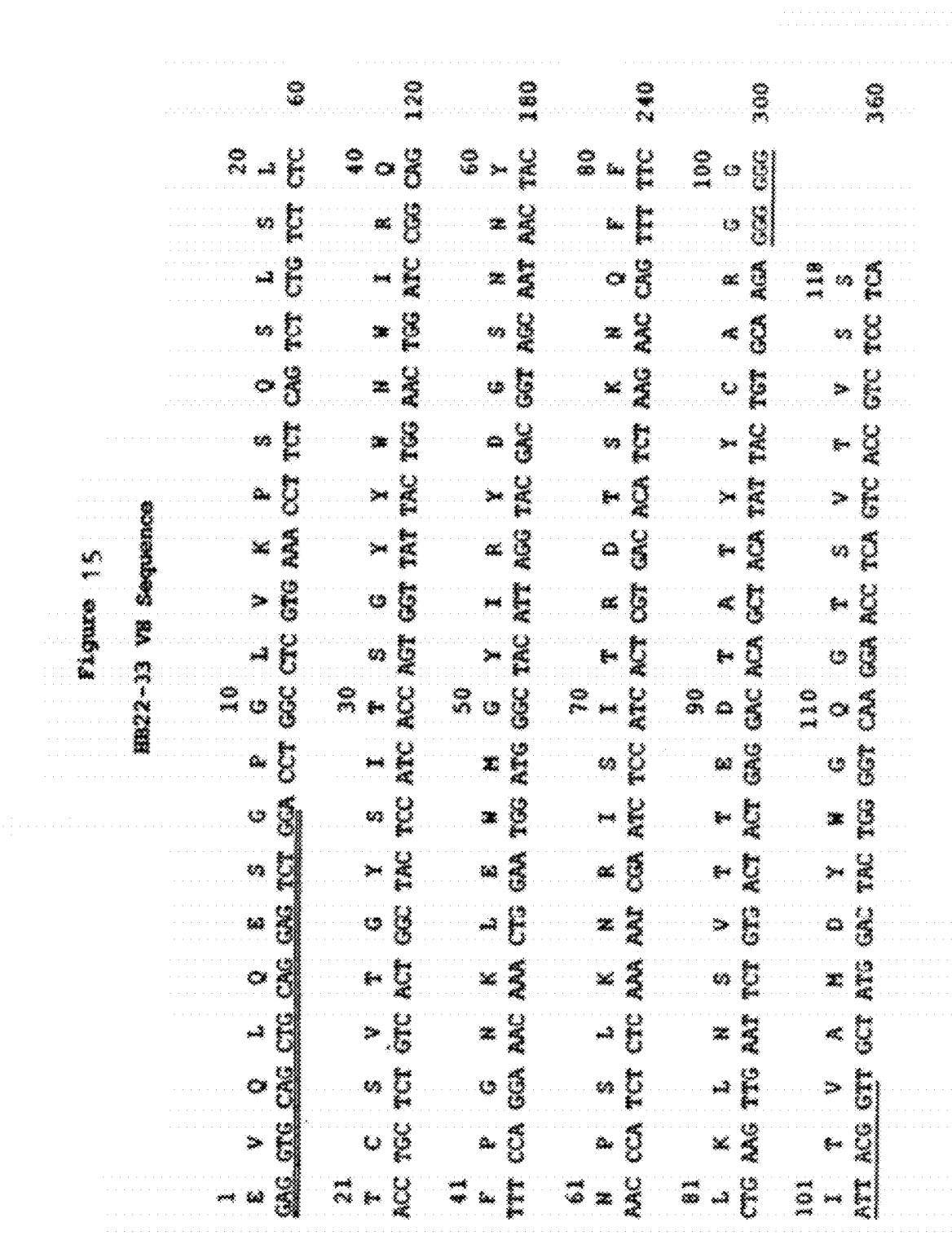
Figure 23:
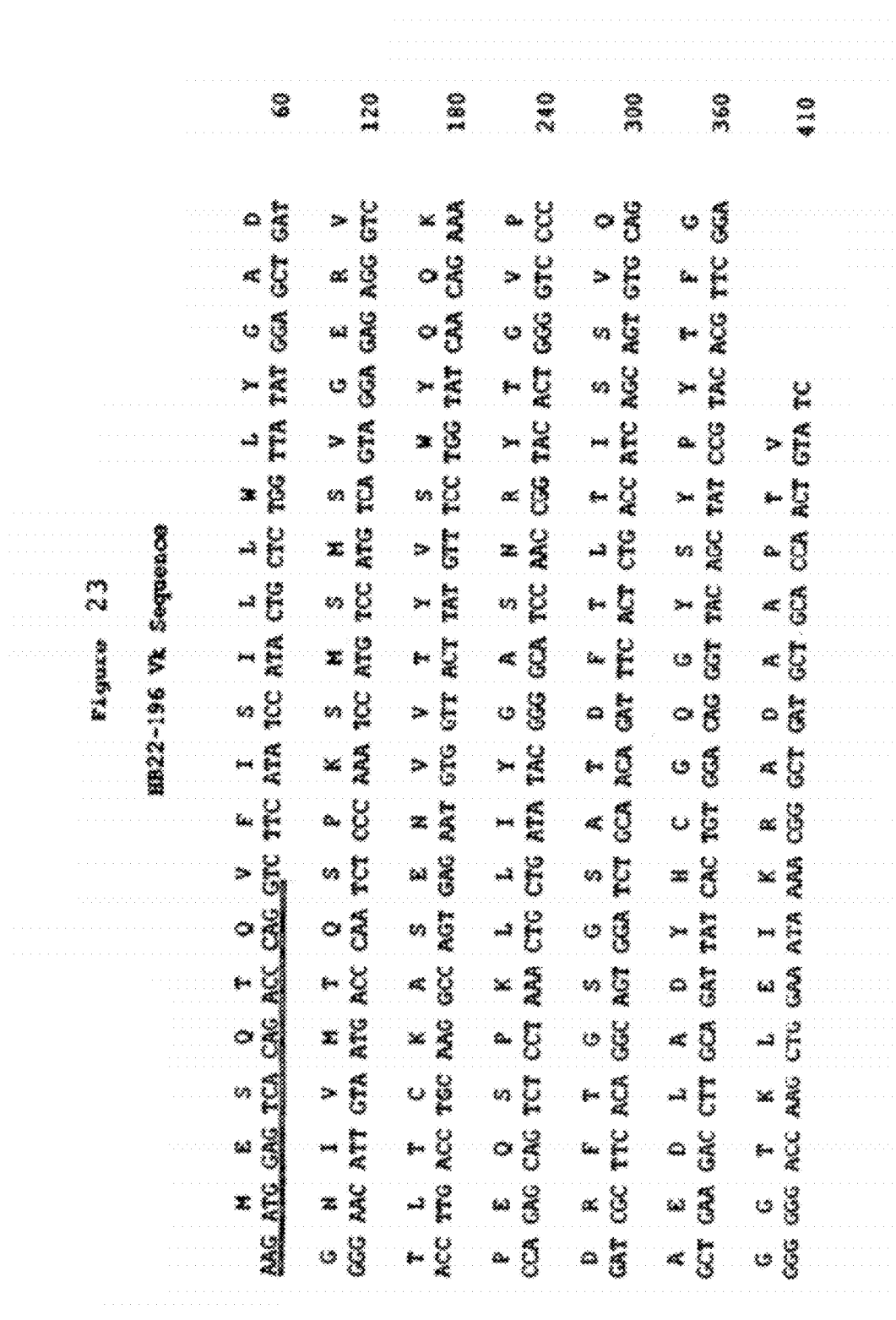

Hematologic and non-hematologic toxicities were assessed by blood counts and mouse weights, respectively (FIG. 7)). WBC and platelet nadirs in the RIT treatment groups were at 14-20, and 10-14 days respectively. WBC and platelet recovery was approximately 28 and 21 days after treatment, respectively. The WBC and platelet nadirs were consistent with observations in previous studies that utilized 150 μCi of $^{90}$Y-2IT-BAD-Lym-1. The hematologic toxicity of RIT was not altered by co-administration of HB22-7. No hematologic toxicity was detected in mice treated with HB22-7 alone. Analysis of mononuclear cell counts in all treatment groups revealed that HB22-7 had no effect on RIT-mediated mononuclear cell nadirs (data not shown). Non-hematologic toxicity as assessed by changes in mouse weight, and was found to be equivalent in all treatment groups (FIG. 8). There were no deaths due to toxicity in any treatment groups.

$^{90}$Y-DOTA-peptide-Lym-1 Pharmacokinetics

Blood and whole body clearances of $^{90}$Y-DOTA-peptide-Lym-1 in Raji-tumored mice with or without HB22-7 were similar (FIG. 9). The blood biological $T_{1/2}\alpha$ was 1.4 hours for RIT alone, and 2.2, 2.4, and 2.0 hours for the 24 hour prior, simultaneous and 24 hour after groups respectively. The blood biological $T_{1/2}\beta$. was 127 hours for the RIT alone group and 133, 87, and 103 hours for the 24 hours prior, simultaneous and 24 hours after groups respectively. The whole body $T_{1/2}$ was 246 hours for RIT alone and 207, 207, and 1.96 hours for the 24 hours prior, simultaneous and 24 hours after groups respectively. The addition of HB22-7 to RIT did not change the pharmacokinetics of $^{90}$Y-DOTA-peptide-Lym-1.

Discussion

Raji xenograft studies were designed to determine if the anti-CD22 mAb (HB22-7) would generate additive or synergistic effects when combined with RIT to enhance apoptosis and/or DNA damage induced by low dose-rate radiation. The Raji xenograft nude mouse model has proven useful when used to assess toxicity and efficacy of RIT using $^{90}$Y-2IT-BAD-Lym-1 RIT alone (O'Donnell et al., *Cancer Biotherapy and Radiopharmaceuticals* 13:351-361 (1998)). Responses in this pre-clinical model translated into significant efficacy in human clinical trials (O'Donnell et al., *Anticancer Res.* 20:3647-55 (2000): O'Donnell et al., *J. Nucl. Med.* 40:216 (1999) (Abstract)).

In the studies described in this Example, the addition of the anti-CD22 mAb HB22-7 to $^{90}$Y-DOTA-peptide-Lym-1 (125 μCi) enhanced the efficacy of RIT without any change in toxicity. Previous Raji xenograft studies with 150 and 200 μCi of $^{90}$Y-2IT-BAD-Lym-1 generated response and cure rates that were comparable to those observed, in the present study (O'Donnel et al., (1998), supra). The 125 μCi dose of $^{90}$Y-DOTA-peptide-Lym-1 was chosen based on these previous studies with the 21T-BAD linker. While the previous studies with 21T-BAD demonstrated greatest efficacy with the 200 μCi dose, the choice of 125 μCi was based on the hypothesis that HB22-7 would be synergistic or additive with RIT and the lower dose would allow for better assessment of these effects. The studies of this Example utilized a novel linker (DOTA-peptide) that has not been previously examined in lymphoma xenograft models. The DOTA-peptide linker was designed for enhanced hepatic degradation of unbound radiopharmaceutical thereby leading to a more favorable biodistribution. While tumor-specific uptake was not assessed in detail in this study, the toxicity profile observed with 125 μCi of $^{90}$Y-DOTA-peptide-Lym-1 alone was acceptable with no treatment-related mortality and predictable leukocyte and platelet nadirs.

HB22-7 was chosen based on in vitro studies demonstrating pro-apoptotic and signaling effects (Tuscano et al., *Blood* 94:1382-1392 (1999)), The treatment dose of HB22-7 utilized was empiric, however, it was based on the amount that was shown to be effective at inducing apoptosis in vitro and extrapolating this to the mouse model. In addition, when formulating the dose of HB22-7 consideration was given to the equivalent (when adjusted for body surface area differences in humans versus mice) dose of Rituximab® used in human clinical trials. The approximation to the Rituximab® dose was utilized based on the fact that this is the only naked mAb available that has demonstrated efficacy for the treatment of lymphoma, granted, the optimal dose of Rituximab® is currently undefined.

The study was designed to assess the efficacy of HB22-7 alone, the combination of RIT and HB22-7 as well, as the effect of three different sequence combinations. The tumor volume reduction observed with $^{90}$Y-DOTA-peptide-Lym-1 alone was consistent with previous studies with $^{90}$Y-2IT-BAD-Lym-1 in terms of timing, magnitude, and duration of response (O'Donnel et al., 1998, supra): RIT alone resulted in approximately 50% reduction in tumor volume 14 days after therapy. When assessing at the approximate point of maximal volume reduction (day 21-30) the addition of HB22-7 to RIT significantly enhanced the magnitude of response in a sequence specific manner. It appears that the addition of HB22-7 was most effective when administered simultaneously or 24 hours after RIT. The distinctive pattern of volume reduction was highly reproducible. Independent replicate trials demonstrated similar patterns and magnitude of tumor volume reduction. The improved reductions in tumor volume translated into superior response rates and survival. RIT alone generated 1.3% CR and 13% cures, the addition of HB22-7 increased the cure rate to 25% when administered simultaneously with RIT, and to 39% when HB22-7 was administered 24 hours after RIT.

This is the first time that a second monoclonal antibody has been combined with RIT, and demonstrates the potential of utilizing monoclonal antibodies or other agents with well defined physiologic properties that may augment efficacy without increasing toxicity.

Surprisingly the mice treated with HB22-7 alone had impressive tumor volume reduction and superior cure and survival rates when compared to all other treatment groups. Again, several independent trials generated highly consistent results with a delayed initial tumor volume stabilization, and then tumor volume reduction beginning approximately 14 days after treatment. This translated into the best cure and overall survival rates observed in any of the treatment groups.

In conclusion, the antibodies of the present invention, when administered alone, have been demonstrated to provide superior results in terms of tumor volume reduction, cure rate and overall survival when compared to other treatment regimens, including CMRIT, which is currently viewed as the most advanced therapeutic approach for the treatment of NHL.

Example 3

Sequence Analysis of Anti-CD22 Antibodies $V_H$ and Light Chain Gene Utilization Cytoplasmic RMA was extracted from 1-10×10$^5$ hybridoma cells using the RNeasy Mini Kit (Qiagen Chatsworth, Calif.). First strand cDNA was synthesized, from cytoplasmic RNA using oligo-dT primers (dT$_{18}$) and a Superscript Kit (Gibco BRL, Gaithersburg, Md.). One μl of cDNA solution was used as template for PCR amplification of $V_H$ genes. PCR reactions were carried out in a 100-μl volume of a reaction mixture composed of 10 mM Tris-HCl (ph 8.3), 50 mM KCl, 1.5 mM MgCl$_2$, 200 μM dNTP (Perkin Elmer, Foster City, Calif.), 50 pmol of each primer, and 5 U of Taq polymerase (ISC Bioexpress, Kaysville, Utah). Amplification was for 30 cycles (94° C. for 1 min, 58° for 1 min, 72° C. for 1 min; Thermocycler, Perkin Elmer). $V_H$ genes were amplified using a promiscuous sense 5' $V_H$ primer (Ms $V_H$E: 5' GGG AAT TCG AGG TGC AGC TGC AGG AGT CTG G 3'; SEQ ID NO: 2) as previously described (Kantor et al., J. Immunol. 158:1175-86 (1996)), and antisense primers complementary to the Cμ coding region (primer Cμ-in: 5' GAG GGG GAC ATT TGG GAA GGA CTG 3'; SEQ ID NO: 3) or the Cγ region (Primer C γ1: 5' GAG TTC CAG GTC ACT GTC ACT GGC 3'; SEQ ID NO: 4).

Light chain cDNA was amplified using a sense $V_κ$ primer [5' ATG GGC (AT)TC AAG ATG GAG TCA CA(GT) (AT) (CT)(CT) C(AT)G G 3'; SEQ ID NO; 5] and a Cλ antisense primer (5' ACT GGA TGG TGG GAA GAT G 3': SEQ ID NO: 6).

HB22-33 light chain sequences were amplified using a different sense $V_κ$ primer (5' ATG AAG TTG CCT GTT AGG CTG TTG GTG CTG 3': SEQ ID NO: 7).

Amplified PCR products were purified from agarose gels using the QIAquick gel purification kit (Qiagen) and were sequenced directly in both directions using an ABI 377 PRISM DNA sequencer after amplification using the Perkin Elmer Dye Terminator Sequencing system with AmpliTaq DNA polymerase and the same primers for initial PCR amplification. All $V_H$ and light chain regions were sequenced completely on both the sense and anti-sense DNA strands.

The alignment of the $V_H$ and $V_κ$ amino acid sequences for anti-CD22 monoclonal antibodies HB22-5, HB22-7, HB22-13, HB22-23, HB22-33, and HB22-196 are shown In FIGS. 10 and 17, respectively. FIGS. 11-16 show the nucleotide and amino acid sequences for heavy chain $V_H$-D-$J_H$ junctions of anti-CD22 Abs from hybridomas HB22-5 (SEQ ID NOS: 8 and 9), HB22-7 (SEQ ID NOS: 10 and 11); HB-22-13 (SEQ ID NOS: 12 and 13); HB-22-23 (SEQ ID NOS: 14 and 15); HB-22-33 (SEQ ID NOS: 16 and 17); and HB-22-196 (SEQ ID NOS: 18 and 19). FIGS. 18-23 show the nucleotide and deduced amino acid sequences for kappa light chain V-J-constant region junctions of anti-CD22 Abs from hybridomas HB22-5 (SEQ ID NOS: 20 and 21); HB22-7 (SEQ ID NOS: 22 and 23); HB22-13 (SEQ ID NOS: 24 and 25) HB22-23 (SEQ ID NOS; 26 and 27); HB22-33 (SEQ ID NOS: 28 and 29); and HB22-196 (SEQ ID NOS: 30 and 31).

---

What is claimed is:

1. A method of treating a human diagnosed with an autoimmune disease or autoimmune disorder, comprising administering to said human an effective amount of a humanized monoclonal blocking antibody that specifically binds to human CD22 comprising a heavy chain variable domain comprising variable heavy (VH) complementarity determining regions (CDRs) and a light chain variable domain comprising variable light (VL) CDRs, wherein said blocking antibody specifically binds to an epitope associated with the first two Ig-like domains of native human CD22, wherein said blocking antibody comprises:

a VH CDR1 having the amino acid sequence GYYMH (SEQ ID NO:33); a VH CDR2 having the amino acid sequence AVNPNTAGLTYNQRFKD (SEQ ID NO:39); a VH CDR3 having the amino acid sequence VDYDDYGYWFFDV (SEQ ID NO: 45); a VL CDR1 having the amino acid sequence KASENVVTYVS (SEQ ID NO:55): a VL CDR2 having the amino acid sequence GASNRYT (SEQ ID NO:61); and a VL CDR3 having the amino acid sequence GQGYSYPYT (SEQ ID NO:67), and wherein said method reduces the number of B cells or B cell subsets in the human.

2. The method of claim 1, wherein said treatment is unaccompanied by any other treatment for the autoimmune disease.

3. The method of claim 1, wherein said humanized monoclonal blocking antibody is a fragment of a complete antibody.

4. The method of claim 1, wherein said humanized monoclonal blocking antibody is a bispecific antibody.

5. The method of claim 1, wherein said humanized monoclonal blocking antibody is administered intravenously.

6. The method of claim 1, wherein said method reduces the number of B cells or B cell subsets in the human by at least 25%, 35%, 50%, or 70%.

7. The method of claim 1, wherein the humanized monoclonal blocking antibody blocks CD22 binding to its ligand by at least about 70%.

8. The method of claim 1, wherein the humanized monoclonal blocking antibody blocks CD22 binding to its ligand by at least about 80%.

9. The method of claim 1, wherein the autoimmune disease is rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis, Wegener's granulomatosis, microscopic polyangiitis, urveitis, Sjogren's syndrome, Crohn's disease, Reiter's syndrome, ankylosing spondylitis, Lyme arthritis, Guillain-Barre syndrome, Hashimoto's thyroiditis, cardiomyopathy, sclerosis, atopic dermatitis, thrombocytopenic purpura, agranulocytosis, autoimmune hemolytic anemias, immune reactions against foreign antigens, myasthenia gravis, Type I diabetes, Graves' disease, or allergic responses.

10. The method of claim 1, wherein the humanized monoclonal blocking antibody is an IgG1 or IgG4 antibody.

11. A method of reducing the number of B cells or B cell subsets in a human diagnosed with an autoimmune disease or autoimmune disorder, comprising administering to said human an effective amount of a humanized monoclonal blocking antibody that specifically binds to human CD22, said blocking antibody comprising a heavy chain variable domain comprising VH CDRs and a light chain variable domain comprising VL CDRs, wherein said blocking antibody specifically binds to an epitope associated with the first two Ig-like domains of native human CD22, wherein said blocking antibody comprises:

a VH CDR1 having the amino acid sequence GYYMH (SEQ ID NO:33); a VH CDR2 having the amino acid sequence AVNPNTAGLTYNQRFKD (SEQ ID NO:39); a VI CDR3 having the amino acid sequence VDYDDYGYWFFDV (SEQ ID NO:45); a VL CDR1 having the amino acid sequence KASENVVTYVS (SEQ ID NO:55); a VL CDR2 having the amino acid sequence GASNRYT (SEQ ID NO:61); and a VL CDR3 having the amino acid sequence GQGYSYPYT (SEQ ID NO:67), and wherein said method reduces the number of B cells or B cell subsets in the human.

12. The method of claim 11, wherein said method reduces the number of B cells or B cell subsets in the human by at least 25%, 35%, 50%, or 70%.

13. The method of claim 11, wherein the humanized monoclonal blocking antibody is an IgG1 or IgG4 antibody.

14. The method of claim 11, wherein said humanized monoclonal blocking antibody is a fragment of a complete antibody.

15. The method of claim 11, wherein said humanized monoclonal blocking antibody is a bispecific antibody.

16. The method of claim 11, wherein said humanized monoclonal blocking antibody is administered intravenously.

17. The method of claim 11, wherein the humanized monoclonal blocking antibody blocks CD22 binding to its ligand by at least about 70%.

18. The method of claim 11, wherein the humanized monoclonal blocking antibody blocks CD22 binding to its ligand by at least about 80%.

19. The method of claim 11, wherein the autoimmune disease is rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis, Wegener's granulomatosis, microscopic polyangiitis, urveitis, Sjogren's syndrome, Crohn's disease, Reiter's syndrome, ankylosing spondylitis, Lyme arthritis, Guillain-Barre syndrome, Hashimoto's thyroiditis, cardiomyopathy, sclerosis, atopic dermatitis, thrombocytopenic purpura, agranulocytosis, autoimmune hemolytic anemias, immune reactions against foreign antigens, myasthenia gravis, Type I diabetes, Graves' disease, or allergic responses.

\* \* \* \* \*

SEQUENCE LISTING

```
<160> NUMBER OF SEQ ID NOS: 67

<210> SEQ ID NO 1
<211> LENGTH: 847
<212> TYPE: PRT
<213> ORGANISM: homo sapiens

<400> SEQUENCE: 1

Met His Leu Leu Gly Pro Trp Leu Leu Leu Val Leu Glu Tyr Leu
 1               5                  10                  15

Ala Phe Ser Asp Ser Ser Lys Trp Val Phe Glu His Pro Glu Thr Leu
                20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                    85                  90                  95

Asp Lys Asn Lys Asn Cys Thr Leu Ser Ile His Pro Val His Leu Asn
                100                 105                 110

Asp Ser Gly Gln Leu Gly Leu Arg Met Glu Ser Lys Thr Glu Lys Trp
            115                 120                 125

Met Glu Arg Ile His Leu Asn Val Ser Glu Arg Pro Phe Pro Pro His
        130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                    165                 170                 175

Leu Leu Glu Gly Val Pro Met Arg Gln Ala Ala Val Thr Ser Thr Ser
                180                 185                 190

Leu Thr Ile Lys Ser Val Phe Thr Arg Ser Glu Leu Lys Phe Ser Pro
```

-continued

```
            195                 200                 205
Gln Trp Ser His His Gly Lys Ile Val Thr Cys Gln Leu Gln Asp Ala
210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                    245                 250                 255

Glu Gly Asp Ser Val Thr Met Thr Cys Glu Val Ser Ser Asn Pro
                260                 265                 270

Glu Tyr Thr Thr Val Ser Trp Leu Lys Asp Gly Thr Ser Leu Lys Lys
                275                 280                 285

Gln Asn Thr Phe Thr Leu Asn Leu Arg Glu Val Thr Lys Asp Gln Ser
290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
                340                 345                 350

Cys Met Ser Leu Ala Asn Pro Leu Pro Thr Asn Tyr Thr Trp Tyr His
                355                 360                 365

Asn Gly Lys Glu Met Gln Gly Arg Thr Glu Glu Lys Val His Ile Pro
370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
                420                 425                 430

Arg Glu Gly Asp Thr Val Thr Leu Ser Cys Asn Tyr Asn Ser Ser Asn
                435                 440                 445

Pro Ser Val Thr Arg Tyr Glu Trp Lys Pro His Gly Ala Trp Glu Glu
450                 455                 460

Pro Ser Leu Gly Val Leu Lys Ile Gln Asn Val Gly Trp Asp Asn Thr
465                 470                 475                 480

Thr Ile Ala Cys Ala Arg Cys Asn Ser Trp Cys Ser Trp Ala Ser Pro
                485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
                515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
                595                 600                 605

Gly Lys Ser Ala Thr Leu Thr Cys Glu Ser Asp Ala Asn Pro Pro Val
610                 615                 620
```

| | | | | | | | | | | | | | | |
|---|---|---|---|---|---|---|---|---|---|---|---|---|---|---|
| Ser<br>625 | His | Tyr | Thr | Trp<br>630 | Phe | Asp | Trp | Asn | Asn<br>635 | Gln | Ser | Leu | Pro | His<br>640 | His |

Ser Gln Lys Leu Arg Leu Glu Pro Val Lys Val Gln His Ser Gly Ala
            645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
            675                 680                 685

Ala Val Gly Leu Gly Ser Cys Leu Ala Ile Leu Ile Leu Ala Ile Cys
690                     695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
770                 775                 780

Arg Pro Pro Arg Thr Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
            835                 840                 845

<210> SEQ ID NO 2
<211> LENGTH: 31
<212> TYPE: DNA
<213> ORGANISM: homo sapiens

<400> SEQUENCE: 2
gggaattcga ggtgcagctg caggagtctg g                              31

<210> SEQ ID NO 3
<211> LENGTH: 24
<212> TYPE: DNA
<213> ORGANISM: homo sapiens

<400> SEQUENCE: 3 gaggggaca tttgggaagg actg                                       24

<210> SEQ ID NO 4
<211> LENGTH: 24
<212> TYPE: DNA
<213> ORGANISM: homo sapiens

<400> SEQUENCE: 4
gagttccagg tcactgtcac tggc                                      24

<210> SEQ ID NO 5
<211> LENGTH: 31
<212> TYPE: DNA
<213> ORGANISM: homo sapiens

<400> SEQUENCE: 5

```
atgggcwtca agatggagtc acakwyycwg g                                   31
```

<210> SEQ ID NO 6
<211> LENGTH: 19
<212> TYPE: DNA
<213> ORGANISM: homo sapiens

<400> SEQUENCE: 6

```
actggatggt gggaagatg                                                 19
```

<210> SEQ ID NO 7
<211> LENGTH: 30
<212> TYPE: DNA
<213> ORGANISM: homo sapiens

<400> SEQUENCE: 7

```
atgaagttgc ctgttaggct gttggtgctg                                     30
```

<210> SEQ ID NO 8
<211> LENGTH: 357
<212> TYPE: DNA
<213> ORGANISM: homo sapiens

<400> SEQUENCE: 8

```
gaggtgcagc tgcaggagtc tggacctgag ctggtgaagc ctggagcttc aatgaagata    60
tcctgcaagg cttctggtta ctcattcact gactacacca tgaactgggt gaagcagagc   120
catggaaaga accttgagtg gattggactt cttcatcctt caatggtgg tactagctac    180
aaccagaagt tcaagggcaa ggccacatta tctgtagaca agtcatccag cacagccttc   240
atggagctcc tcagtctgac atctgaggac tctgcagtct atttctgtgc aagagggaca   300
ggtcggaact atgctatgga ctactgggt caaggaacct cagtcaccgt ctcctca      357
```

<210> SEQ ID NO 9
<211> LENGTH: 119
<212> TYPE: PRT
<213> ORGANISM: homo sapiens

<400> SEQUENCE: 9

```
Glu Val Gln Leu Gln Glu Ser Gly Pro Glu Leu Val Lys Pro Gly Ala
 1               5                  10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Leu His Pro Phe Asn Gly Gly Thr Ser Tyr Asn Gln Lys Phe
    50                  55                  60

Lys Gly Lys Ala Thr Leu Ser Val Asp Lys Ser Ser Ser Thr Ala Phe
65                  70                  75                  80

Met Glu Leu Leu Ser Leu Thr Ser Glu Asp Ser Ala Val Tyr Phe Cys
                85                  90                  95

Ala Arg Gly Thr Gly Arg Asn Tyr Ala Met Asp Tyr Trp Gly Gln Gly
            100                 105                 110

Thr Ser Val Thr Val Ser Ser
        115
```

<210> SEQ ID NO 10
<211> LENGTH: 351
<212> TYPE: DNA
<213> ORGANISM: homo sapiens

<400> SEQUENCE: 10

```
gaggtgcagc tgcaggagtc tggacctggc ctggtggcgc cctcacagag cctgtccatc    60
acatgcaccg tctcagggtt ctcattaagc gactatggtg taaactgggt tcgccagatt   120
ccaggaaagg gtctggagtg gctgggaata atatggggtg atggaaggac agactataat   180
tcagctctca aatccagact gaacatcagc aaggacaact ccaagagcca agttttcttg   240
aaaatgaaca gtctgaaagc tgatgacaca gccaggtact actgtgccag agcccccggt   300
aatagggcta tggagtactg gggtcaagga acctcagtca ccgtctcctc a            351
```

<210> SEQ ID NO 11
<211> LENGTH: 117
<212> TYPE: PRT
<213> ORGANISM: homo sapiens

<400> SEQUENCE: 11

```
Glu Val Gln Leu Gln Glu Ser Gly Pro Gly Leu Val Ala Pro Ser Gln
  1               5                  10                  15

Ser Leu Ser Ile Thr Cys Thr Val Ser Gly Phe Ser Leu Ser Asp Tyr
             20                  25                  30

Gly Val Asn Trp Val Arg Gln Ile Pro Gly Lys Gly Leu Glu Trp Leu
         35                  40                  45

Gly Ile Ile Trp Gly Asp Gly Arg Thr Asp Tyr Asn Ser Ala Leu Lys
     50                  55                  60

Ser Arg Leu Asn Ile Ser Lys Asp Asn Ser Lys Ser Gln Val Phe Leu
 65                  70                  75                  80

Lys Met Asn Ser Leu Lys Ala Asp Asp Thr Ala Arg Tyr Tyr Cys Ala
                 85                  90                  95

Arg Ala Pro Gly Asn Arg Ala Met Glu Tyr Trp Gly Gln Gly Thr Ser
            100                 105                 110

Val Thr Val Ser Ser
        115
```

<210> SEQ ID NO 12
<211> LENGTH: 363
<212> TYPE: DNA
<213> ORGANISM: homo sapiens

<400> SEQUENCE: 12

```
gaggtgcagc tgcaggagtc tggaggaggc ttggtacagc ctgggggttc tctgagactc    60
tcctgtgcaa cttctgggtt caccttcatt gattactaca tgaactgggt ccgccagcct   120
ccaggaaagg cacttgagtg gttgggtttt attaaaaaca aatttaatgg ttacacaaca   180
gaatacaata tctctgtgaa gggtcggttc accatctcca gagataattc ccaaagcatc   240
ctctatcttc aaatgaacac cctgagagct gaggacagtg ccacttatta ctgtgcaaga   300
gggctgggac gtagctatgc tatggactac tggggtcaag gaacctcagt caccgtctcc   360
tca                                                                 363
```

<210> SEQ ID NO 13
<211> LENGTH: 121
<212> TYPE: PRT
<213> ORGANISM: homo sapiens

<400> SEQUENCE: 13

```
Glu Val Gln Leu Gln Glu Ser Gly Gly Gly Leu Val Gln Pro Gly Gly
  1               5                  10                  15

Ser Leu Arg Leu Ser Cys Ala Thr Ser Gly Phe Thr Phe Ile Asp Tyr
```

```
                 20                  25                  30
Tyr Met Asn Trp Val Arg Gln Pro Pro Gly Lys Ala Leu Glu Trp Leu
            35                  40                  45

Gly Phe Ile Lys Asn Lys Phe Asn Gly Tyr Thr Thr Glu Tyr Asn Thr
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Gly Leu Gly Arg Ser Tyr Ala Met Asp Tyr Trp Gly
            100                 105                 110

Gln Gly Thr Ser Val Thr Val Ser Ser
            115                 120

<210> SEQ ID NO 14
<211> LENGTH: 357
<212> TYPE: DNA
<213> ORGANISM: homo sapiens

<400> SEQUENCE: 14
gaggtgcagc tgcaggagtc tggaggaggg cttggtgcaa cctggagatc catgaaactc      60
tcctgtgttg cctctggatt cactttcagt tactactgga tgaactgggt ccgccagtct     120
ccagagaagg ggcttgagtg gattgctgaa attagattga atctaataa ttatgcaaca      180 cattatgcgg agtctgtgaa agggaggttc accatctcaa gagatgattc caaaagtagt     240
gtctacctgc aaatgaacaa cttaagagct gaagacactg gcatttatta ctgtaccagg     300
tatgatggtt cctcccggga ctactggggc caaggcacca ctctcacagt ctcctca       357

<210> SEQ ID NO 15
<211> LENGTH: 119
<212> TYPE: PRT
<213> ORGANISM: homo sapiens

<400> SEQUENCE: 15

Glu Val Gln Leu Gln Glu Ser Gly Gly Gly Leu Gly Ala Thr Trp Arg
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Ile
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Tyr Asp Gly Ser Ser Arg Asp Tyr Trp Gly Gln Gly
            100                 105                 110

Thr Thr Leu Thr Val Ser Ser
        115

<210> SEQ ID NO 16
<211> LENGTH: 360
<212> TYPE: DNA
<213> ORGANISM: homo sapiens

<400> SEQUENCE: 16
```

```
gaggtgcagc tgcaggagtc tggacctggc ctcgtgaaac cttctcagtc tctgtctctc        60
acctgctctg tcactggcta ctccatcacc agtggttatt actggaactg gatccggcag       120
tttccaggaa acaaactgga atggatgggc tacattaggt acgacggtag caataactac       180
aacccatctc tcaaaaatcg aatctccatc actcgtgaca catctaagaa ccagttttc        240 aagttgctga agttgaattc tgtgactact gaggacacag ctacatatta ctgtgcaaga       300
ggggggatta cggttgctat ggactactgg ggtcaaggaa cctcagtcac cgtctcctca       360
```

<210> SEQ ID NO 17
<211> LENGTH: 118
<212> TYPE: PRT
<213> ORGANISM: homo sapiens

<400> SEQUENCE: 17

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Gly Ile Thr Val Ala Met Asp Tyr Trp Gly Gln Gly Thr
            100                 105                 110

Ser Val Thr Val Ser Ser
        115

<210> SEQ ID NO 18
<211> LENGTH: 366
<212> TYPE: DNA
<213> ORGANISM: homo sapiens

<400> SEQUENCE: 18

```
gaggtgcagc tgcaggagtc tggacctgac ctggtgaagc ctggggcttc agtgaagata        60
tcctgtaagg cttctggtta ctcattcatt ggctattaca tgcactggct gaagcagagc       120
catggaaaga gccttgagtg gattggagct gttaatccta acactgctgg tcttacctac       180
aaccagaggt tcaaggacaa ggccatatta actgtagaca agtcatccaa cacagcctat       240
atggagctcc gcagcctgac atctgaggac tctgcggtct attactgttc aagagtggac       300
tatgatgact acgggtactg gttcttcgat gtctggggcg cagggaccac ggtcaccgtc       360
tcctca                                                                  366
```

<210> SEQ ID NO 19
<211> LENGTH: 122
<212> TYPE: PRT
<213> ORGANISM: homo sapiens

<400> SEQUENCE: 19

Glu Val Gln Leu Gln Glu Ser Gly Pro Asp Leu Val Lys Pro Gly Ala
1               5                   10                  15

Ser Val Lys Ile Ser Cys Lys Ala Ser Gly Tyr Ser Phe Ile Gly Tyr
            20                  25                  30

```
Tyr Met His Trp Leu Lys Gln Ser His Gly Lys Ser Leu Glu Trp Ile
     35                  40                  45

Gly Ala Val Asn Pro Asn Thr Ala Gly Leu Thr Tyr Asn Gln Arg Phe
 50                  55                  60

Lys Asp Lys Ala Ile Leu Thr Val Asp Lys Ser Ser Asn Thr Ala Tyr
 65                  70                  75                  80

Met Glu Leu Arg Ser Leu Thr Ser Glu Asp Ser Ala Val Tyr Tyr Cys
                 85                  90                  95

Ser Arg Val Asp Tyr Asp Asp Tyr Gly Tyr Trp Phe Phe Asp Val Trp
             100                 105                 110

Gly Ala Gly Thr Thr Val Thr Val Ser Ser
             115                 120
```

<210> SEQ ID NO 20
<211> LENGTH: 410
<212> TYPE: DNA
<213> ORGANISM: homo sapiens

<400> SEQUENCE: 20

```
aagatggagt cacagaccca ggtcttcgta tttctactgc tctgtgtgtc tggtgctcat    60
gggagtattg tgatgaccca gactcccaaa ttcctgcttg tatcaacagg agacagggtt   120
accattacct gcaaggccag tcagactgtg actaatgatt tagcttggta ccaacagaag   180
ccagggcagt ctcctaaact gctgatatac tatgcatcca atcgctacac tggagtccct   240
gatcgcttca ctggcagtgg atatgggacg gacttcactt tcaccatcaa cactgtgcag   300
gctgaagacc tggcagtttta tttctgtcag caggattata gctctcctct cacgttcggt   360
gctgggacca agctggaact gaaacgggct gatgctgcac caactgtatc                410
```

<210> SEQ ID NO 21
<211> LENGTH: 135
<212> TYPE: PRT
<213> ORGANISM: homo sapiens

<400> SEQUENCE: 21

```
Met Glu Ser Gln Thr Gln Val Phe Val Phe Leu Leu Leu Cys Val Ser
 1               5                  10                  15

Gly Ala His Gly Ser Ile Val Met Thr Gln Thr Pro Lys Phe Leu Leu
                 20                  25                  30

Val Ser Thr Gly Asp Arg Val Thr Ile Thr Cys Lys Ala Ser Gln Thr
             35                  40                  45

Val Thr Asn Asp Leu Ala Trp Tyr Gln Gln Lys Pro Gly Gln Ser Pro
 50                  55                  60

Lys Leu Leu Ile Tyr Tyr Ala Ser Asn Arg Tyr Thr Gly Val Pro Asp
 65                  70                  75                  80

Arg Phe Thr Gly Ser Gly Tyr Gly Thr Asp Phe Thr Phe Thr Ile Asn
                 85                  90                  95

Thr Val Gln Ala Glu Asp Leu Ala Val Tyr Phe Cys Gln Gln Asp Tyr
             100                 105                 110

Ser Ser Pro Leu Thr Phe Gly Ala Gly Thr Lys Leu Glu Leu Lys Arg
             115                 120                 125

Ala Asp Ala Ala Pro Thr Val
             130                 135
```

<210> SEQ ID NO 22
<211> LENGTH: 410
<212> TYPE: DNA
<213> ORGANISM: homo sapiens

<400> SEQUENCE: 22

```
aagatggagt cacagaccca ggtcttcgta tttctactgc tctgtgtgtc tggtgctcat    60
gggagtattg tgatgaccca gactcccaaa ttcctgcttg tatcagcagg agacaggatt   120
accttaacct gcaaggccag tcagagtgtg actaatgatg tagcttggta ccaacagaag   180
ccagggcagt ctcctaaact gctgatatac tatgcatcca atcgctacac tggagtccct   240
gatcgcttca ctggcagtgg atatgggacg gatttcactt tcaccatcag cactgtgcag   300
gctgaagacc tggcagttta tttctgtcag caggattata ggtctccgtg gacgttcggt   360
ggaggcacca agctggaaat caaacgggct gatgctgcac caactgtatc               410
```

<210> SEQ ID NO 23
<211> LENGTH: 135
<212> TYPE: PRT
<213> ORGANISM: homo sapiens

<400> SEQUENCE: 23

```
Met Glu Ser Gln Thr Gln Val Phe Val Phe Leu Leu Leu Cys Val Ser
  1               5                  10                  15
Gly Ala His Gly Ser Ile Val Met Thr Gln Thr Pro Lys Phe Leu Leu
             20                  25                  30
Val Ser Ala Gly Asp Arg Ile Thr Leu Thr Cys Lys Ala Ser Gln Ser
         35                  40                  45
Val Thr Asn Asp Val Ala Trp Tyr Gln Gln Lys Pro Gly Gln Ser Pro
     50                  55                  60
Lys Leu Leu Ile Tyr Tyr Ala Ser Asn Arg Tyr Thr Gly Val Pro Asp
 65                  70                  75                  80
Arg Phe Thr Gly Ser Gly Tyr Gly Thr Asp Phe Thr Phe Thr Ile Ser
                 85                  90                  95
Thr Val Gln Ala Glu Asp Leu Ala Val Tyr Phe Cys Gln Gln Asp Tyr
            100                 105                 110
Arg Ser Pro Trp Thr Phe Gly Gly Gly Thr Lys Leu Glu Ile Lys Arg
        115                 120                 125
Ala Asp Ala Ala Pro Thr Val
    130                 135
```

<210> SEQ ID NO 24
<211> LENGTH: 410
<212> TYPE: DNA
<213> ORGANISM: homo sapiens

<400> SEQUENCE: 24

```
aagatggagt cacagaccca ggtcttcgta tttctactgc tctgtgtgtc tggtgctcat    60
gggagtattg tgatgaccca gactcccaaa ttcctgcttg tatcagcagg agacagggtt   120
tccataacct gcaaggccag tcagagtgtg actaatgatg taacttggta ccaacagaag   180
ccagggcagt ctcctaaatt gctgatatac tttgcatcca atcgctacac tggagtccct   240
gatcgcttca ctggcagtgg atatgggacg gatttcactt tcaccatcag cactgtgcag   300
gctgaagacc tggcagttta tttctgtcag caggattata gctctccgct cacgttcggt   360
gctgggacca agctggagct gaaacgggct gatgctgcac caactgtatc               410
```

<210> SEQ ID NO 25
<211> LENGTH: 135
<212> TYPE: PRT
<213> ORGANISM: homo sapiens -continued

<400> SEQUENCE: 25

Met Glu Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Ser Ile Thr Cys Lys Ala Ser Gln Ser
        35                  40                  45

Val Thr Asn Asp Val Thr Trp Tyr Gln Gln Lys Pro Gly Gln Ser Pro
    50                  55                  60

Lys Leu Leu Ile Tyr Phe Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Leu Thr Phe Gly Ala Gly Thr Lys Leu Glu Leu Lys Arg
        115                 120                 125

Ala Asp Ala Ala Pro Thr Val
    130                 135

<210> SEQ ID NO 26
<211> LENGTH: 410
<212> TYPE: DNA
<213> ORGANISM: homo sapiens

<400> SEQUENCE: 26
aagatggagt cacagaccca ggtcttcgta tttctactgc tctgtgtgtc tggtgctcat    60
gggagtattg tgatgaccca gactcccaaa ttcctgcttg tatcagcagg agacagggtc   120
accataagct gcaaggccag tcagagtgtg agtaatgatg tagcttggta ccaacagaag   180
ccagggcagt ctcctaaact gctgatatac tatgcatcca agcgctatac tggagtccct   240
gatcgcctca ctggcagtgg atatgggacg gatttcactt tcaccatcag cactgtgcag   300
gctgaagacc tggcagttta tttctgtcag caggatcata gctatccgtg gacgttcggt   360
ggaggcacca agctggagat caaacgggct gatgctgcac caactgtatc                410

<210> SEQ ID NO 27
<211> LENGTH: 135
<212> TYPE: PRT
<213> ORGANISM: homo sapiens

<400> SEQUENCE: 27

Met Glu Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Ser Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Lys Arg Tyr Thr Gly Val Pro Asp
65                  70                  75                  80

Arg Leu Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp His
            100                 105                 110

```
Ser Tyr Pro Trp Thr Phe Gly Gly Gly Thr Lys Leu Glu Ile Lys Arg
        115                 120                 125

Ala Asp Ala Ala Pro Thr Val
        130                 135

<210> SEQ ID NO 28
<211> LENGTH: 419
<212> TYPE: DNA
<213> ORGANISM: homo sapiens

<400> SEQUENCE: 28
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgatttttct     240 ggggtcccag ataggttcag tggcagtgga tcaggacag atttcacact caagatcagc      300
agagtggagg ctgaggatct gggagtttat ttctgctctc aaagtacaca tgttccgtac     360
acgttcggag gggggaccaa gctggaaata aaacgggctg atgctgcacc aactgtatc      419

<210> SEQ ID NO 29
<211> LENGTH: 139
<212> TYPE: PRT
<213> ORGANISM: homo sapiens

<400> SEQUENCE: 29

Met Lys Leu Pro Val Arg Leu Leu Val Leu Met Phe Trp Ile Pro Ala
  1               5                  10                  15

Ser Ser Ser Asp Val Val Met Thr Gln Thr Pro Leu Ser Leu Pro Val
                 20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val
        130                 135

<210> SEQ ID NO 30
<211> LENGTH: 410
<212> TYPE: DNA
<213> ORGANISM: homo sapiens

<400> SEQUENCE: 30
aagatggagt cacagaccca ggtcttcata tccatactgc tctggttata tggagctgat      60
gggaacattg taatgaccca atctcccaaa tccatgtcca tgtcagtagg agagagggtc     120
accttgacct gcaaggccag tgagaatgtg gttacttatg tttcctggta tcaacagaaa     180
ccagagcagt ctcctaaact gctgatatac ggggcatcca ccggtacac tggggtcccc       240 gatcgcttca caggcagtgg atctgcaaca gatttcactc tgaccatcag cagtgtgcag     300
```

```
gctgaagacc ttgcagatta tcactgtgga cagggttaca gctatccgta cacgttcgga    360 gggggggacca agctggaaat aaaacgggct gatgctgcac caactgtatc              410
```

<210> SEQ ID NO 31
<211> LENGTH: 135
<212> TYPE: PRT
<213> ORGANISM: homo sapiens

<400> SEQUENCE: 31

```
Met Glu Ser Gln Thr Gln Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Gly Thr Lys Leu Glu Ile Lys Arg
        115                 120                 125

Ala Asp Ala Ala Pro Thr Val
    130                 135
```

<210> SEQ ID NO 32
<211> LENGTH: 5
<212> TYPE: PRT
<213> ORGANISM: Mus musculus

<400> SEQUENCE: 32

```
Asp Tyr Thr Met Asn
1               5
```

<210> SEQ ID NO 33
<211> LENGTH: 5
<212> TYPE: PRT
<213> ORGANISM: Mus musculus

<400> SEQUENCE: 33

```
Gly Tyr Tyr Met His
1               5
```

<210> SEQ ID NO 34
<211> LENGTH: 5
<212> TYPE: PRT
<213> ORGANISM: Mus musculus

<400> SEQUENCE: 34

```
Asp Tyr Gly Val Asn
1               5
```

<210> SEQ ID NO 35
<211> LENGTH: 5
<212> TYPE: PRT
<213> ORGANISM: Mus musculus

<400> SEQUENCE: 35

```
Gly Tyr Tyr Trp Asn
1               5

<210> SEQ ID NO 36
<211> LENGTH: 5
<212> TYPE: PRT
<213> ORGANISM: Mus musculus

<400> SEQUENCE: 36

Asp Tyr Tyr Met Asn
1               5

<210> SEQ ID NO 37
<211> LENGTH: 5
<212> TYPE: PRT
<213> ORGANISM: Mus musculus

<400> SEQUENCE: 37

Tyr Tyr Trp Met Asn
1               5

<210> SEQ ID NO 38
<211> LENGTH: 17
<212> TYPE: PRT
<213> ORGANISM: Mus musculus

<400> SEQUENCE: 38

Leu Leu His Pro Phe Asn Gly Gly Thr Ser Tyr Asn Gln Lys Phe Lys
1               5                   10                  15

Gly

<210> SEQ ID NO 39
<211> LENGTH: 17
<212> TYPE: PRT
<213> ORGANISM: Mus musculus

<400> SEQUENCE: 39

Ala Val Asn Pro Asn Thr Ala Gly Leu Thr Tyr Asn Gln Arg Phe Lys
1               5                   10                  15

Asp

<210> SEQ ID NO 40
<211> LENGTH: 16
<212> TYPE: PRT
<213> ORGANISM: Mus musculus

<400> SEQUENCE: 40

Ile Ile Trp Gly Asp Gly Arg Thr Asp Tyr Asn Ser Ala Leu Lys Ser
1               5                   10                  15

<210> SEQ ID NO 41
<211> LENGTH: 16
<212> TYPE: PRT
<213> ORGANISM: Mus musculus

<400> SEQUENCE: 41

Tyr Ile Arg Tyr Asp Gly Ser Asn Asn Tyr Asn Pro Ser Leu Lys Asn
1               5                   10                  15

<210> SEQ ID NO 42
<211> LENGTH: 19
<212> TYPE: PRT
<213> ORGANISM: Mus musculus
```

```
<400> SEQUENCE: 42

Phe Ile Lys Asn Lys Phe Asn Gly Tyr Thr Thr Glu Tyr Asn Thr Ser
1               5                   10                  15
Val Lys Gly

<210> SEQ ID NO 43
<211> LENGTH: 19
<212> TYPE: PRT
<213> ORGANISM: Mus musculus

<400> SEQUENCE: 43

Glu Ile Arg Leu Lys Ser Asn Asn Tyr Ala Thr His Tyr Ala Glu Ser Val
1               5                   10                  15
Lys Gly

<210> SEQ ID NO 44
<211> LENGTH: 10
<212> TYPE: PRT
<213> ORGANISM: Mus musculus

<400> SEQUENCE: 44

Gly Thr Gly Arg Asn Tyr Ala Met Asp Tyr
1               5                   10

<210> SEQ ID NO 45
<211> LENGTH: 13
<212> TYPE: PRT
<213> ORGANISM: Mus musculus

<400> SEQUENCE: 45

Val Asp Tyr Asp Asp Tyr Gly Tyr Trp Phe Phe Asp Val
1               5                   10

<210> SEQ ID NO 46
<211> LENGTH: 9
<212> TYPE: PRT
<213> ORGANISM: Mus musculus

<400> SEQUENCE: 46

Ala Pro Gly Asn Arg Ala Met Glu Tyr
1               5

<210> SEQ ID NO 47
<211> LENGTH: 9
<212> TYPE: PRT
<213> ORGANISM: Mus musculus

<400> SEQUENCE: 47

Gly Gly Ile Thr Val Ala Met Asp Tyr
1               5

<210> SEQ ID NO 48
<211> LENGTH: 10
<212> TYPE: PRT
<213> ORGANISM: Mus musculus

<400> SEQUENCE: 48

Gly Leu Gly Arg Ser Tyr Ala Met Asp Tyr
1               5                   10

<210> SEQ ID NO 49
<211> LENGTH: 8
<212> TYPE: PRT
<213> ORGANISM: Mus musculus
```

<400> SEQUENCE: 49

Tyr Asp Gly Ser Ser Arg Asp Tyr
1               5

<210> SEQ ID NO 50
<211> LENGTH: 11
<212> TYPE: PRT
<213> ORGANISM: Mus musculus

<400> SEQUENCE: 50

Lys Ala Ser Gln Thr Val Thr Asn Asp Leu Ala
1               5                   10

<210> SEQ ID NO 51
<211> LENGTH: 11
<212> TYPE: PRT
<213> ORGANISM: Mus musculus

<400> SEQUENCE: 51

Lys Ala Ser Gln Ser Val Thr Asn Asp Val Ala
1               5                   10

<210> SEQ ID NO 52
<211> LENGTH: 11
<212> TYPE: PRT
<213> ORGANISM: Mus musculus

<400> SEQUENCE: 52

Lys Ala Ser Gln Ser Val Thr Asn Asp Val Thr
1               5                   10

<210> SEQ ID NO 53
<211> LENGTH: 11
<212> TYPE: PRT
<213> ORGANISM: Mus musculus

<400> SEQUENCE: 53

Lys Ala Ser Gln Ser Val Ser Asn Asp Val Ala
1               5                   10

<210> SEQ ID NO 54
<211> LENGTH: 16
<212> TYPE: PRT
<213> ORGANISM: Mus musculus

<400> SEQUENCE: 54

Arg Ser Ser Gln Ser Leu Val His Ser Asn Gly Asn Thr Tyr Leu His
1               5                   10                  15

<210> SEQ ID NO 55
<211> LENGTH: 11
<212> TYPE: PRT
<213> ORGANISM: Mus musculus

<400> SEQUENCE: 55

Lys Ala Ser Glu Asn Val Val Thr Tyr Val Ser
1               5                   10

<210> SEQ ID NO 56
<211> LENGTH: 7
<212> TYPE: PRT
<213> ORGANISM: Mus musculus

<400> SEQUENCE: 56

Tyr Ala Ser Asn Arg Tyr Thr
1               5

<210> SEQ ID NO 57
<211> LENGTH: 7
<212> TYPE: PRT
<213> ORGANISM: Mus musculus

<400> SEQUENCE: 57

Tyr Ala Ser Asn Arg Tyr Thr
1               5

<210> SEQ ID NO 58
<211> LENGTH: 7
<212> TYPE: PRT
<213> ORGANISM: Mus musculus

<400> SEQUENCE: 58

Phe Ala Ser Asn Arg Tyr Thr
1               5

<210> SEQ ID NO 59
<211> LENGTH: 7
<212> TYPE: PRT
<213> ORGANISM: Mus musculus

<400> SEQUENCE: 59

Tyr Ala Ser Lys Arg Tyr Thr
1               5

<210> SEQ ID NO 60
<211> LENGTH: 7
<212> TYPE: PRT
<213> ORGANISM: Mus musculus

<400> SEQUENCE: 60

Lys Val Ser Asn Arg Phe Ser
1               5

<210> SEQ ID NO 61
<211> LENGTH: 7
<212> TYPE: PRT
<213> ORGANISM: Mus musculus

<400> SEQUENCE: 61

Gly Ala Ser Asn Arg Tyr Thr
1               5

<210> SEQ ID NO 62
<211> LENGTH: 9
<212> TYPE: PRT
<213> ORGANISM: Mus musculus

<400> SEQUENCE: 62

Gln Gln Asp Tyr Ser Ser Pro Leu Thr
1               5

<210> SEQ ID NO 63
<211> LENGTH: 9
<212> TYPE: PRT
<213> ORGANISM: Mus musculus

<400> SEQUENCE: 63

Gln Gln Asp Tyr Arg Ser Pro Trp Thr
1               5

```
<210> SEQ ID NO 64
<211> LENGTH: 9
<212> TYPE: PRT
<213> ORGANISM: Mus musculus

<400> SEQUENCE: 64

Gln Gln Asp Tyr Ser Ser Pro Leu Thr
1               5

<210> SEQ ID NO 65
<211> LENGTH: 9
<212> TYPE: PRT
<213> ORGANISM: Mus musculus

<400> SEQUENCE: 65

Gln Gln Asp His Ser Tyr Pro Trp Thr
1               5

<210> SEQ ID NO 66
<211> LENGTH: 9
<212> TYPE: PRT
<213> ORGANISM: Mus musculus

<400> SEQUENCE: 66

Ser Gln Ser Thr His Val Pro Tyr Thr
1               5

<210> SEQ ID NO 67
<211> LENGTH: 9
<212> TYPE: PRT
<213> ORGANISM: Mus musculus

<400> SEQUENCE: 67

Gly Gln Gly Tyr Ser Tyr Pro Tyr Thr
1               5
```